(12) United States Patent
Fukasawa et al.

(10) Patent No.: US 12,602,017 B2
(45) Date of Patent: Apr. 14, 2026

(54) WRISTWATCH AND WRISTWATCH-TYPE DISPLAY DEVICE

(71) Applicants:NAOTO FUKASAWA DESIGN LTD., Tokyo (JP); tha ltd., Tokyo (JP)

(72) Inventors: Naoto Fukasawa, Tokyo (JP); Yugo Nakamura, Tokyo (JP)

(73) Assignees: NAOTO FUKASAWA DESIGN LTD., Tokyo (JP); tha ltd., Tokyo (JP)

( * ) Notice: Subject to any disclaimer, the term of this patent is extended or adjusted under 35 U.S.C. 154(b) by 46 days.

(21) Appl. No.: 18/254,383

(22) PCT Filed: Oct. 25, 2021

(86) PCT No.: PCT/JP2021/039218
§ 371 (c)(1),
(2) Date: Nov. 20, 2023

(87) PCT Pub. No.: WO2022/113599
PCT Pub. Date: Jun. 2, 2022

(65) Prior Publication Data
US 2024/0319678 A1 Sep. 26, 2024

(30) Foreign Application Priority Data
Nov. 26, 2020 (JP) ................................. 2020-196205

(51) Int. Cl.
G04G 21/02 (2010.01)
A61B 5/00 (2006.01)
(Continued)

(52) U.S. Cl.
CPC ........... G04G 21/025 (2013.01); A61B 5/681 (2013.01); G04G 9/007 (2013.01); G04G 21/08 (2013.01);
(Continued)

(58) Field of Classification Search
CPC ...... G04G 21/025; G04G 9/007; G04G 21/08; G04G 9/00; G04G 21/02; A61B 5/681;
(Continued)

(56) References Cited

U.S. PATENT DOCUMENTS 10,620,590 B1 * 4/2020 Guzman ................ G06F 3/0482
11,977,410 B2 * 5/2024 Kuwabara .............. G04G 17/06
(Continued)

FOREIGN PATENT DOCUMENTS

JP H07-253773 A 10/1995
JP 1158328 S 11/2002
(Continued)

OTHER PUBLICATIONS

International Search Report in PCT/JP2021/039218, mailed Jan. 11, 2022, 4pp.

*Primary Examiner* — Ibrahim A Khan
(74) *Attorney, Agent, or Firm* — HAUPTMAN HAM, LLP

(57) ABSTRACT

A wristwatch includes: a wristwatch body having a rectangular parallelepiped shape; five display units that are formed over entire areas of five faces excluding a lower face out of six faces that form a surface of the wristwatch body; a display control unit that controls a display on each of five display units; and detection units that detect at least one information out of position information of the wristwatch, posture information of the wristwatch, movement information of the wristwatch, and health relating information of a user of the wristwatch. The display control unit may have a function of controlling display on each of five display units based on at least one information detected by the detection unit. According to the present invention, it is possible to provide a wristwatch having a new value not obtained by the prior art.

12 Claims, 30 Drawing Sheets

(51) Int. Cl.

| | | |
|---|---|---|
| *G04G 9/00* | (2006.01) | |
| *G04G 21/08* | (2010.01) | |
| *G06F 3/0346* | (2013.01) | |
| *G06F 3/0488* | (2022.01) | |
| *G09G 3/32* | (2016.01) | |

(52) U.S. Cl.
CPC .......... *G06F 3/0346* (2013.01); *G06F 3/0488* (2013.01); *G09G 3/32* (2013.01); *A61B 2562/0219* (2013.01); *G09G 2300/026* (2013.01); *G09G 2354/00* (2013.01)

(58) Field of Classification Search
CPC ........... A61B 2562/0219; G06F 3/0346; G06F 3/0488; G09G 3/32; G09G 2300/026; G09G 2354/00
See application file for complete search history.

(56) References Cited

U.S. PATENT DOCUMENTS

| | | | |
|---|---|---|---|
| 2009/0164219 A1* | 6/2009 | Yeung ....................... G06F 3/01 | |
| | | | 704/258 |
| 2013/0044571 A1 | 2/2013 | Ihashi | |
| 2015/0099477 A1* | 4/2015 | Sato ........................... G01S 1/00 | |
| | | | 455/90.1 |
| 2015/0185819 A1 | 7/2015 | Saito | |
| 2015/0227281 A1* | 8/2015 | Yoo ........................ G06F 1/1647 | |
| | | | 345/1.3 |
| 2015/0253739 A1* | 9/2015 | Lida ..................... G04G 9/0076 | |
| | | | 368/80 |
| 2015/0254043 A1* | 9/2015 | Hwang ................. G06F 3/1423 | |
| | | | 345/1.1 |
| 2015/0301506 A1* | 10/2015 | Koumaiha ............. G04G 21/08 | |
| | | | 345/174 |
| 2016/0018900 A1* | 1/2016 | Tu ......................... G06F 1/3218 | |
| | | | 345/156 |
| 2016/0079333 A1* | 3/2016 | Shishido .............. H10K 59/131 | |
| | | | 257/72 |
| 2016/0116941 A1* | 4/2016 | Kuwabara ............. G02F 1/1368 | |
| | | | 361/679.03 |
| 2016/0125846 A1* | 5/2016 | Xu ............................ G09G 5/10 | |
| | | | 368/240 |
| 2016/0256082 A1* | 9/2016 | Ely ........................ A61B 5/7282 | |
| 2016/0291547 A1* | 10/2016 | Bell ................... G04B 37/0033 | |
| 2017/0115752 A1* | 4/2017 | Matsuno .............. G01C 22/006 | |
| 2017/0123487 A1* | 5/2017 | Hazra .............. G06F 3/0482 | |
| 2017/0160898 A1* | 6/2017 | Lee ........................ G06F 3/0488 | |
| 2017/0206857 A1* | 7/2017 | Li ............................. G09G 3/38 | |
| 2017/0243385 A1* | 8/2017 | Mitsugi ................... G09F 9/372 | |
| 2018/0011447 A1* | 1/2018 | Yoshizumi ............. G04B 47/00 | |
| 2018/0110415 A1 | 4/2018 | Sasahara et al. | |
| 2018/0205675 A1* | 7/2018 | Koo ........................ H04W 4/12 | |
| 2018/0329587 A1* | 11/2018 | Ko ........................... G06F 1/163 | |
| 2018/0350318 A1* | 12/2018 | Lee ........................... G09G 3/20 | |
| 2019/0018445 A1* | 1/2019 | Watanabe ............. G06F 1/3265 | |
| 2019/0146219 A1* | 5/2019 | Rodriguez ............ G06F 3/0482 | |
| | | | 345/633 |
| 2019/0304153 A1 | 10/2019 | Mitsugi et al. | |
| 2020/0097167 A1* | 3/2020 | Hattori ................. G06F 1/1698 | |
| 2020/0118321 A1 | 4/2020 | Mitsugi et al. | |
| 2020/0235084 A1* | 7/2020 | Wu ........................ H10D 86/60 | |
| 2020/0266246 A1* | 8/2020 | Bok ..................... H10K 71/221 | |
| 2020/0292998 A1 | 9/2020 | Yoshizumi et al. | |
| 2020/0342816 A1* | 10/2020 | Bok ......................... G09G 3/32 | |
| 2021/0263370 A1* | 8/2021 | Maeng ................ G02F 1/13452 | |
| 2021/0265580 A1* | 8/2021 | Jung ................... H10K 50/841 | |
| 2022/0283654 A1* | 9/2022 | Kuwabara .............. G06F 1/163 | |
| 2023/0359151 A1 | 11/2023 | Yoshizumi et al. | |

FOREIGN PATENT DOCUMENTS

| | | |
|---|---|---|
| JP | 2007-206577 A | 8/2007 |
| JP | 2013-040865 A | 2/2013 |
| JP | 2015123300 A | 7/2015 |
| JP | 2017-176988 A | 10/2017 |
| JP | 2018013477 A | 1/2018 |
| JP | 2018068478 A | 5/2018 |
| JP | 2019194612 A | 11/2019 |
| JP | 2020016797 A | 1/2020 |

* cited by examiner

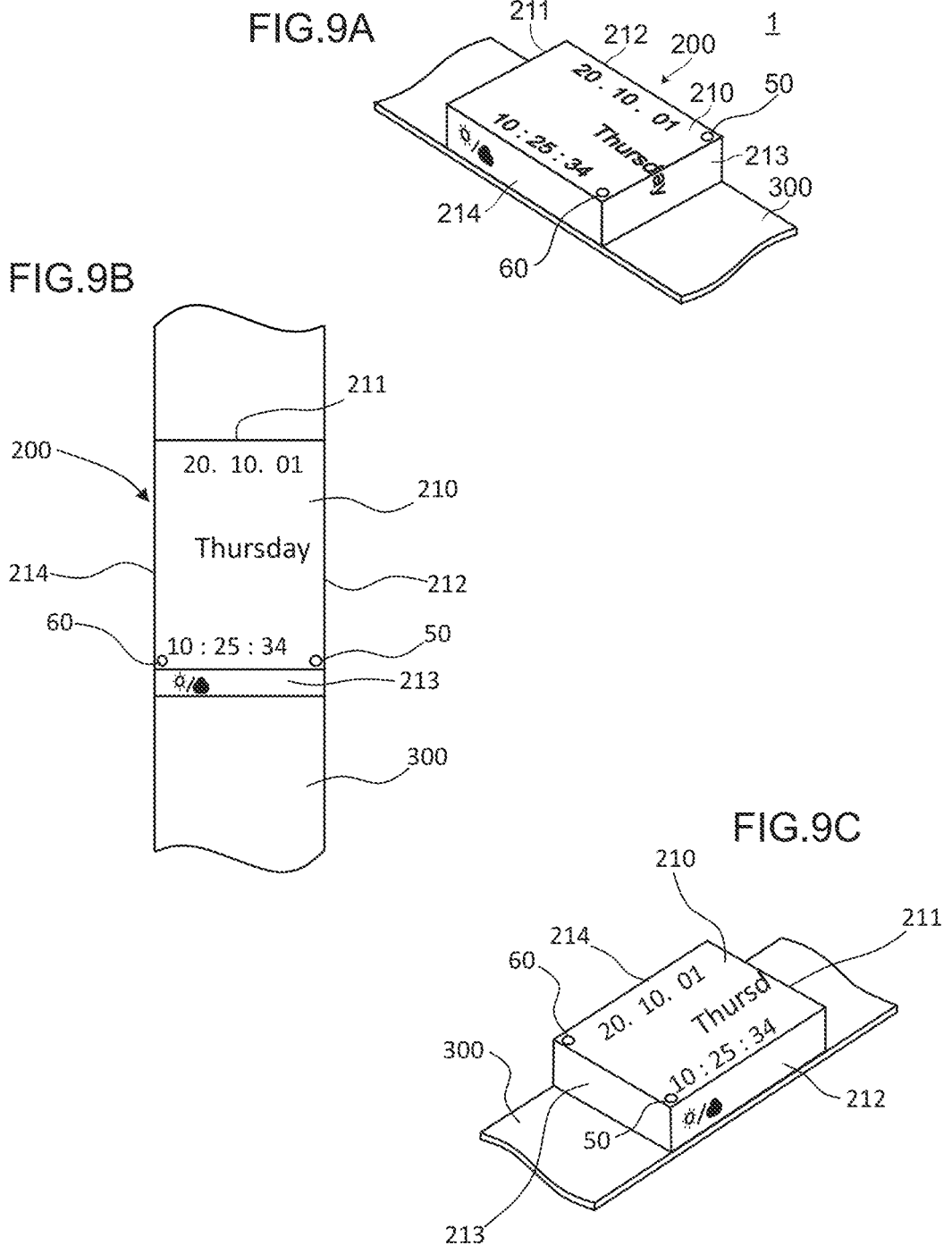

FIG.10A
FIG.10B
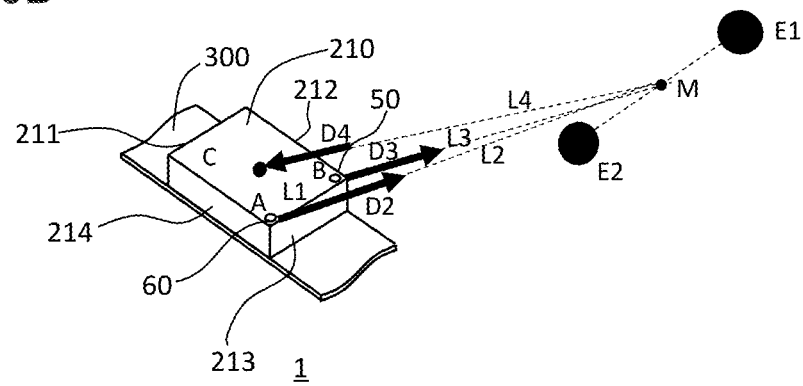
FIG.10C
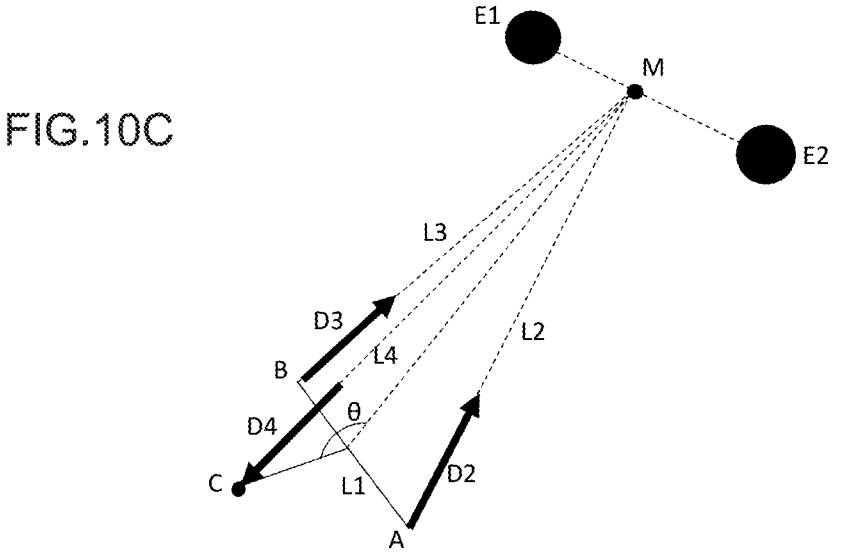

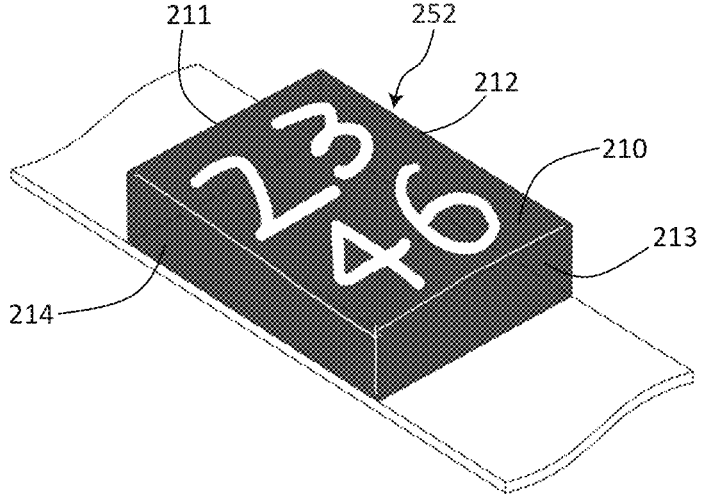
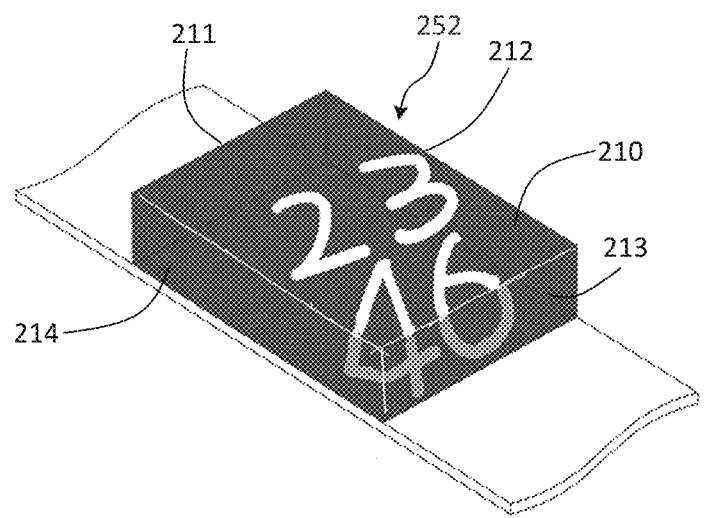
FIG.14

① TRANSITION BY SWIPING 211    212

210
G1
213 — APPLICATION (1)

214
1
272
P

PREVIEW OF SUCCEEDING APPLICATION (2)
G2

②

211    212

210    272
G1 Swiping giving user feeling as if user pulls screen with soft touch and with slight resistance
213

214
1
G2
P

SWIPING GIVING USER FEELING AS IF USER
IS PULLING CURTAIN WITH FINGER

③                                                    FIG.35

AFTER
SWIPING

APPLICATION (2)

PREVIEW OF
APPLICATION (3)

<u>IMAGES BEING ATTRACTED WHEN IMAGES ARE PULLED TO SOME EXTENT</u>

WRISTWATCH AND WRISTWATCH-TYPE DISPLAY DEVICE

RELATED APPLICATIONS

The present application is a National Phase of International Application No. PCT/JP2021/039218 filed Oct. 25, 2021, which claims priority to Japanese Application No. 2020-196205 filed Nov. 26, 2020.

TECHNICAL FIELD

The present invention relates to a wristwatch and a wristwatch type display device.

BACKGROUND ART

Wristwatches with new and unconventional value are known (see, for example, Pat. Refs. 1 and 2). FIG. 36 illustrates a conventional wristwatch 900. The wristwatch 900 shown in FIG. 36 is the wristwatch described in FIG. 13A to FIG. 13C in Patent Document 2. In FIG. 36, the figure on the left is a diagram of the wristwatch 900 when displayed, and the figure on the right is a diagram of the wristwatch 900 when not displayed. As shown in FIG. 36, the wristwatch 900 does not display anything when not displayed, let alone a clock display, making it a wristwatch that, although it is a wristwatch, does not make the wearer aware of the presence of a time display when not displayed, providing a new value to wristwatches. Prior Art Literature Patent Literature Patent document 1: Design registration No. 1158328

Patent document 2: Patent publication No. 2007-206577

SUMMARY OF INVENTION

Problem to be Solved by the Invention

However, in human society, new times call for products with new 2 value, and the field of wristwatches is no exception.

This invention has been made in view of the above circumstances, and the purpose of this invention is to provide wristwatch and a wristwatch-type display device having a new value not found in the past.

Means to Solve the Problem

[1] The wristwatch of the present invention comprising a wristwatch body having a rectangular parallelepiped shape, at least two display units that are formed over entire areas of each of "an upper face on a side opposite to a lower face directed toward a side of an arm of a user at a time of using the wristwatch" and "at least one side face out of four side faces" out of six faces that form a surface of the wristwatch body, a display control unit that controls a display on each of the at least two display units, and a detection unit that detects at least one information out of position information of the wristwatch, posture information of the wristwatch, movement information of the wristwatch, and health relating information of a user of the wristwatch. The display control unit has a function of controlling display on each of the at least two display units based on the at least one information detected by the detection unit.

[2] In the wristwatch of the present invention, the display control unit preferably has a function of controlling display on each of the at least two display units such that the images displayed on the at least two display units are moved in a linked manner or are associated with each other.

In the configuration, "are moved in a linked manner" includes a case where the images displayed on the at least two display units move in a seamless manner by straddling the at least two display units. Further, "are moved in a linked manner" includes a case where the at least two display units change a turn on/off state one after another based on a predetermined rule or at random. For example "are moved in a linked manner" includes a case where, with respect to the at least two display units, one display unit performs display in red and, thereafter, the other display unit performs display in the same color or in different color. In this case, the respective display units perform display sequentially and independently in accordance with a predetermined rule.

[3] In the wristwatch of the present invention, it is preferred that at least two display units include five display units that are formed over entire areas of five faces that are formed of the upper face and the four side faces. That is, the wristwatch of the present invention preferably has a rectangular wristwatch body, five displays formed over the entire area of each of the five surfaces except for the lower surface of the six surfaces, a display control unit controlling the display of each of said five displays, and a detection unit that detects at least one information out of position information of the wristwatch, posture information of the wristwatch, movement information of the wristwatch, and health relating information of a user of the wristwatch, the display control unit having a function of controlling display on each of the at least two display units based on the at least one information detected by the detection unit.

[4] In the wristwatch of the present invention, it is preferable that the five faces of the wristwatch boy have no pattern thereon in a state where the five display units are not allowed to perform any display.

[5] In the wristwatch, preferably, the five display units are formed of five organic EL display sheets or five micro LED display sheets, and each of the five organic EL display sheets or each of the five micro LED display sheets is laminated to each of the five faces of the wristwatch body.

[6] In the wristwatch of the present invention, preferably the five display units are formed of one organic EL display sheet or one micro LED display sheet, and the one organic EL display sheet or the one micro LED display sheet is bent along an outer shape of the wristwatch body and is laminated to the wristwatch body.

[7] In the wristwatch of the present invention, preferably a first electrode group for supplying power and electric signals to the organic EL display sheets or the micro LED display sheets is mounted on the five faces of the wristwatch body in an exposed manner, and a second electrode group for receiving the power and the electric signals from the first electrode group is mounted on a back surface of the organic EL display sheets or the micro LED sheets at a position that corresponds to the first electrode group, and the wristwatch includes a drive circuit that supplies an electric signal for controlling a turn on/off state of respective pixels of the organic EL display sheets or the micro LED display sheets, and the first electrode group and the second electrode group are electrically connected to each other.

[8] In the wristwatch of the present invention, it is preferable that each of gaps formed between five display units is embedded with a black member so as to prevent the gap from being visually recognized from the outside.

[9] In the watch of the invention, a protective member is preferably applied to by coating to five display units so as to cover all five display units and is cured.

[10] In the wristwatch of the present invention, the display control unit preferably controls the display on each of the five display units as if the inside of the wristwatch body is viewed in a see-through manner as viewed from the user.

[11] In the watch of the present invention, each of the five display units is preferably formed of a touch panel.

[12] In the wristwatch of the present invention, preferably the display control unit controls the display on each of the five display units such that an image is changed over corresponding to a swipe operation performed by a finger of the user on the touch panel.

[13] In the wristwatch of the present invention, the detection unit preferably includes at least one imaging element that is disposed on any portion of the wristwatch, and an arithmetic operation unit that extracts information relating to a positional relationship between eyes of the user of the wristwatch and the wristwatch based on an image of the eyes of the user who uses the wristwatch that is imaged by the at least one imaging elements.

[14] In the wristwatch of the present invention, the detection unit is preferably a three-dimensional acceleration sensor that detects posture information of the wristwatch, and the detection unit detects information relating to three-dimensional posture of the wristwatch as the posture information of the wristwatch.

[15] In the wristwatch of the present invention, the detection unit is preferably a three-dimensional acceleration sensor that detects movement information of the wristwatch, and the detection unit detects information relating to three-dimensional movement of the wristwatch as the movement information of the wristwatch.

[16] In the wristwatch of the present invention, the detection unit is preferably a pulse gauge, a thermometer, a blood pressure gauge, an electrocardiograph gauge or a three-dimensional acceleration sensor that detects health relating information of the user of the wristwatch, and the detection unit detects information relating to a pulse, a body temperature, a blood pressure or activity of the user of the wristwatch as the health relating information of the user of the wristwatch.

[17] A wristwatch type display device comprising a wristwatch type display device body having a rectangular parallelepiped shape, at least two display units that are formed over entire areas of each of "an upper face on a side opposite to a lower face directed to an arm side of a user at a time of using the wristwatch type display device" and "at least one side face out of four side faces" out of six faces that form a surface of the wristwatch type display device body, a display control unit that controls display on each of the at least two display units, and a detection unit that detects at least one information out of position information of the wristwatch type display device body, posture information of the wristwatch type display device body, movement information of the wristwatch type display device body, and health relating information of a user of the wristwatch type display device body, the display control unit having a function of controlling display on each of the at least two display units based on the at least one information detected by the detection unit.

[18] In the wristwatch type display device of the present invention, the display control unit has preferably a function of controlling display on each of the at least two display units such that images displayed on the at least two respective display units are moved in a linked manner or are associated with each other.

[19] In the wristwatch type display device of the present invention, the at least two display units are preferably formed of five display units that are formed over entire areas of five faces formed of the upper face and the four side faces.

[20] In the wristwatch type display device of the present invention, preferably, the display control unit controls display on each of the five display units as if the inside of the wristwatch type display device body is viewed in a see-through manner as viewed from the user.

The wristwatch display device also, preferably, have each of the features possessed by the wristwatch of the present invention described above.

Effects of the Invention

According to the wristwatch and the wristwatch-type display device of the present invention, it is possible to display various images in various ways using the sides of the rectangular wristwatch body and the wristwatch-type display device body in addition to the top surface, as can be seen from the embodiment described below. The wristwatch and wristwatch-type display device can display various images which is suitable for at least one of the following information, because the display unit has a function to control the display of each of the displays formed on the sides in addition to the top surface based on at least one of the information (position information of the wristwatch and wristwatch-type display device, posture information of the wristwatch and wristwatch-type display device, movement information of the wristwatch and wristwatch-type display device, and health-related information of the user of the wristwatch and wristwatch-type display device) detected by the detection unit. Therefore, according to the wristwatch and the wristwatch-type display device of the present invention, it is possible to provide a wristwatch and a wristwatch-type display device with a new value not found in the past.

The figures are diagrams shows the state in which the wristwatch 1 according to Embodiment 1 is worn on the left arm of the user.

FIG. 2A to FIG. 2C

The figures are diagrams for explaining the wristwatch body 100 of the wristwatch 1 according to Embodiment 1 and the display unit 200 formed on five surfaces of the wristwatch body 100 except the lower surface.

FIG. 3

The figure a diagram shows the configuration of the control system for operating the wristwatch 1 according to Embodiment 1 as a functional block diagram.

FIG. 4

The figure is a diagram for explaining how to deal with gaps that occur between adjacent OLED display sheets.

FIG. 5

Figure is a diagram for explaining the state in which protective material 290 is applied and cured to cover the entire wristwatch 1.

FIG. 6A to FIG. 6C

The figures are diagrams shown for explaining the first display mode in the wristwatch 1 according to Embodiment 1.

FIG. 7A to FIG. 7C

The figures are diagrams shown for explaining the second display mode in the wristwatch 1 according to Embodiment 1.

FIG. 8A to FIG. 8C

The figures are diagrams shown for explaining the third display mode in the wristwatch 1 according to Embodiment 1.

FIG. 9A to FIG. 9C

The figures are diagrams shown for explaining the fourth display mode in the wristwatch 1 according to Embodiment 1.

FIG. 10A to FIG. 10C

The figures are diagrams for explaining the method of identifying the direction in which the user of the wristwatch 1 according to Embodiment 1 looks at the wristwatch 1.

FIG. 11

The figure a diagram shows state in which the wristwatch 1 according to Embodiment 2 worn on the left arm of the user.

FIG. 12

The figure is a diagram shows the configuration of the control system for operating the wristwatch 1 according to Embodiment 2 as a functional block diagram.

Figures 13A, 13B, 13C:
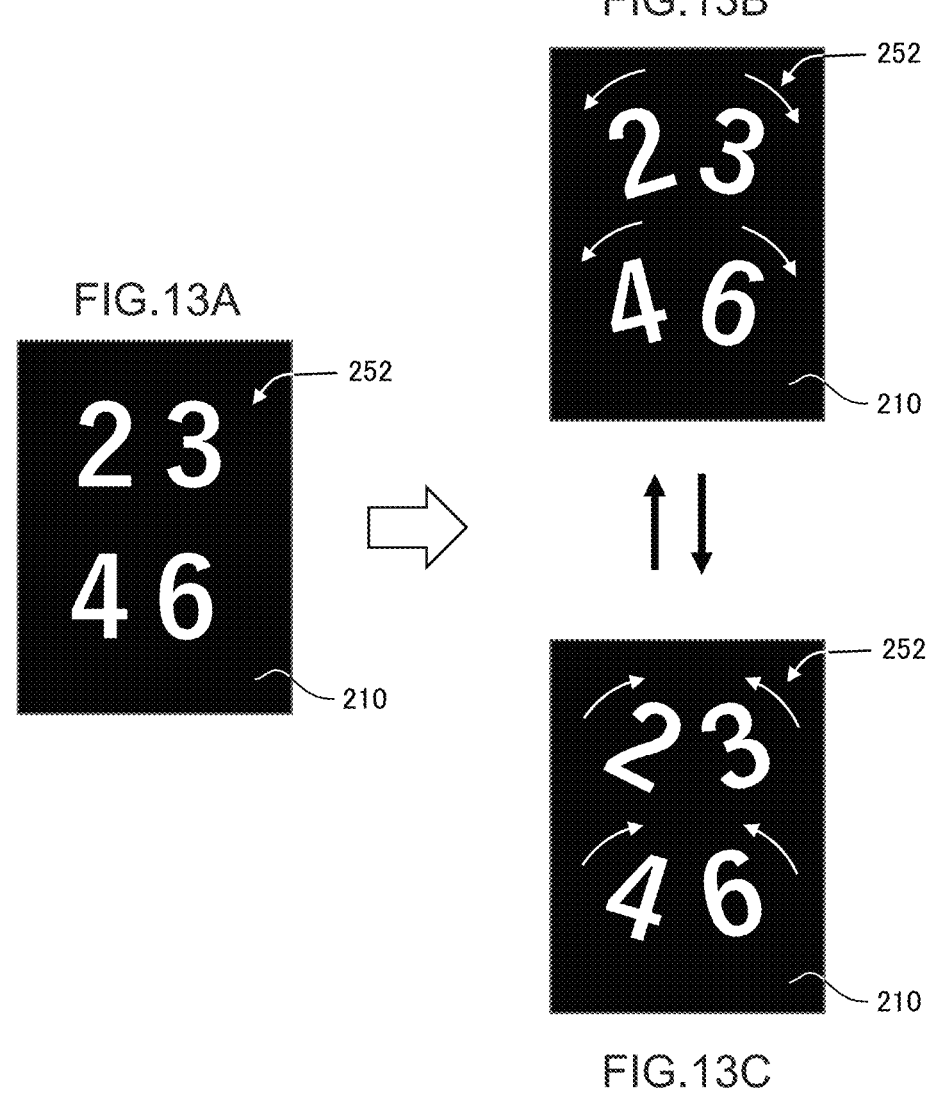
Figures 15A, 15B, 15C, 15D, 15E, 15F, 15G, 15H:
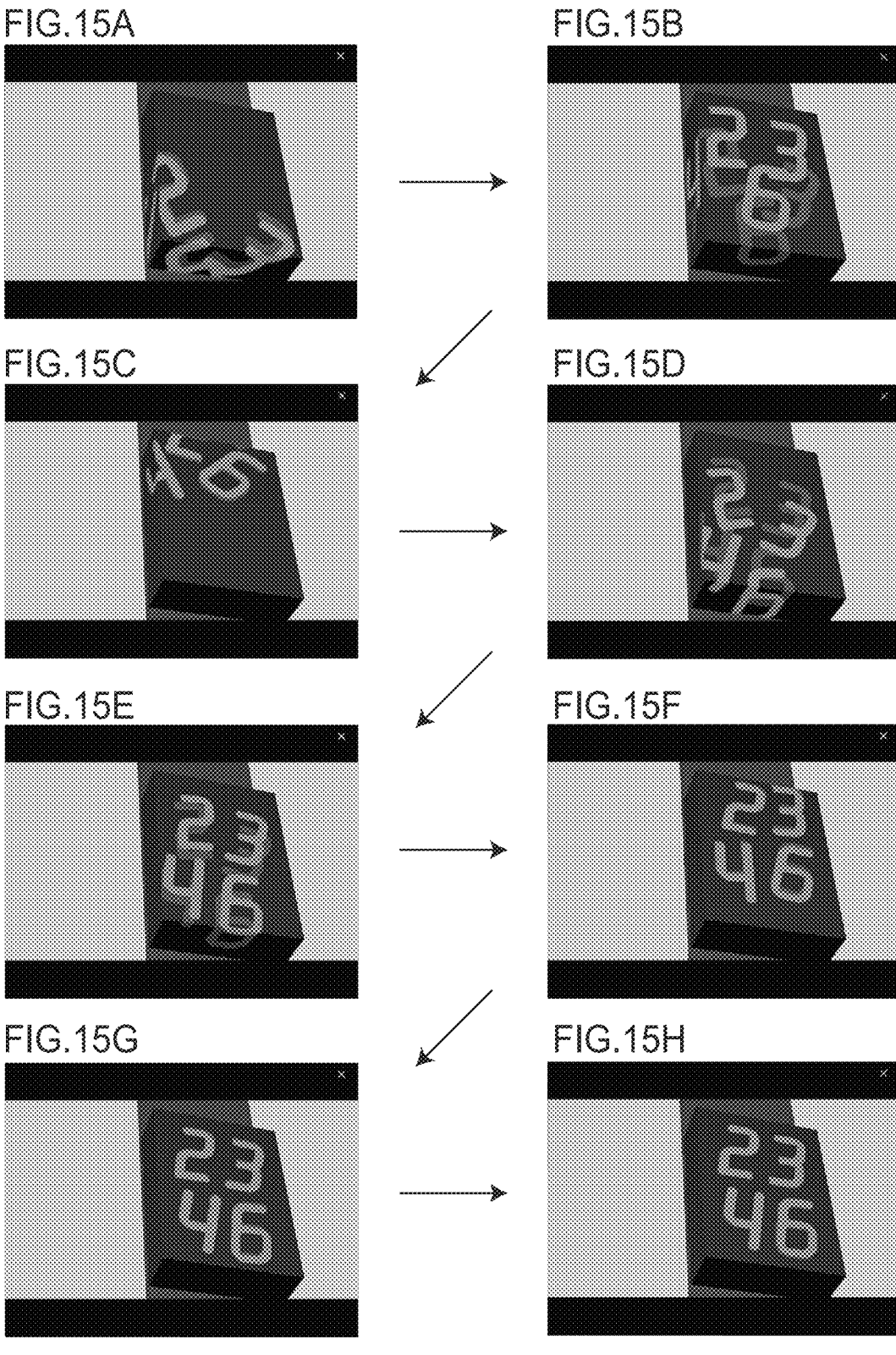

FIG. 13A to FIG. 13C

The figures are diagrams shown for explaining the first display mode of the wristwatch 1 according to Embodiment 2.

FIG. 14

The figure is a diagram shown for explaining the second display mode of the wristwatch 1 according to Embodiment 2.

FIG. 15A to FIG. 15H

The figures are diagrams shows a series of movements in which the current time protrudes into one or more of the side face display units 211 to 214 in addition to the top display 210 in the pre-programmed display mode.

FIG. 16

This figure is a diagram shows for explaining the third display mode of the wristwatch 1 according to Embodiment 2.

FIG. 17

This figure is a diagram shows for explaining the fourth display mode of the wristwatch 1 according to Embodiment 2.

FIG. 18

This figure is a diagram shows for explaining the fifth display mode of the wristwatch 1 according to Embodiment 2.

FIG. 19

This figure is a diagram shows a variation of the fifth display mode of wristwatch 1 according to Embodiment 2.

FIG. 20

This figure is a diagram shows for explaining the sixth display mode of the wristwatch 1 according to Embodiment 2.

FIG. 21

This figure is a diagram shows for explaining the seventh display mode of the wristwatch according to Embodiment 2.

Figures 22A, 22B:
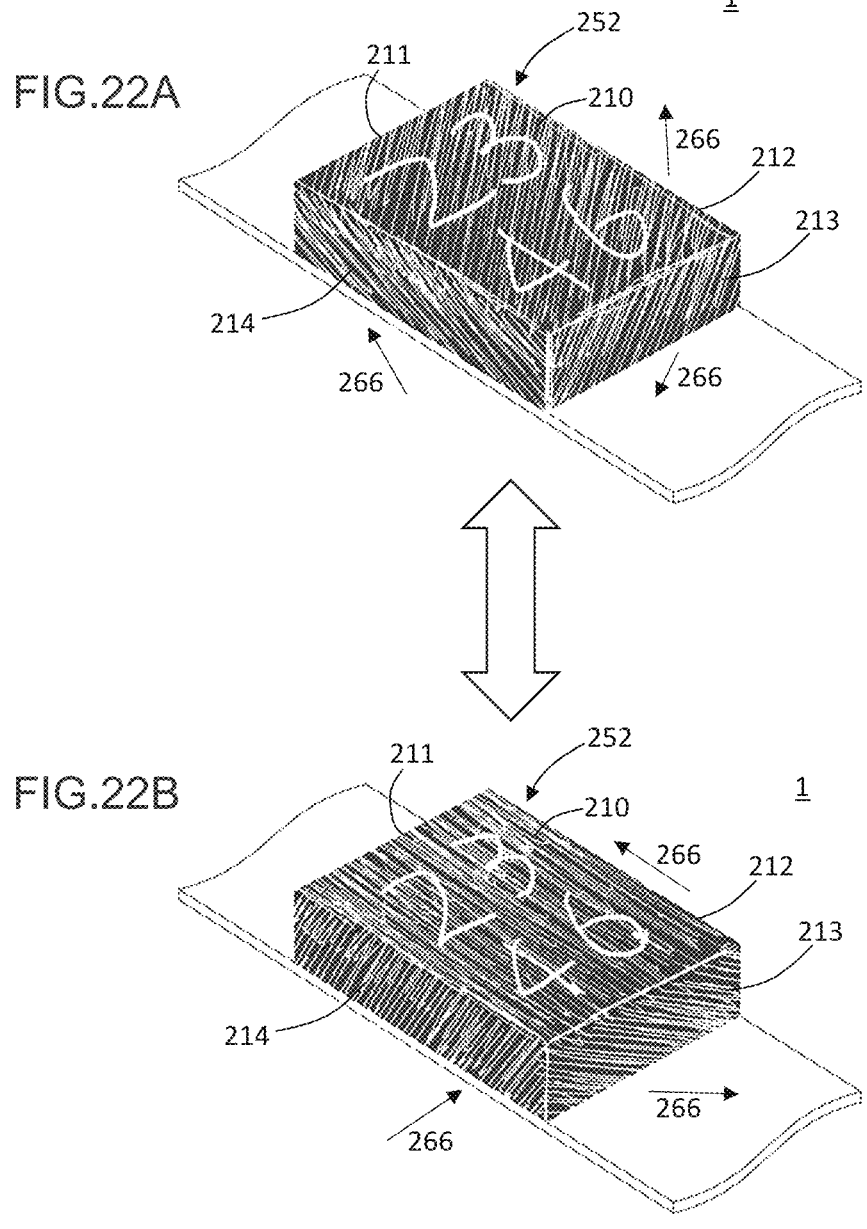

FIG. 22A and FIG. 22B

This figures are diagrams shows for explaining the eighth display mode of the wristwatch 1 according to Embodiment 2.

FIG. 23

The figure is a diagram shows the main part of the wristwatch 1 according to Embodiment 3 viewed from its underside.

FIG. 24

The figure is a diagram shows the configuration of the control system for operating the wristwatch 1 according to Embodiment 3 as a functional block diagram.

Figure 25A:
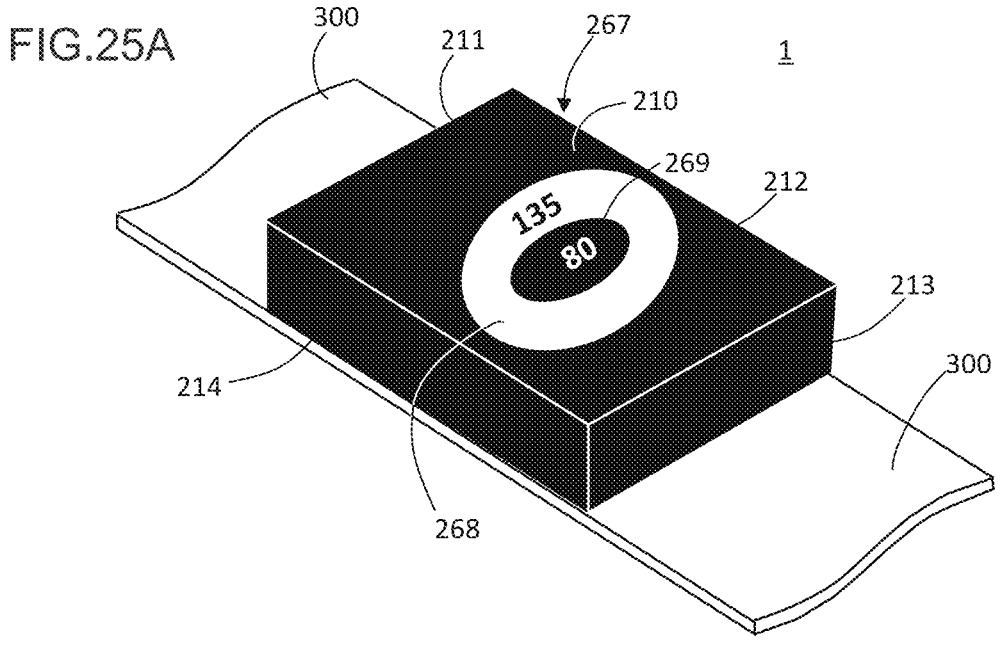
Figure 25B:
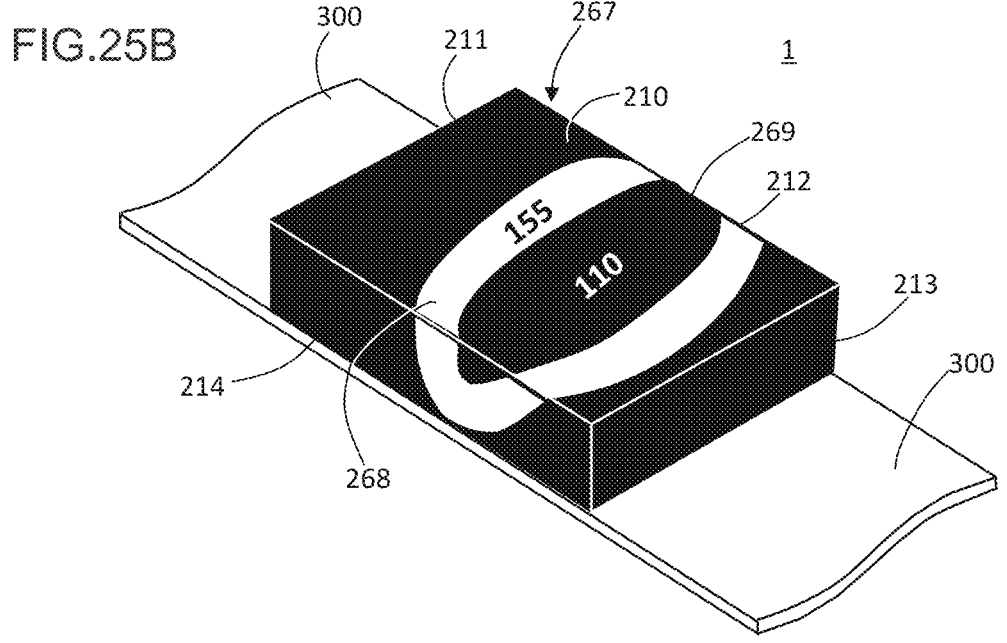

FIG. 25A and FIG. 25B

The figures are diagrams shows for explaining the first display mode of the wristwatch 1 according to Embodiment 3.

FIG. 26

The figure is a diagram shows for explaining the second display mode of the wristwatch 1 according to Embodiment 3.

FIG. 27

The figure is a diagram shows for explaining the third display mode of the wristwatch 1 according to Embodiment 3.

FIG. 28

The figure is a diagram shows for explaining the fourth display mode of the wristwatch 1 according to Embodiment 3.

FIG. 29

The figure is a diagram shows the configuration of the control system for operating the wristwatch 1 according to Embodiment 4 as a functional block diagram.

FIG. 30

This figure is a diagram shows for explaining the first display mode of the wristwatch 1 according to Embodiment 4.

FIG. 31

The figure is a diagram shows for explaining the second display mode of the wristwatch 1 according to Embodiment 4.

FIG. 32

The figure is a diagram shows for explaining a case in which the five displays 210-214 comprise three OLED display sheets.

FIG. 33A to FIG. 33I

The figures are diagrams shows for explaining a case in which the display unit 200 comprises at least two display sections.

FIG. 34

The figure is a diagram shows for explaining a display mode in which the display is switched by a swipe operation.

FIG. 35

The figure is a diagram shows for explaining a display mode in which the display is switched by a swipe operation.

FIG. 36

The figure is a diagram shows for explaining a conventional wristwatch 900.

Each form of the invention is described below.

EMBODIMENT 1

Figure 1A:
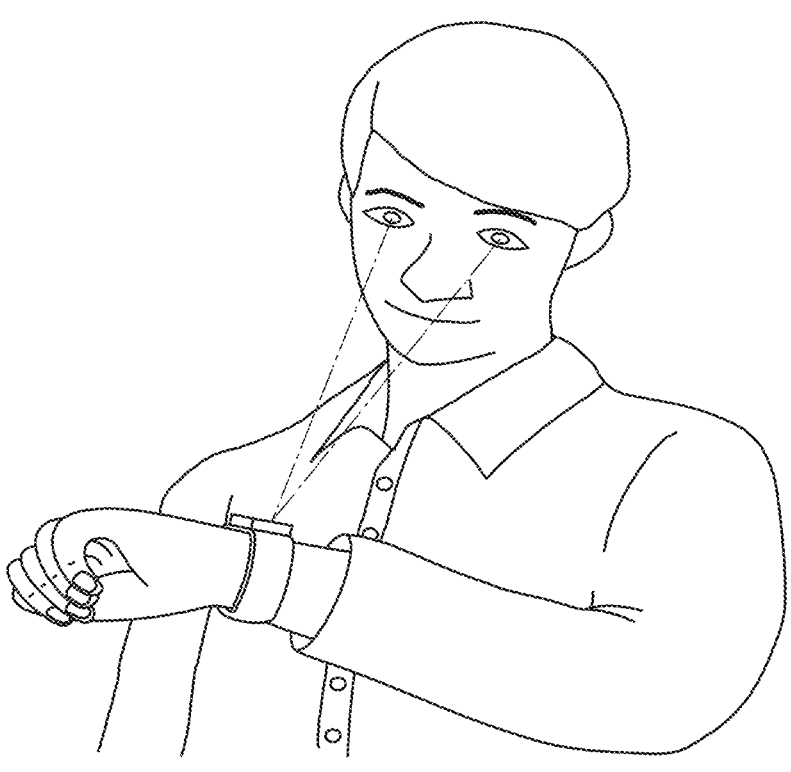
FIG. 1A and FIG. 1B
Figure 1B:
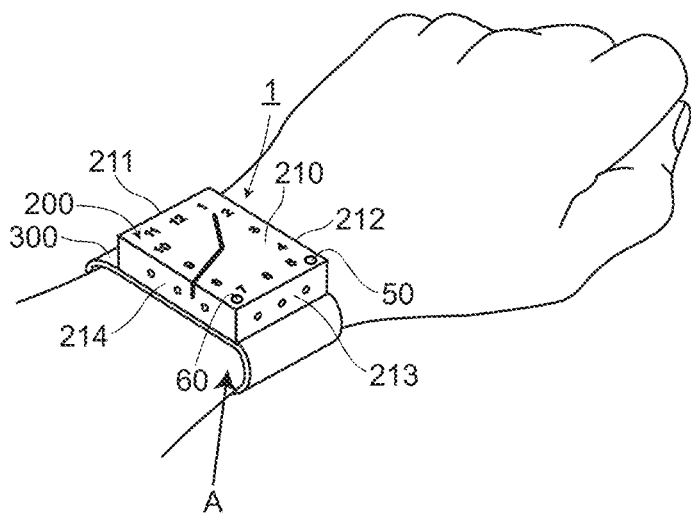

FIG. 1A and FIG. 1B shows the wristwatch 1 according to Embodiment 1 worn on the left arm of the user. FIG. 1A shows the wristwatch 1 together with the upper body of the user, and FIG. 1B is an enlarged view of the wristwatch 1 seen from a different angle from FIG. 1A. In FIG. 1B, arrow A indicates the direction of the user's line of sight when looking at the wristwatch 1 worn on the left arm wrist. In other words, when the user looks at the wristwatch 1 worn on the wrist of the left arm, it is common for the user to look at the wristwatch 1 with the elbow of the arm slightly bent toward the user's body (stomach or chest side), and this indicates the direction of the user's gaze. In FIG. 1B, the arrow A depicts the direction on the horizontal plane, but the actual direction of gaze is generally downward from the user's eyes at an angle.

Figures 2A, 2B, 2C:
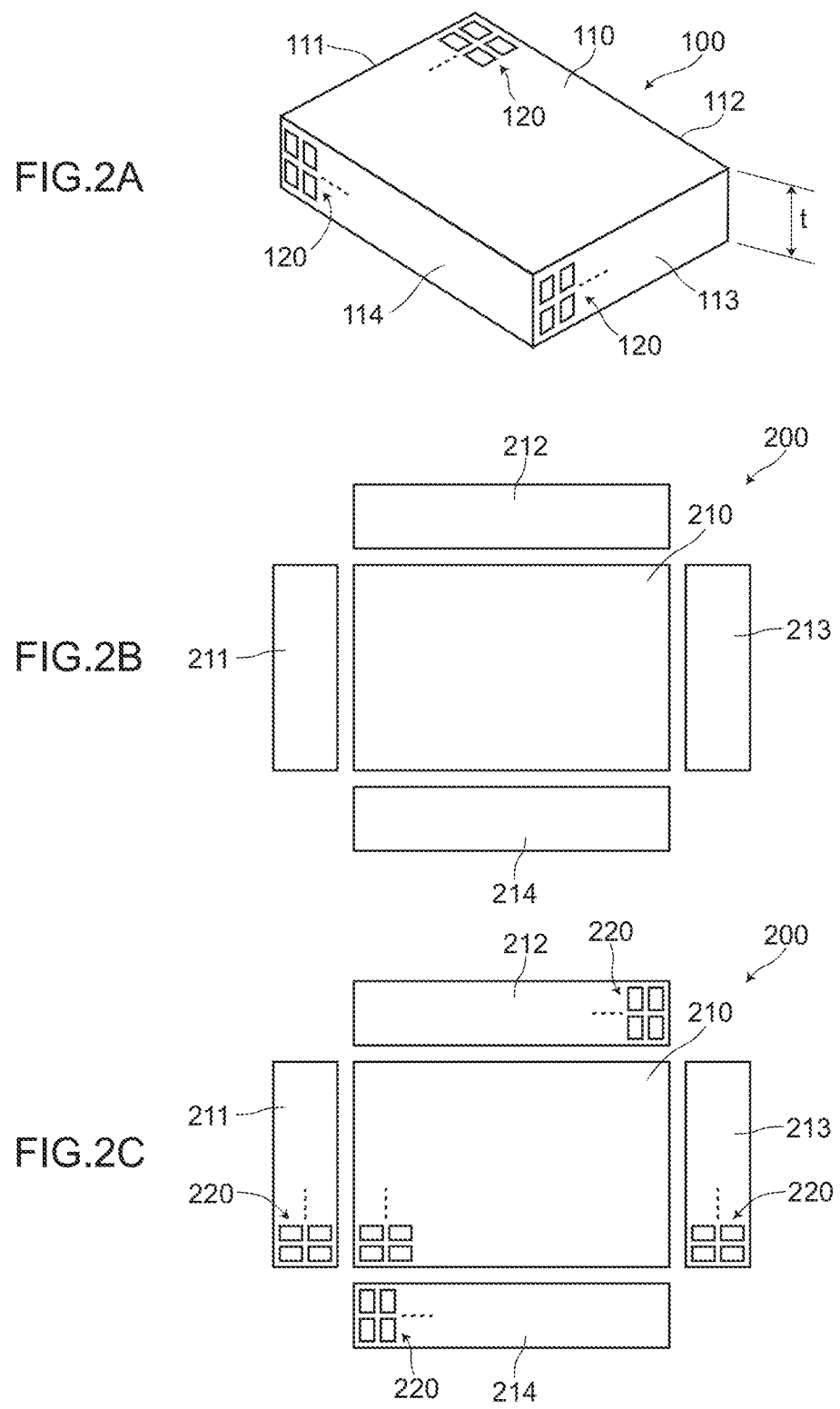

FIG. 2A to FIG. 2C illustrates the wristwatch body 100 of the wristwatch 1 according to Embodiment 1 and the display units 200 formed on five surfaces of the wristwatch body 100, excluding the lower surface that faces the user's arm side when in use. FIG. 2A is a diagonal view of the wristwatch body 100, and FIG. 2B is a plan view showing the display 200 of the wristwatch 1 developed into five displays 210-214. FIG. 2C is a bottom view showing the 200 display of the wristwatch 1 developed into five displays 210-214.

Referring to FIGS. 1A to 2C, the configuration of the wristwatch 1 according to Embodiment 1 will be described. The wristwatch 1 according to Embodiment 1 consists of a rectangular wristwatch body 100, five display areas 210-214 formed over the entire area of five sides (the top surface and four sides) of the six surfaces comprising the surface of the wristwatch body 100, excluding the bottom surface that faces the user's arm side when in use, a belt 300 for wearing the wristwatch 1 on the user's arm, the display control unit (the display control unit is described below in FIG. 3) controls the display of each of the five displays 210 to 214, and a detection unit that detects the position information of the wristwatch 1. The belt 300 is not an essential component of the wristwatch 1, but is suitably provided. In this embodiment, the detection unit consists of two image elements 50, 60 installed in either part of the wristwatch 1 and an arithmetic unit extracts information as the positional relationship between the eye of the user of the wristwatch 1 and the wristwatch 1 from the image of the eye of the user of the wristwatch 1 imaged by the elements 50, 60. The detection unit can detect information about the positional relationship between the eye of the user of the wristwatch 1 and the wristwatch 1 as positional information of the wristwatch 1. The display control unit functions to control the display of each of the five displays 210-214 based on the information detected by the elements the detection units 50, 60. At least one "information" in this application may be read as "data".

As shown in FIG. 1A and FIG. 1B, the imaging elements (image sensors) 50, 60 are preferably located at two of the four corners on the top surface of the rectangular wristwatch body 100, two corners being closer to the user in the normal state of use. However, the imaging elements 50, 60 may be located in other corners on the top surface of the wristwatch body 100. One, three or four or more image sensors may also be placed on the wristwatch body 100 or on the belt 300. When four image sensors are placed on the wristwatch 1, preferably one image sensor may be placed near the vertex where an adjacent side of the four sides of the wristwatch 1 meets the top surface of the wristwatch 1. The image sensor can be a CCD (CCD camera). The image pickup device can be a CCD (Charge Coupled Devices) image sensors or CMOS (Complementary Metal Oxide Semiconductor: Complementary Metal Oxide Semiconductor) image sensors can be used as examples. The lens of the image sensor is preferably capable of capturing images at a wide angle centered on the image sensor. In the present invention, "formed over the entire area" means that it is sufficient if the image sensor appears to be formed over the entire area from the user's viewpoint, and may not be formed over the entire area in a strict sense. Therefore, even if there is a gap between the display units 210 to 214 that cannot be displayed, it is included in the category of "formed over the entire area.

As shown in FIG. 2A, the wristwatch body 100 of the wristwatch is rectangular with a predetermined thickness t. The upper surface 110 which is opposite the bottom surface and the four sides (first side 111, second side 112, third side 113, and fourth side 114) have five faces, and as shown in FIG. 1A and FIG. 1B, five displays 210-214 are formed at five faces respectively. In addition, in the five side display units 210 to 214, the display unit formed on the upper surface 110 of the wristwatch body 100 is designated as the upper face display unit 210, and the display unit formed on the first side 111 of the wristwatch body 100 is designated as the first side display unit 211, and the display unit formed on the second side 112 of the wristwatch body 100 is designated as the second side display unit 212, and the display section formed on the third side 113 of the wristwatch body 100 is designated as the third side display unit 213, and the display formed on the fourth side 114 of the wristwatch body 100 is designated as the fourth side display unit 214.

The five display units 210-214 comprise five OLED (Electro Luminescence) display sheets. That is, the upper face display unit 210 comprises an OLED display sheet for the upper surface, and the first side display unit 211 comprises an OLED display sheet for the first side, and the second side display unit 212 comprises an OLED display sheet for the second side, and the third side display unit 213 comprises an OLED display sheet for the third side, and the fourth side display unit 214 comprises an OLED display sheet for the fourth side. When describing the first side display unit 211, second side display unit 212, third side display unit 213, and fourth side display unit 214 collectively or individually, they may be described as "side display units 210 to 214".

In the following explanation, when describing the five display units 210 to 214 as corresponding OLED display sheets, each OLED display sheet shall be referred to by the same symbol as the five display units 210 to 214 as follows: OLED display sheet 210 for the upper surface, OLED display sheet 211 for the first side, OLED display sheet 212 for the second side, OLED display sheet 213 for the third side, OLED display sheet 214 for the fourth side.

When OLED display sheet 210 for the top surface, OLED display sheet 211 for the first side, OLED display sheet 212 for the second side, OLED display sheet 213 for the third side, and OLED display sheet 214 for the fourth side are described together, they may be described as "each OLED display sheet 210 to 214". In addition, When OLED display sheet 211 for the first side, OLED display sheet 212 for the second side, OLED display sheet 213 for the third side, and OLED display sheet 214 for the fourth side are described collectively, they may be referred to as "each side OLED display sheets 211-214".

Each of these OLED display sheets 210 to 214 is attached one by one to the upper surface 110 and four sides (first side 111, second side 112, third side 113, and fourth side 114) of the wristwatch body 100, i.e., a total of five sides. This constitutes a wristwatch 1 as shown in FIG. 1A and FIG. 1B. In FIG. 1A and FIG. 1B, the analog time display is shown, but when nothing is displayed, the five surfaces of the wristwatch body 100, except for the lower surface, are completely patternless (no pattern). The "no pattern" here means that not only the analog clock display, but also the digital clock display and various other displays are not displayed.

In this case, five OLED display sheets (each OLED display sheet 210 to 214) are attached one by one to the wristwatch body 100 to form the display unit 200. By applying like this, the corners (the corners formed by the top display 210 and the side OLED display sheets 211-214) of the wristwatch 1 can be made a right angled and the flatness of each OLED display sheet 210 to 214 can be made high, therefore it can be made the appearance simple and comfortable.

In addition, the five sides of the wristwatch body 100, i.e., at the upper surface 110 and four sides (first side 111, second side 112, third side 113 and fourth side 114), the first electrode group 120 for supplying electric power and electric signals to each of the OLED display sheets 210 to 214 is exposed and provided. On the other hand, a second electrode group 220 for receiving electric power and electric signals from the first electrode group 120 is provided on the back surface of each of the organic EL display sheets 210 to 214 at a position corresponding to the first electrode group 120. The first electrode group 120 of the wristwatch body 100 and the second electrode group 220 of each of the OLED display sheets 210-214 are electrically connected, the corresponding electrodes being electrically connected. In addition, on the back side of each of the OLED display sheets 210-214, a drive circuit is provided, the drive circuit supplying electrical signals to control the lighting state of each pixel of each OLED display sheet 210 to 214. In addition, in FIG. 2A to FIG. 2C, the drive circuit concerned is omitted.

Figure 3:
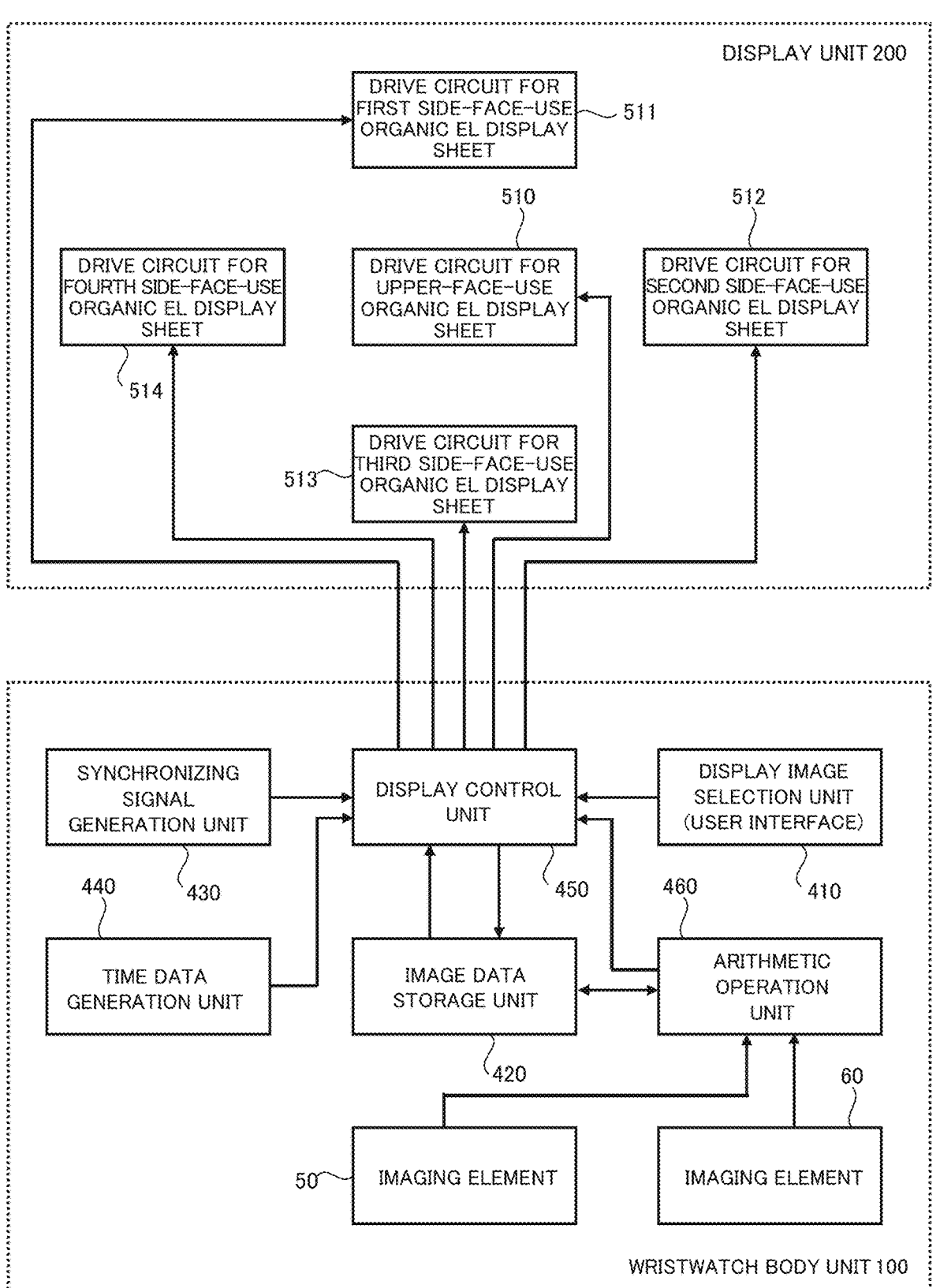

FIG. 3 shows the configuration of the control system for operating the wristwatch 1 according to Embodiment 1. The figure shows the functional block diagram of the wristwatch 1 according to Embodiment 1. The functional block diagram shown in FIG. 3 shows the functional blocks necessary mainly for display among the various functions possessed by the wristwatch 1 in accordance with Embodiment 1.

On the side of the wristwatch body 100, there is a display image selection unit 410 as a user interface that allows the user to select what to display on the five displays 210 to 214 (each OLED display sheet 210 to 214), an image data storage section (unit) 420 that stores images to be displayed on each OLED display sheet 210 to 214, a synchronization signal generation unit 430 that generates synchronization signals to synchronize the images displayed on each OLED display sheet 210 to 214 so that the images to be displayed on each OLED display sheet 210 to 214 are linked or related images, a time data generation unit 440 that generates the current time data, a display control unit 450 for controlling the display of each of the organic EL display sheets 210 to 214, and a calculation unit 460 for identifying the position of the eyes of a human face from the images imaged by the imaging elements 50 and 60 and for identifying the direction from the position of the eyes toward the display 210. The calculation unit 460 is also an example of a detection unit (section). The images to be displayed on each of the OLED display sheets 210-214 may be images stored in the image data storage unit 420, images generated by an image data generator not shown in the figure, or images received from outside via communication. For example, an image from the user's smartphone or images from a contracted video distribution company may be displayed in OLED display sheet 210~214.

On the other hand, on the side of the display unit 200, there are a drive circuit 510 for the OLED display sheet 210 for the top surface, a drive circuit 511 for the OLED display sheet 211 for the first side, a drive circuit 512 for the OLED display sheet 212 for the second side, a drive circuit 513 for the OLED display sheet 213 for the third side and a drive circuit 514 for the OLED display sheet 214 for the fourth side.

Although omitted in FIG. 3, on the side of the wristwatch body 100, a power supply unit is also provided to supply power to each of the functional blocks shown in FIG. 3, and power from the power supply unit and various signals from the display control unit 450 are also supplied through the first electrode group 120 (see FIG. 2A) is provided on the wristwatch body 100 side and the second electrode group 220 (see FIG. 2C) provided on each OLED display sheet 210-214 side, respectively.

The display control unit 450 reads the images stored in the image data storage unit 420 based on the selection selected by the user from the display image selection unit 410, and controls the display of the read images on the respective OLED display sheets 210-214. At this time, the display control unit 450 controls the display of each of the OLED display sheets 210 to 214 so that the images to be displayed on each of the OLED display sheets 210 to 214 are linked or related.

In this way, the display control unit 450 controls the display of images read from the image data storage unit 420 on each of the OLED display sheets 210 to 214. The control is performed to display the display image selection screen that functions as the display image selection unit 410. When the display image selection screen is displayed on the wristwatch 1, the user can select what he/she wants to display from the displayed display image selection screen. The display control unit 450 then controls the display based on the display mode selected by the user. The selection of the display image may be made from the selection screen of the user's smartphone linked to the wristwatch 1.

For example, when the user selects analog time display from the 26 display image selection unit 410, the five displays 210 to 214 of the wristwatch 1 according to Embodiment 1 are in analog clock display mode, and the display control unit 450 reads the current time data from the time data generation unit 440 and controls each OLED display sheets 210 to 214 and controls the respective drive circuits 510 to 514 of each OLED display sheet 210 to 214 to display the current time by the hour and minute hands on the display sheets 210 to 214. The selection of the displayed image can be made from the selection screen of the user's smartphone linked to the wristwatch 1. The specific time display method in the analog time display mode is described below.

At least the display control unit 450 and the arithmetic unit 460, which are components of the control system of the wristwatch body 100, execute the various processes by the operation of a processing unit represented by a CPU (Central Processing Unit: CPU), GPU (Graphics Processing Unit: image processing unit). The various processes are performed, for example, by reading computer programs stored in the memory (ROM, RAM, EEPROM, etc.) in the wristwatch body 100. The image data storage unit 420 is also a memory. The memory storing the computer program may be the image data storage unit 420 or a different memory section. Also. At least one of the various drive circuits 510-514 of the display unit 200 may include a processing unit represented by the CPU or GPU described above.

As explained in FIG. 2A to FIG. 2C, each of the OLED display sheets 210-214 is attached to each of the five surfaces of the six surfaces of the wristwatch body 100, except for the bottom surface. That is, the OLED display sheet 210 for the upper surface is attached to the upper surface 110 of the wristwatch body 100, the OLED display sheet 211 for the first side is attached to the first side 111 of the wristwatch body 100, the OLED display sheet 212 for the second side is attached to the second side 112 of the wristwatch body 100, the OLED display sheet 213 for the third side OLED display sheet 213 for the third side is 28 attached to the third side 113 of the wristwatch body 100, and OLED display sheet 214 for the fourth side is attached to the fourth side 114 of the wristwatch body 100. When each OLED display sheet 210 to 214 is attached to the corresponding side of the wristwatch body 100 in this way, a gap corresponding to the thickness of the OLED display sheet may be generated between adjacent OLED display sheets at the corners of the wristwatch body 100.

Figure 4:
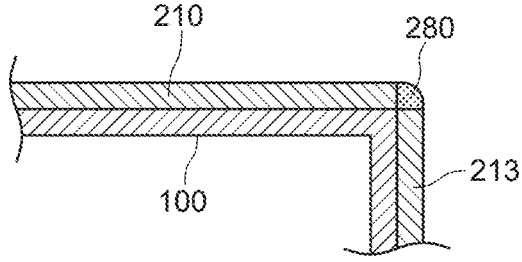

FIG. 4 illustrates how to deal with gaps between adjacent OLED display sheets. FIG. 4 shows for the purpose of FIG. 4 shows an example of a gap between the OLED display sheet 210 for the top surface and the OLED display sheet 213 for the third side.

As shown in FIG. 4, in the corner of the wristwatch body 100, a black member 280 is embedded between adjacent OLED display sheets (in this case, between the OLED display sheet 210 for the top surface and the OLED display sheet 213 for the third side). As the black member 280, for example, silicone rubber mixed with graphite filler to make it black, it can be used as the black member 280. Thus, by filling the gap between adjacent OLED display sheets with the black member 280, the gap between adjacent OLED display sheets becomes less noticeable, and the appearance of the wristwatch 1 becomes neat and pleasing to the eye.

In FIG. 4, only the space between the OLED display sheet 210 for the top surface and the OLED display sheet 213 for the third side is shown, but the gap between the five display sections 210-214, thus, the gap between OLED display sheet 211 for the first side and OLED display sheet 212 for the second side, the gap between OLED display sheet 212 for the second side and OLED display sheet 213 for the third side, the gap between OLED display sheet 213 for the third side and OLED display sheet 214 for the fourth side, and the gap between OLED display sheet 214 for the fourth side and OLED display sheet 211 for the first side, and the gap between the OLED display sheet 210 for the top surface and the OLED display sheets 211 to 214 for each side is also filled with black material 280 in the same way.

Therefore, the black member 280 is buried in the corners of the wristwatch body 100, that is, between adjacent OLED display sheets. On the surface of each of the OLED display sheets 210 to 214 in a state in which the black-colored member 280 is buried between adjacent OLED display sheets, a protective member 290 (see FIG. 6A to FIG. 6C) is applied and cured so as to cover the entire surface of each of said OLED display sheets 210 to 214.

Figure 5:
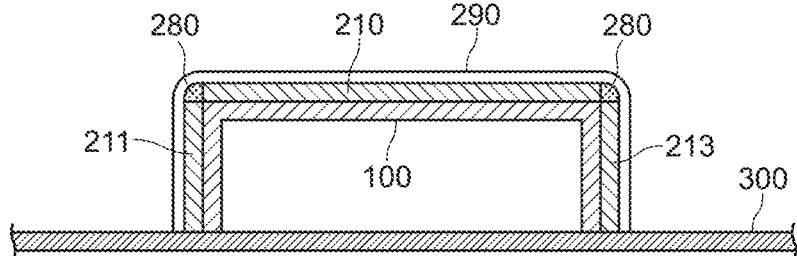

FIG. 5 is a view for describing the state in which protective material 290 is applied and cured to cover the entire wristwatch 1. Note that FIG. 5 is a cross-sectional view of the wristwatch body 100 which is cut vertically from the OLED display sheet 210 for the upper surface to the belt 300 for its lower surface, parallel to the long side of the rectangular wristwatch body 100, and components such as the display control unit 450 that exist inside the wristwatch body 100 (see the functional block diagram in FIG. 3.) are omitted from the figure. As shown in FIG. 5, a transparent protective material 290 is applied and cured so as to cover the entire five display areas of the wristwatch 1, i.e., the OLED display sheet 210 for the top surface and the OLED display sheets 211 to 214 for each first side.

Here, silicone resin or the like having waterproofness, corrosion resistance, and heat resistance can be preferably used as the protective member 290. In this way, by applying and curing the transparent protective member 290 so as to cover the entire five display areas of the wristwatch 1, i.e., the OLED display sheet 210 for the top surface and the OLED display sheets 211 to 214 for each first side, the wristwatch 1 becomes highly reliable because it is waterproof, corrosion resistant, heat resistant, and difficult to be damaged. This makes the wristwatch 1 waterproof, corrosion resistant, heat resistant, and difficult to break.

Note that the five aforementioned display units 210 to 214 may be made up of a single OLED display sheet (not shown in the figure). In such a case, said single OLED display sheet is folded so as to follow the external shape of the wristwatch body 100 and is attached to the wristwatch body 100. When the five display units 210 to 214 consist of a single OLED display sheet, no gap is formed at the folded portion, and therefore, said folded portion does not need to be filled with black material. On the other hand, a gap equivalent to the thickness of the OLED display sheet may be formed at the border between adjacent OLED display sheets, not at the folded sections.

For example, in a single OLED display sheet of such a shape that the OLED display sheet for the first side, the OLED display sheet for the second side, the OLED display sheet for the third side, and the OLED display sheet for the fourth side respectively extend in all directions, by attaching the OLED display sheet for the upper side to the top surface to the top surface 110 of the wristwatch body 100 and bending the OLED display sheet for each side, the OLED display sheet for each side can be attached to each side 111-114 of the OLED display sheet. In this case, since a gap equivalent to the thickness of the OLED display sheet may be formed at the corner of each side display, it is preferable to fill the gap with a black material.

Next, the specific display style of the wristwatch 1 according to Embodiment 1 will be explained. Although the wristwatch 1 according to Embodiment 1 can be worn on either the left or right arm of the user, we will now describe the case where the wristwatch 1 according to Embodiment 1 is worn on the wrist of the user's left arm, as shown in FIG. 1.

[First Display Mode]

Assume that the user selects the digital watch display mode from the display image selection unit 410. In this case, five display units 210 to 214 perform a digital display in a digital watch display mode where a time is displayed by numerals and the present time is displayed on five display units 210 to 214 of the wristwatch 1. In this display mode, as the time display mode, a case is exemplified where each of the hour and the minute is displayed by numerals of two digits.

Figures 6A, 6B, 6C:
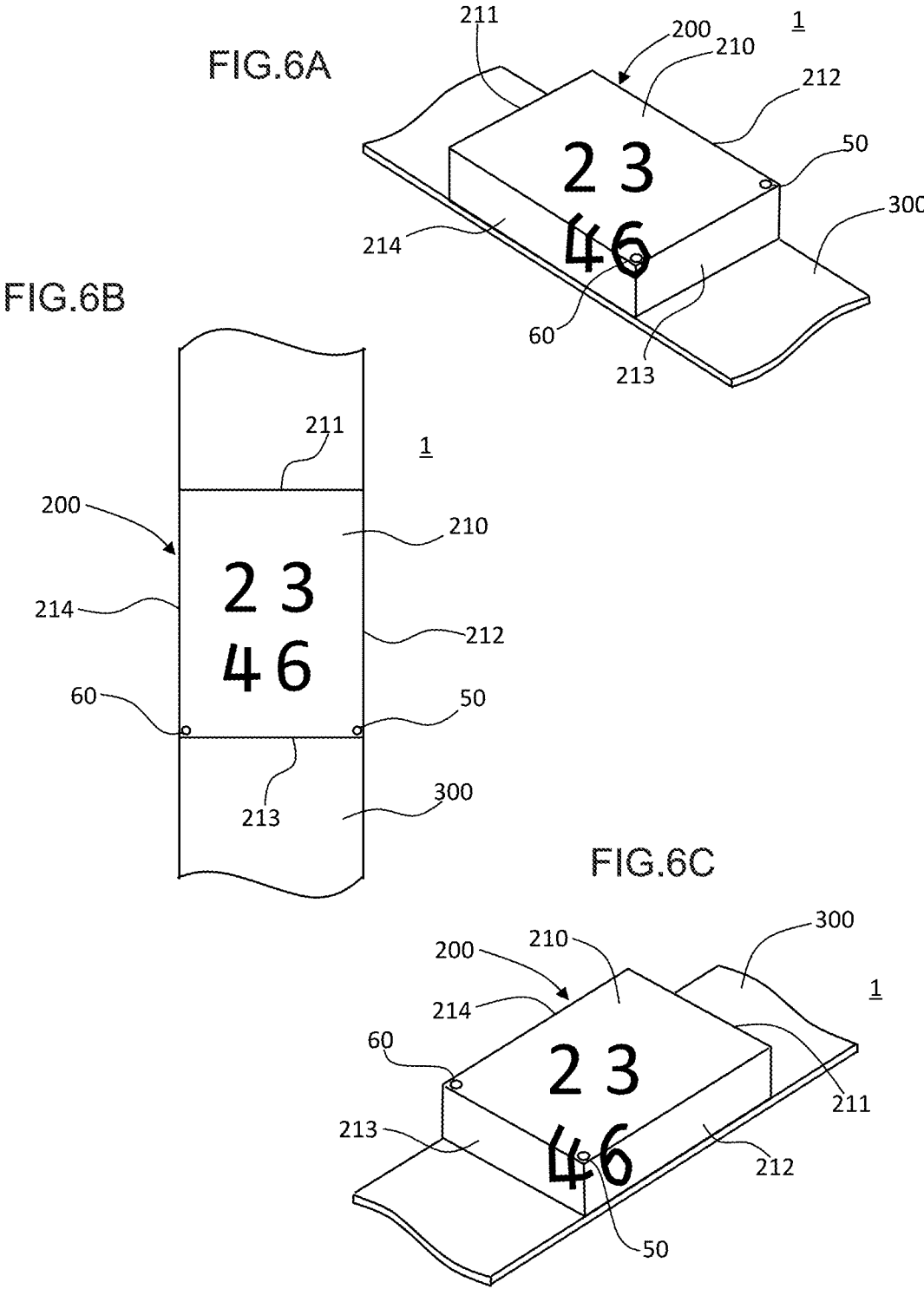

FIG. 6A to FIG. 6C are views for describing the first display mode of the wristwatch 1 according to the embodiment 1. For example, as illustrated in FIG. 6A to FIG. 6C, assume that twenty-three forty-six is displayed as the present time. FIG. 6A indicates the time display when the wristwatch body 100 is viewed obliquely from above the wristwatch body 100 at a position close to the imaging element 60. FIG. 6B indicates the time display when the wristwatch body 100 is viewed from above and perpendicular to a face of the upper-face-use organic EL display sheet 210 of the wristwatch body 100. FIG. 6C indicates the time display when the wristwatch body 100 is viewed obliquely from above the wristwatch body 100 at a position close to the imaging element 50.

In all time display cases illustrated in FIG. 6A, FIG. 6B and FIG. 6C, four numerals that indicate twenty-third forty-six are displayed on at least one of display units 210 to 214 such that these numerals are directed toward the user as much as possible.

In all time display cases illustrated in FIG. 6A, FIG. 6B and FIG. 6C, four numerals that indicate twenty three forty six are displayed on at least one display units out of the display units 210 to 214 such that four numerals are directed to the user within a movable range.

For example, in the example illustrated in FIG. 6A, the time is displayed such that the display units 210, 213, 214 face the line of sight of the user in a face-to-face manner at the position obliquely from above the wristwatch body 100 and close to the imaging element 60. Actually, in the wristwatch body 100, faces formed on the display units 210, 213, 214 are not formed of a flat face. Accordingly, the numerals that are displayed in a straddling manner over two or three display units are displayed in a bent manner at sides or corners of the display units. In FIG. 6A, the numeral "4" is displayed in a straddling manner over the display unit 210 and the display unit 214. Further, the numeral "6" is displayed in a straddling manner over the display unit 210, the display unit 213, and the display unit 214. Accordingly, numerals "4", "6" are displayed in a bent manner at the sides of the display units that are brought into contact with each other.

In the example illustrated in FIG. 6B, the display of time is performed such that only the display unit 210 faces the line of sight of the user in a face-to-face manner at the position above the wristwatch body 100 perpendicular to the upper surface of the wristwatch body 100. Time is displayed only on the display unit 210 and hence, four numerals having no bending are displayed on the display unit 210.

In the example illustrated in FIG. 6C, the display of time is performed such that the display units 210, 212, 213 face the line of sight of the user in the direction close to the imaging element 50 when the wristwatch body 100 is viewed obliquely from above the wristwatch body 100. Actually, in the wristwatch body 100, faces formed on the display units 210, 212, 213 are not formed of a flat face. Accordingly, the numerals that are displayed in a straddling manner over two display units are displayed in a bent manner at sides or corners of the display units.

In FIG. 6C, the numeral "4" is displayed in a straddling manner over the display unit 210, the display unit 212 and the display unit 213. Further, the numeral "6" is displayed in a straddling manner over the display unit 210 and the display unit 212. Accordingly, numerals "4", "6" are displayed in a bent manner at the corresponding sides of the display units.

As described, to realize the face-to-face display with respect to the line of sight of the user, processing such as imaging of an image that includes eyes of the user by the imaging elements 50, 60, the recognition of the image by the arithmetic operation unit 460 and the like are performed. The detail of the above-mentioned processing is described later.

[Second Display Mode]

Next, the second display mode is described. Assume that the user selects an analog watch display mode from the display image selection unit 410. Accordingly, five display units 210 to 214 indicate an outer edge portion of the watch, four numerals in total indicating 12 o'clock, 3 o'clock, 6 o'clock, and 9 o'clock, a short hand (hour hand) and a long hand (minute hand).

Figures 7A, 7B, 7C:
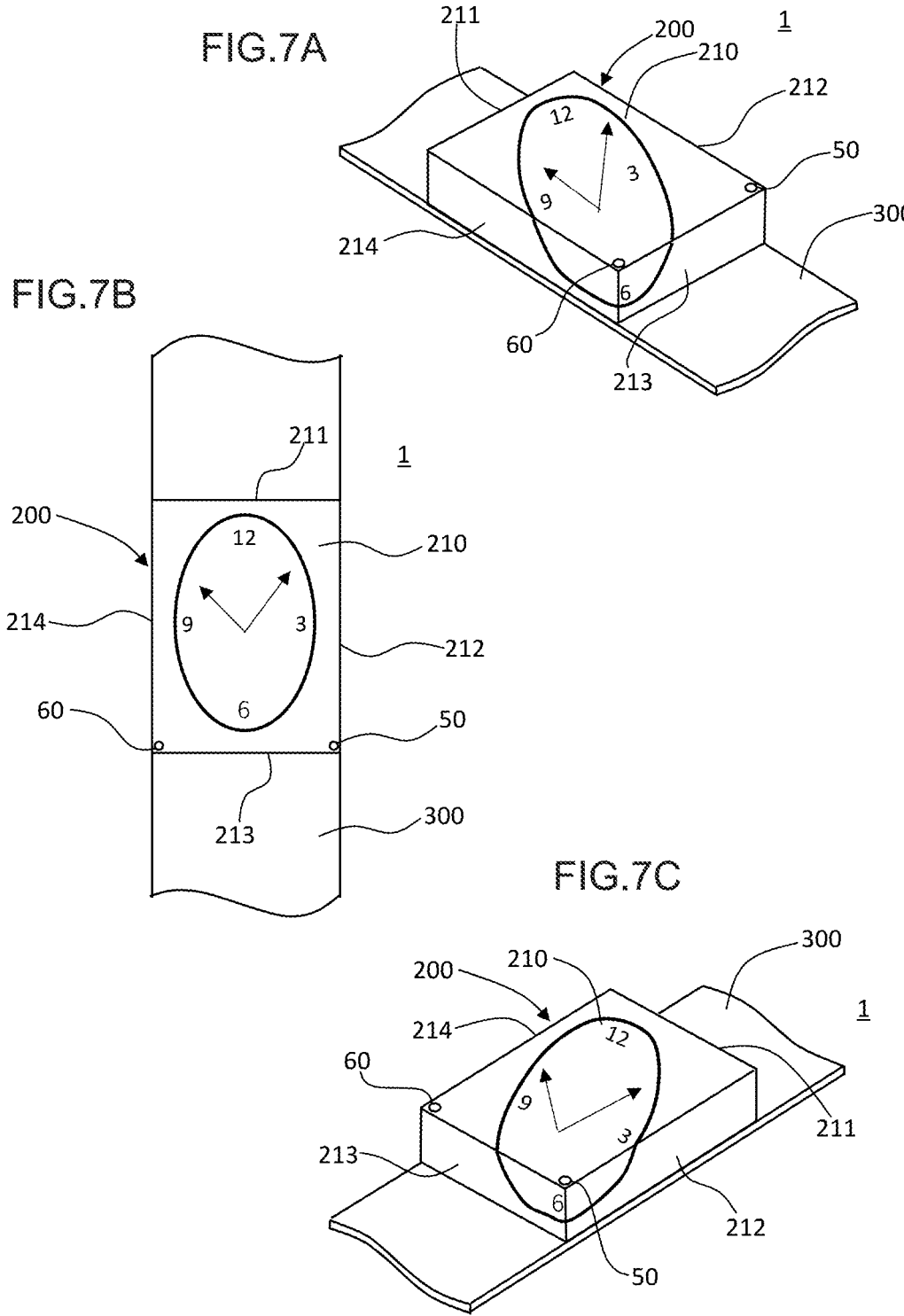

FIG. 7A to FIG. 7C are views for describing a second display mode according to the wristwatch 1 of the embodiment 1. For example, as illustrated in FIG. 7A to FIG. 7C, assume that ten ten (10:10) is displayed as the present time. FIG. 7A indicates a time display when the wristwatch body 100 is viewed from above the wristwatch body 100 obliquely at a position close to the imaging element 60. FIG. 7B indicates the time display when the wristwatch body 100 is viewed from above the wristwatch body 100 perpendicular to the face of the upper-face-use organic EL display sheet 210 of the wristwatch body 100. FIG. 7C indicates the time display when the wristwatch body 100 is viewed from above the wristwatch body 100 obliquely at a position close to the imaging element 50.

In all time display cases illustrated in FIG. 7A, FIG. 7B and FIG. 7C, the display of the analog watch indicating ten ten is displayed in at least one display unit out of the display units 210 to 214 such that the display is directed toward the user as much as possible.

For example, in the example illustrated in FIG. 7A, the display of the analog watch is performed such that the display units 210, 213, 214 face the line of sight of the user in a face-to-face manner above the wristwatch body 100 obliquely at the position close to the imaging element 60. In an actual wristwatch body, faces formed of the display units 210, 213, 214 are not formed of a flat face. Accordingly, the display of the analog watch is performed in a bent state on sides that become boundaries between the respective display units 210, 213, 214. In FIG. 7A, a portion of a lower area of the analog watch is displayed on the display unit 213 and the display unit 214.

In the example illustrated in FIG. 7B, only on the display unit 210, the display of the analog watch is performed such that the display of the analog watch faces the line of sight of the user above the wristwatch body 100 perpendicular to the upper surface of the wristwatch body 100. The analog watch is displayed only on the display unit 210 and hence, the analog watch is displayed on the display unit 210 in a state where the display of the analog watch is not bent.

In the example illustrated in FIG. 7C, the display of the analog watch is performed such that the display units 210, 212, 213 face the line of sight of the user in a face-to-face manner above the wristwatch body 100 obliquely at a position close to the imaging element. Actually, in the wristwatch body 100, faces formed on the display units 210, 212, 213 are not formed of a flat face. Accordingly, the display of the analog watch is displayed in a state where the display of the analog watch is bent on sides that become boundaries between the respective display units 210, 212, 213. In FIG. 7C, a portion of lower area of the analog watch is displayed on both the display unit 212 and the display unit 213.

As described above, to make the analog watch face toward the user in a face-to-face display manner, processing such as imaging of images including eyes of the user by the imaging elements 50, 60 and the recognition of images by the arithmetic operation unit 460 can be performed. The detail of the above-mentioned processing is described later.

[Third Display Mode]

Figures 8A, 8B, 8C:
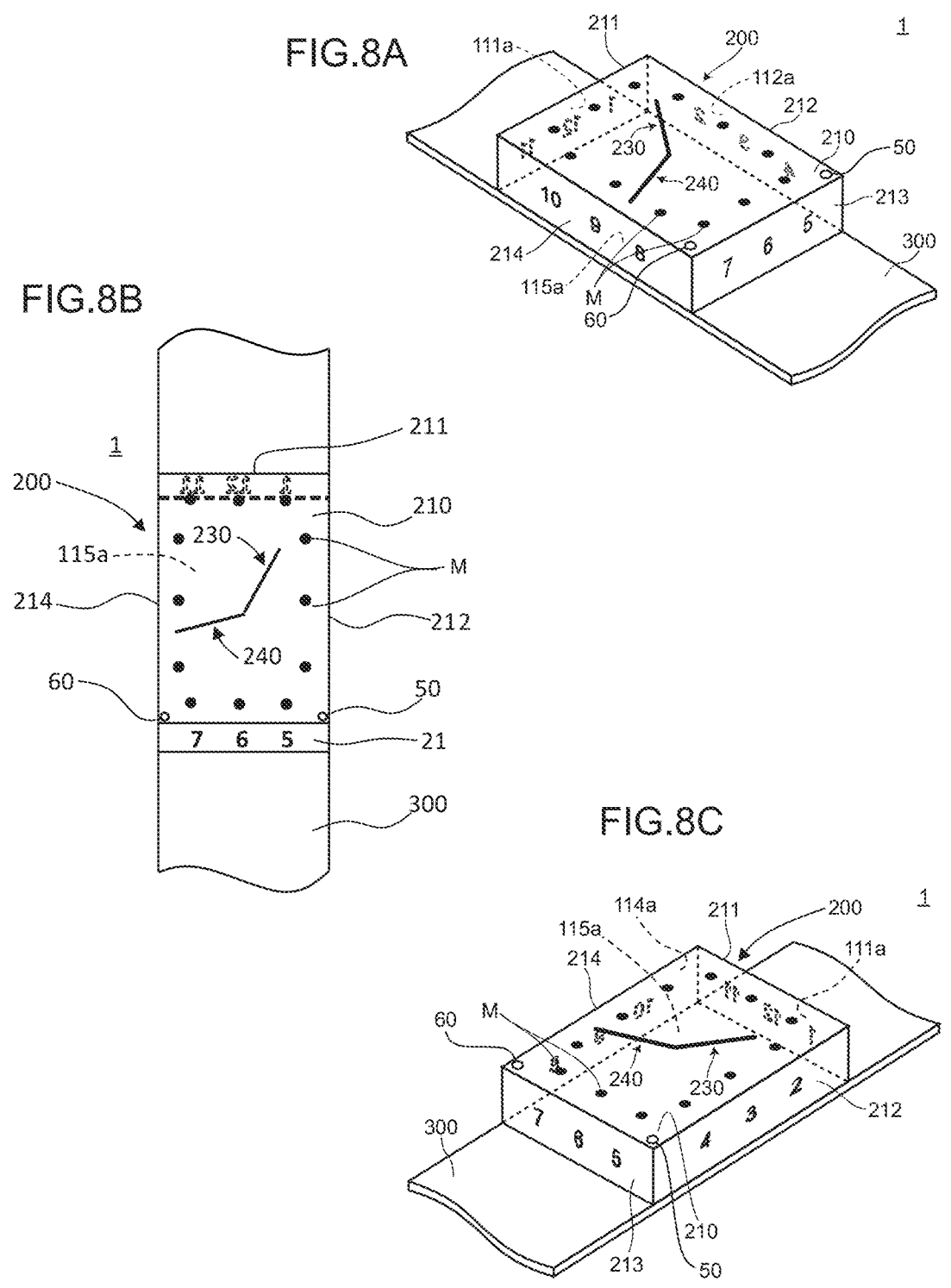

Next, the third display mode is described. FIG. 8A to FIG. 8C are views for describing the third display mode according to the wristwatch 1 of the embodiment.

The third display mode of the wristwatch 1 according to the embodiment is also, in the same manner as the above-mentioned second display mode, a mode in a case where five display units 210 to 214 are set in an analog watch display mode. However, in the third display mode, unlike the above-mentioned second display mode, numerals that indicate the time is formed of twelve kinds of numerals from "1" to "12", and these numerals are displayed on each of side-face-use organic EL display sheets 211 to 214 that are respective side faces of the wristwatch body 100. Further, the display unit 210 displays dots (indicated by M in FIG. 8) that correspond to twelve kinds of numerals displaying the time on an elliptical or rectangular periphery of the wristwatch body 100, and the hour hand 230 and the minute hand 240 are displayed in the inside of the wristwatch body 100. In the third display mode, the time is one forty three.

In the third display mode of the wristwatch 1 according to the embodiment 1, the display control unit 450 performs a control as if the inside of the wristwatch body 100 is viewed in a see-through manner as viewed from a user, and numerals that indicate the time in the analog watch display mode are displayed on the side face display units 211 to 214. In such a control, the display control unit 450 performs display processing such that the numerals that indicate the time are displayed in a reverse left and right display as if the numerals in a reverse left and right display pass through the inside of the wristwatch body 100 in a see-through manner. In the third display mode, unlike the first display mode and the second display mode, the display mode where the display of the time or the watch faces the user in a face-to-face manner is not performed, and the numerals that shouldn't be viewed from the user are displayed in a see-through manner using the side faces that are viewed from the user. Accordingly, it may be safe to say that such a display is a display where a three-dimensional image appears in a portion of the wristwatch body 100.

The display control where the respective organic EL display sheets 210 to 214 are viewed in a see-through manner in the inside of the wristwatch body 100 means that the display control is performed as if the wristwatch body 100 is a transparent vessel. For example, according to the display mode illustrated in FIG. 8A, the display control is performed such that the user can visually recognize each of the side faces in the inside of the wristwatch body 100 (a surface 111*a* on an inner side of the first side face 211 and a surface 112*a* on an inner side of the second side face 212), and an inner bottom surface 115*a* of the wristwatch body 100 can be visually recognized as viewed from the user. In this case, "transparent vessel" may be a non-colored transparent vessel or a colored transparent vessel that has light transmissivity.

By performing such a display control, as viewed from the user, the display control unit 450 performs a control as if the inside of the wristwatch body 100 appears in a see-through manner. Particularly, in the case of the display mode in FIG. 8A, "11", "12", "1" and "2", "3", "4" that are displayed on the first side face display unit 211 and the second side face display unit 212 that are originally not viewed from the user are displayed individually in a reverse left and right display as viewed from the user. Accordingly, the user has a feeling as if the wristwatch body 100 is a transparent vessel and the inside of the wristwatch body 100 appears in a see-through manner.

Further, in the third display mode, the hour hand 230 and the minute hand 240 are displayed on the upper face display unit 210 as if the upper face display unit 210 is transparent as viewed from the user. In this case, the minute hand 240 is displayed only on the upper face display unit 210. However, the minute hand 240 may be displayed in an extending manner over one side face display unit out of the side face display units 211 to 214.

The display mode illustrated in FIG. 8A illustrates the time display when the wristwatch body 100 is viewed from above the wristwatch body 100 obliquely at a position close to the imaging element 60. Such a display mode can be realized because the direction from which the user is viewing the wristwatch body 100 is specified. Accordingly, using the imaging elements 50, 60 and the arithmetic operation unit 460, it is possible to perform processing such as imaging of an image that includes eyes of a user, the recognition of the image and the like. Due to such processing, the sides of the wristwatch body 100 that cannot be viewed from the user can be specified, and a see-through display of the sides can be displayed in a pseudo manner on the upper face and the side faces that are actually viewed from the user.

FIG. 8B is the time display when the wristwatch body 100 is viewed from above the wristwatch body 100 at a position slightly obliquely inclined rearward along the belt 300 with respect to a face of the upper-face-use organic EL display unit 210 of the wristwatch body 100. In this case, it is necessary to perform display processing of the display unit 210 such that the side face display unit 211 is viewed in a pseudo see-through manner. On the other hand, the side face display unit 213 is viewed by the user and hence, it is sufficient to adopt a usual display mode. Since the side face display units 212, 214 cannot be viewed at all from the user, it is unnecessary to perform any display processing. Such a display can be realized by using the imaging elements 50, 60 and the arithmetic operation unit 460 in the same manner as the case illustrated in FIG. 8A.

The display mode illustrated in FIG. 8C illustrates the time display when the wristwatch body 100 is viewed from above the wristwatch body 100 obliquely at a position close to the imaging element 50. According to the display mode illustrated in FIG. 8C, the display control unit 450 performs a display control of the display units 210, 212, 213 such that the user can visually recognize side faces in the inside of the wristwatch body 100 (the surface 111*a* on the inner side of the first side face 211 and the surface 114*a* on the inner side of the fourth side face 214) in a see-through manner, and the inner bottom surface 115*a* of the wristwatch body 100 can be also viewed in a see-through manner from the user. Such a display can be realized using the imaging elements 50, 60 and the arithmetic operation unit 460 in the same manner as the case illustrated in FIG. 8A.

In this manner, in the third display mode, the display control unit 450 performs a control as if the inside of the wristwatch body 100 is viewed in a see-through manner as viewed from the user, and the display of numerical values that indicate a time in an analogue watch display mode is performed in a normal left and right display on the side faces that are viewed from the user and in a reverse left and right display on the side faces that are not viewed from the user by using faces that are viewed from the user. Accordingly, the wristwatch 1 according to the embodiment 1 becomes a wristwatch having a new value not obtained by the prior art. With respect to the side faces that are not viewed from the user, it may be possible to prevent such side faces from displaying numeral values that indicate a time in the analog watch display mode and other displays. However, to prevent a person other than the user from having a discomfort when the person views the wristwatch, the display of the numerical values that indicate the hour time may be displayed in a normal left and right display as viewed from the person other than the user. The detail of the above-mentioned processing is described later.

[Fourth Display Mode]

FIG. 9A to FIG. 9C are views for describing the fourth display mode of the wristwatch 1 according to the embodiment 1. The fourth display mode is a mode where five display units 210 to 214 are set in a digital watch display mode. In this digital display mode, the digital watch display mode is not a mode where the time is indicated by the hour hand and the minute hand, but, in the same manner as the first display mode, is a display mode where the time is displayed by numerical values. Further, in the fourth display mode, an example is described where only the time but also other information such as date and the day of the week are displayed. In making the wristwatch 1 perform such a display, for example, the user can set five display units 210 to 214 in a digital watch display mode by selecting "digital watch display", for example, from a display image selection screen that functions as the display image selection unit 410.

By setting five display units 210 to 214 in a digital watch display mode, for example, as illustrated in FIG. 9, on the upper face display unit 210, for example, besides displaying the present time of ten, twenty five, thirty four as "10:25:34", the date of today such as Oct. 1, 2020 is displayed as "20. 10. 01", and today is displayed as "Thursday" as the day of the week. Further, as other information, for example, a weather forecast of today is displayed on each of side face display units 211 to 214 (the side face display units 214, 213, 212 in the example illustrated in FIG. 9A to FIG. 9C) by a weather mark or the like. The various information may be displayed in a streaming manner on each of the display units. As an example, the day of the week can be displayed in a streaming manner, and various information are displayed one after another following the day of the week.

Unlike the first display mode, the fourth display mode is not a mode where the time and the like that face the user in a face-to-face manner are displayed. The fourth display mode is a mode where the display mode is rotated at a unit of 90 degrees in plane on the display unit 210 so as to enable the user to view the display of time and the like in a horizontal state as much as possible, and the display of the weather is displayed on the side surface positioned just below the display surface for displaying the time and the like.

FIG. 9A illustrates the time display when the wristwatch body 100 is viewed from above the wristwatch body 100 obliquely at position close to the imaging element 60. Such a display mode can be realized because the direction from which the user views the wristwatch body 100 specified. Accordingly, using the imaging elements 50, 60 and the arithmetic operation unit 460, it is possible to perform processing such as imaging of an image that includes eyes of a user, the recognition of the image and the like. As a result, with respect to the line of sight of the user, the display of the time and the like is performed such that the display becomes approximately parallel to a long side of the display unit 210 having a rectangular shape, and the display can be normally visually recognized without becoming upside down. This is because the user can more easily view the display parallel to the long side compared to display parallel to the short side. The weather is displayed on the display unit 214 positioned just below the display of the time and the like on the display unit 210. In a case where the wristwatch body 100 is viewed from above the wristwatch body 100 obliquely at the position close to the imaging element 60, the display control unit 450 specifies the direction of the line of sight along which the user views the display unit 210 of the wristwatch 1 by making use of the imaging elements 50, 60 and the arithmetic operation unit 460, and determines the display mode of the time and the like on the display units 210 to 214. The detail of this processing is described later.

FIG. 9B illustrates the time display when the wristwatch body 100 is viewed from above the wristwatch body 100 at a position slightly obliquely inclined rearwardly along the belt 300 with respect to a face of the upper-face-use organic EL display sheet 210 of the wristwatch body 100. In this case, in the display unit 210 having a rectangular shape, displaying of the time and the like is performed approximately parallel to a short side of the display unit 210. The processing performed by the display control unit 450 and the like is performed substantially in the same manner as the case illustrated in FIG. 9A.

FIG. 9C illustrates the time display when the wristwatch body 100 is viewed from above the wristwatch body 100 obliquely at a position close to the imaging element 50. In the same manner as the case illustrated in FIG. 9A and FIG. 9B, imaging of an image including eyes of a person, the recognition of an image and the like are performed using the imaging elements 50, 60 and the arithmetic operation unit 460. As a result, with respect to the line of sight of the user, the display of the time and the like is performed such that the display becomes approximately parallel to a long side of the display unit 210 having a rectangular shape, and the display can be normally visually recognized without becoming upside down. The weather is displayed on the display unit 212 positioned just below the display of the time and the like on the display unit 210. In a case where the wristwatch body 100 is viewed from above the wristwatch body 100 obliquely at the position close to the imaging element 50, the display control unit 450 specifies the direction of the line of sight along which the user views the display unit 210 of the wristwatch 1 by making use of the imaging elements 50, 60 and the arithmetic operation unit 460, and determines the display mode of the time and the like on the display units 210 to 214. The detail of the above-mentioned processing is described later.

In this manner, in the fourth display mode, various information including the digital watch display can be displayed as images using five display units 211 to 214, and some information (images) or all information (images) can be displayed in a streaming manner. As described above, the wristwatch 1 according to the embodiment 1 can realize the image display that corresponds to the line of sight of the user and hence, it is possible to provide the wristwatch having a new value not obtained by the prior art.

[Method for Specifying Direction Along which User Views Wristwatch]

Next, a method of specifying the direction along which a user of the wristwatch 1 according to the embodiment 1 views.

FIG. 10A to FIG. 10C are views for describing the method for specifying the direction along which the user of the wristwatch 1 according to the embodiment 1 views the wristwatch 1. In the wristwatch 1 according to the embodiment 1, a distance between the eyes of the user and the in-plane center of the display unit 210 of the wristwatch is specified using two imaging elements 50, 60 and the arithmetic operation unit 460.

Hereinafter, the method for specifying the distance between the eyes of the user and the in-plane center of the display unit 210 of the wristwatch using two imaging elements 50, 60 is described. FIG. 10A illustrates a three-dimensional space where the display face 210 is set as an XY plane and the direction perpendicular to the display face 210 is set as a Z axis using the imaging element 60 (set as a point A) as an origin. Assume that the imaging element 50 (set as a point B) exists on an X axis. When the imaging element 60 images the user, the arithmetic operation unit 460 can recognize both eyes from an image of the user. To be more specific, the arithmetic operation unit 460 recognizes a face of a person in the image and the position of the eyes of the person by making use of a learned model in the image data storage unit 420. As a result, in the three-dimensional space, the direction D2 toward a middle point M of a line segment that connects both eyes of the user from the point A of the imaging element 60 is specified. It must be noted that only the direction D2 can be specified from the image imaged by the imaging element 60.

Next, when the imaging element 50 images the user, in the same manner as the imaging performed by the imaging element 60, the arithmetic operation unit 460 can recognize both eyes from the image of the user. With respect to the utilization of a learned model, the learned model is used substantially in the same manner as the learned model utilized for analyzing the image that is imaged using the imaging element 60. As a result, in the three-dimensional space, a direction D3 directed toward a middle point M of a line segment that connects both eyes of the user from the point B of the imaging element 60 is specified. When two directions consisting of the direction D2 and the direction D3 are specified, the arithmetic operation unit 460 determines the coordinates of the point M at which these directions intersect with each other. A distance between the point A and the point B corresponds to a length of the short side of the display unit 210. Since a distance L2 between the point A and the point M, a distance L3 between the point B and the point M, and the directions D1, D2 are also specified, a triangle ABM that is inclined from the display unit 210 at a certain angle can be specified.

FIG. 10 (b) is a view for describing the direction along which the middle point M of the line segment that connects both eyes of the user and the center C of the display unit 210 are connected to each other and the distance between the middle point M and the center C. FIG. 10C is a view as viewed from the position close to the wristwatch 1 by omitting the wristwatch 1 from FIG. 10B. When the triangle ABM and an angle θ that is made between the triangle ABM and the display unit 210 are specified, a direction D4 that is directed toward the center C of the display unit 210 from the point M and a distance L4 between the point M and the center C are also unequivocally determined. This is because that the positional relationship between the center C and the point A (or the point B) is fixed. The above-mentioned calculation is performed by the arithmetic operation unit 460. When the direction directed to the center C of the display unit 210 from the middle point M and the distance between the middle point M and the center C are determined in this manner, the display control unit 450 of the wristwatch 1 transmits signals to the drive circuits 510 to 514 so as to realize a display corresponding to the direction of the line of sight from the user.

In performing the above-mentioned display control by the display control unit 450, the distance L4 between the middle point M and the center C is not indispensable. It is sufficient that only the direction D4 that is directed toward the center C of the display unit 210 from the point M is specified. However, by specifying the distance L4, the following advantageous effect can be acquired. In the case where the distance L4 exceeds a certain threshold (for example, 800 mm), the wristwatch 1 maintains a black state without performing the display of the wristwatch 1. On the other hand, in the case where the distance L4 is equal to or less than the above-mentioned threshold (for example, 800 mm), the display control unit 450 can perform a control such that the display of the time and the like can be performed on the display units 210 to 240 of the wristwatch 1. The reason that such a control is performed is that, it is necessary to make the wristwatch 1 not perform the display of the time and the like in the case where a person who stands near the wristwatch 1 by an accident casts his/her line of sight to the wristwatch 1 when the wristwatch 1 is placed on a desk, and to make the wristwatch 1 perform the display of the time and the like only in the case where the user who wears the wristwatch 1 on his/her wrist views the wristwatch 1. The above-mentioned threshold is not limited to 800 mm and, for example, the threshold can be set to different distances such as 500 mm or 1200 mm, for example. The threshold may be stored in the image data storage unit 420, for example. The display control unit 450 or the arithmetic operation unit 460 can read the threshold stored in the image data storage unit 420, and can compare the read threshold with the distance L4 between the middle point M and the center C. The user may not be allowed to set the threshold. Alternatively, the user can freely set the threshold by making use of a setting means such as the display image selection unit 410.

In addition to the above-mentioned processing, instead of performing the changeover between the display and the non-display on the display units 210 to 214 based on the size of the distance L4, the changeover between the display and the non-display may be performed based on the distance L2 from the imaging element 60 to the middle point M, the distance L3 from the imaging element 50 to the middle point M, or a sum of the distance L2 and the distance L3. Further, in place of the middle point M, a position E1 of the eye or a position E2 of the eye may be used. As a modification, in a case where only one eye is detected from the image of the user, the instead of specifying the coordinates of the middle point M, the position (for example, E2) of the detected one eye may be specified and, then, a triangle ABE2 (including an angle θ made by the triangle ABE2 and the display unit 210) may be specified.

The above-mentioned embodiment is an embodiment of the wristwatch 1 having the detection unit that includes two imaging elements 50, 60. However, the number of the imaging elements is not limited to two. For example, in the wristwatch 1 according to a modification, the detection unit may include: one or more imaging elements mounted on any desired portions of the wristwatch 1; and an arithmetic operation unit that extracts information relating to the positional relationship between the eyes of the user of the wristwatch 1 and the wristwatch 1 from the image of the eyes of the user of the wristwatch 1 imaged by one or more imaging elements. As a result, the arithmetic operation unit can extract, as the positional information of the wristwatch 1, information relating to the positional relationship between the eyes of the user of the wristwatch 1 and the wristwatch 1. For example, in the wristwatch 1 that includes only one imaging element, although the direction that is directed from the eyes of the user to a predetermined position of the upper face display unit 210 of the wristwatch 1 (as an example, the center of the upper face display unit 210) can be specified, the distance between the eyes of the user and the predetermined position of the upper face display unit 210 cannot be specified. However, so long as the above-mentioned direction can be specified, the directions of the images displayed on the display units 210 to 214 can be determined corresponding to the above-mentioned direction. On the other hand, in the case where the wristwatch 1 includes three or more imaging elements, the direction directed toward the predetermined position on the upper face display unit 210 from the eyes of the user and the distance between the predetermined position and the eyes of the user can be more accurately specified compared to the example where the above-mentioned two imaging elements 50, 60 are used.

One or more imaging elements may be four imaging elements. Four imaging elements may preferably be disposed in the vicinity of vertexes where side faces arranged adjacently to each other out of four side faces of the wristwatch 1 and the upper face of the wristwatch 1 are brought into contact with each other. By arranging four imaging elements at such positions, in the case where the eyes of the user exist in the direction along which imaging by the above-mentioned imaging elements 50, 60 is difficult, the position of such eyes can be easily imaged using two imaging elements other than the imaging elements 50, 60. Further, as a modification, four imaging elements may be arranged on only the belt 300 that is connected to the wristwatch 1, or two imaging elements may be arranged at each of connecting portions between the wristwatch body 100 and the belt 300. Further, one imaging element is arranged at each of three corners out of four corners of the upper face display unit 210. Although a complementary level of imaging is lowered compared to the case where one imaging elements is arranged at each of all four corners, the complementary level becomes higher compared to the case where two imaging elements 50, 60 are arranged. Further, two imaging elements out of three imaging elements may be arranged at two corners of the upper face display unit 210, and the remaining one imaging element may be arranged at the connecting portion between the wristwatch body 100 and the belt 300.

EMBODIMENT 2

Next, the embodiment 2 of the present invention is described. In the embodiment 2, constitutional components substantially equal to the corresponding components of the embodiment 1 are given the same symbols, and there may be a case where the description of the constitutional components is omitted.

Figure 11:
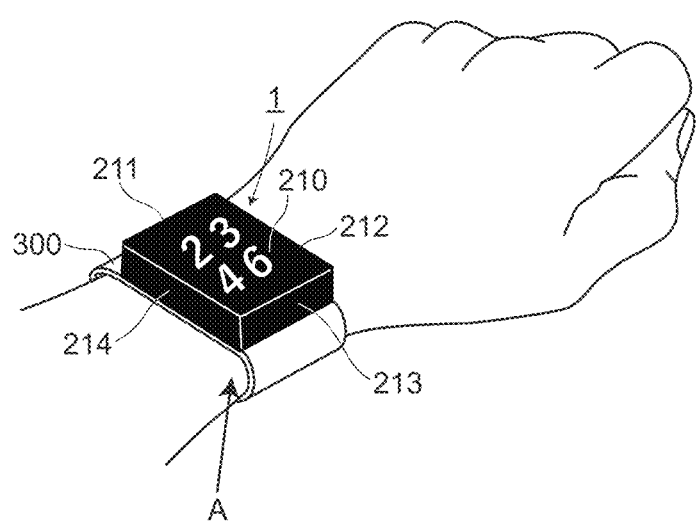

FIG. 11 is a view illustrating a state where the wristwatch 1 according to the embodiment 2 is mounted on a left arm of a user. In FIG. 11, in the same manner as the embodiment 1, an arrow A indicates the direction of the line of sight when the user views the wristwatch 1 that the user wears on the wrist of his/her left arm. In FIG. 11, although the arrow A indicates the direction on a horizontal plane, in general, the actual direction of the line of sight is directed obliquely in the downward direction as viewed from the eyes of the user.

In the wristwatch 1 according to the embodiment 2, the display units 210 to 214 become black in a non-display state, and the display units 210 to 214 perform the digital watch display in a display mode. In the example illustrated in FIG. 11, four numerals in total consisting of the numeral "2", the numeral "3", the numeral "4" and the numeral "6" that indicate twenty three forty six are displayed only on the display unit 210.

Figure 12:
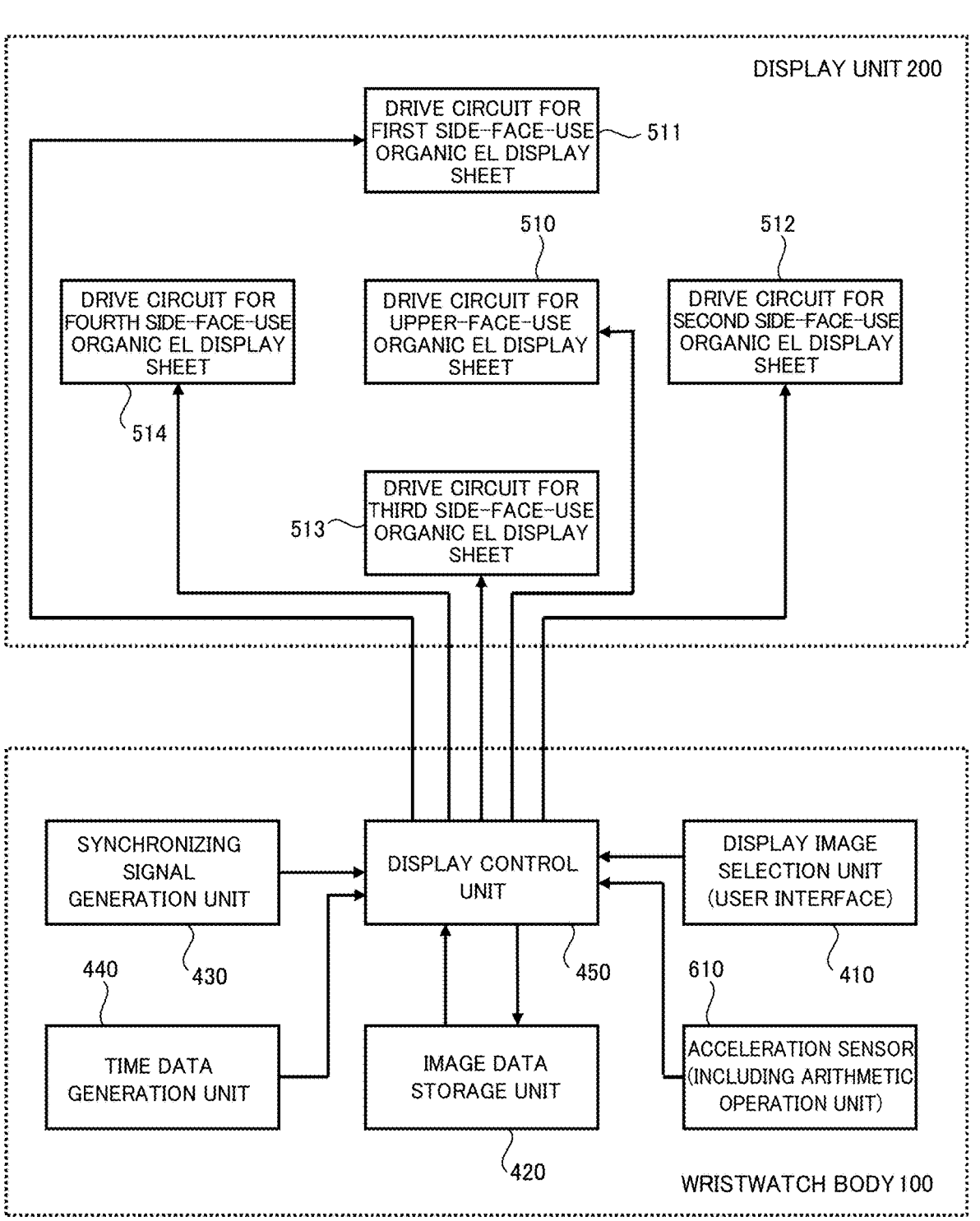

FIG. 12 is a view illustrating the configuration of a control system for operating the wristwatch 1 according to the embodiment 2 as a functional block diagram. The functional block diagram illustrated in FIG. 12 mainly illustrates functional blocks necessary for performing the display out of various functions that the wristwatch 1 according to the embodiment 2 has. A detection unit provided to the wristwatch 1 according to the embodiment 2 includes a three-dimensional acceleration sensor that detects the posture information of the wristwatch 1, and can detect information relating to the three-dimensional posture of the wristwatch 1 as the posture information of the wristwatch 1. Further, the detection unit also functions as a three-dimensional acceleration sensor that detects the movement information of the wristwatch 1, and can detect information relating to the three-dimensional movement of the wristwatch 1 as the movement information of the wristwatch 1. Hereinafter, with reference to FIG. 12, the functions peculiar to the embodiment 2 are described, and the repeated description of the functions substantially equal to the corresponding functions in the embodiment 1 is omitted.

The wristwatch body 100 includes, in the same manner as the embodiment 1, various constitutional units consisting of a display image selection unit 410, an image data storage unit 420, a synchronizing signal generation unit 430, a time data generation unit 440, and a display control unit 450. In addition to these various constitutional units, the wristwatch body 100 includes a three-dimensional acceleration sensor (hereinafter simply referred to as "acceleration sensor") 610. The respective constitutional units of the display unit 200 are substantially equal to the corresponding constitutional units of the embodiment 1. The acceleration sensor 610 is a kind of an inertia sensor capable of measuring the acceleration, and can detect the three-dimensional inertia movement. The acceleration sensor 610 can detect the movement of the wristwatch 1 corresponding to the movement of the arm of the user, and also can detect whether or not the display unit 210 of the wristwatch 1 maintains the horizontal or an angle close to the horizontal. In this embodiment, the acceleration sensor 610 also includes an arithmetic operation unit. The arithmetic operation unit is a unit that performs an arithmetic operation using a processor such as a CPU or a GPU. The "arithmetic operation units" described hereinafter are each substantially formed of the same unit that performs an arithmetic operation using a processor such as a CPU or a GPU. The wristwatch body 100 may include a device that is formed by integrating the acceleration sensor 610 and a gyro sensor with each other. Further, the wristwatch body 100 may further include a geomagnetic sensor. The image data storage unit 420 stores a threshold of acceleration and various computer programs besides various image data. The display control unit 450 looks up the above-mentioned threshold in the image data storage unit 420, and can change over the display on the display units 210 to 214 between a case where the acceleration of the wristwatch 1 does not exceed the threshold in response to the movement of the arm of the user and a case where the acceleration of the wristwatch 1 exceeds the threshold in response to the movement of the arm of the user.

[First Display Mode]

FIG. 13A to FIG. 13C are views for describing the first display mode of the wristwatch 1 according to the embodiment 2. When the acceleration sensor 610 in the wristwatch 1 detects the acceleration that exceeds a threshold set in advance in response to an operation of a user to view the wristwatch, the display state "a" is brought into a state where the display state "a" is alternately changed over between a state "b" where respective numerals that indicate the time are rotated in the predetermined direction (see the directions indicated by an arrow around the numerals) and a state "c" where respective numerals that indicate the time are rotated in the direction opposite to the predetermined direction (see the directions indicated by arrows around the numerals). To be more specific, when the acceleration that the display control unit 450 receives from the acceleration sensor 610 exceeds the threshold stored in the data storage unit 420 in advance, the display control unit 450 makes each of the drive circuits 510 to 514 perform a display where four numerals that form the present time 252 are displayed on the display unit 210 or the like vibrate. To realize such a display, the user selects, for example, "other display modes" from the display image selection screen that functions as the display image selection unit 410 and, further, selects, for example, "time vibration mode" among a plurality of choices in "other display modes". The vibration images of the numerals are stored in the image data storage unit 420. Four numerals that form the present time 252 may vibrate not only on the display unit 210 but also on the display units 211 to 214 by sticking out from the display unit 210.

The image data storage unit 420 stores a computer program programmed such that when the acceleration detected by the acceleration sensor 610 exceeds the threshold and a predetermined time elapses from the time at which the display for vibrating the numerals is started, the display is returned to the original display state "a". The display control unit 450 measures the lapse of the time from the starting of the vibration, and changes over the vibration display state to a state where the display state "b" and the display state "c" are repeated in accordance with the above-mentioned computer program to the original display state "a" where the numerals are not vibrated after the predetermined time (for example, 30 seconds) elapses.

[Second Display Mode]

FIG. 14 is a view for describing the second display mode of the wristwatch 1 according to the embodiment 2. The second display mode is set when a user designates the mode from the display image selection mode 410. The second display mode is a display mode where the present time 252 is displayed on the upper face display unit 210 as an initial state, and when acceleration is applied to the wristwatch 1 as an arm of a user moves, for example, using the addition of the acceleration as a trigger, the present time 252 moves like a jelly and sticks out over side surfaces. To make the wristwatch 1 perform such a display, the user selects, for example, "other display modes" from the display image selection screen that functions as the display image selection unit 410 and, further, selects, for example, "time display stick-out mode" among a plurality of choices in "other display modes". In the wristwatch 1 according to the embodiment 2, the display control unit 450 transmits signals to the respective drive circuits 510 to 514 and controls each of five display units 210 to 214 such that the display is realized where, when acceleration at the time of viewing the wristwatch 1 by moving the his/her hand to the wrist of the user exceeds a threshold that is stored in advance in the image data storage unit 420, the present time 252 moves.

Further, when the present time 252 sticks out over the side faces, the side face over which the present time 252 sticks out may be programmed in advance, or the display may be performed such that the present time 252 sticks out over the organic EL sheet on the side face that the user can view corresponding to the inclination measured by the acceleration sensor 610.

FIG. 15A to FIG. 15H illustrate a series of movement in which the present time sticks out over one or more side face display units out of the side face display units 211 to 214 in addition to the upper face display unit 210 in accordance with the display mode programmed in advance. As illustrated in FIG. 15A to FIG. 15H, four numerals that form the present time stick out over four side faces besides the upper face display unit 210 thus changing its display mode from "a" to "h" in FIG. 25A and FIG. 25B. After the display mode is changed from "a" to "h", the program may be finished, or the display mode may again return to "a" and may be changed from "a" to "h". Such a display operation is performed in accordance with the description of a computer program stored in the image data storage unit 420.

[Third Display Mode]

Figure 16:
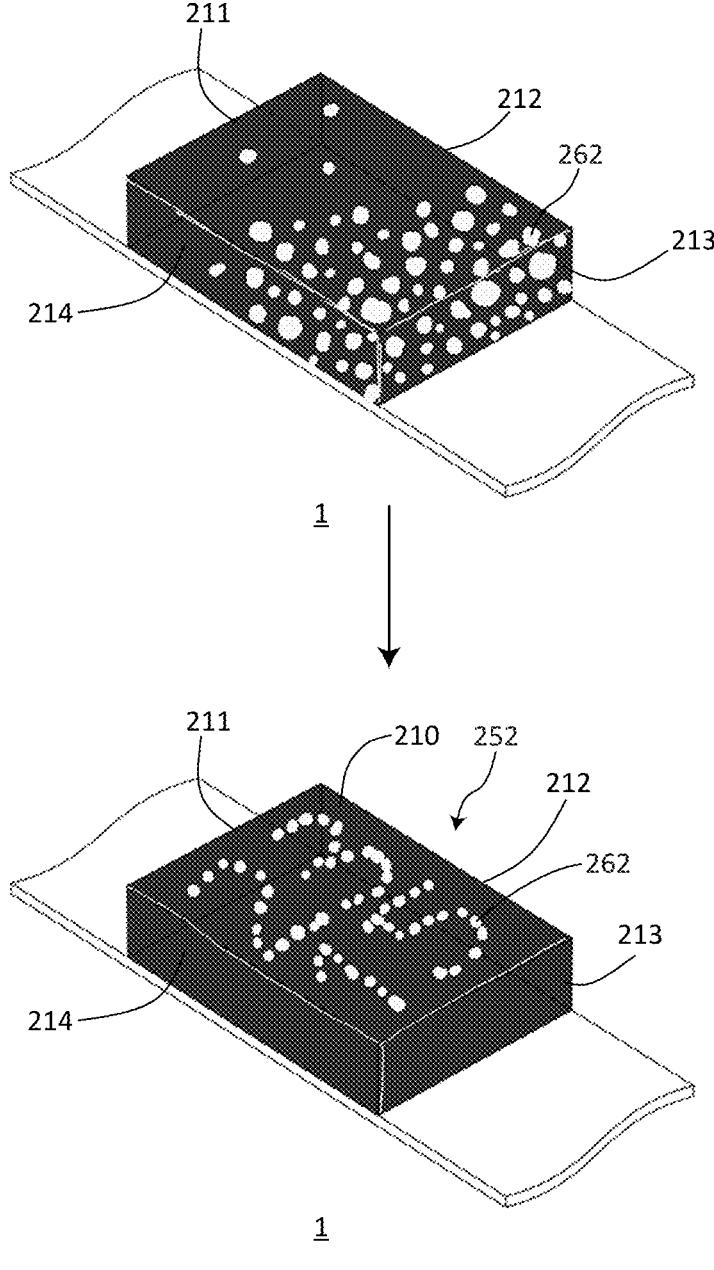

FIG. 16 is a view for describing the third display mode of the wristwatch 1 according to the embodiment 2. The third display mode is a display mode where a mass of small balls 262 physically move in the wristwatch body 100 having a rectangular parallelepiped shape in response to the movement of an arm of the user. When the user views the wristwatch 1, the small balls 262 gather so that the mass of small balls 262 is changed to the time display. That is, in this display mode, as an initial state, a state is displayed where small balls 262 are dispersed and move at random in the wristwatch body 100 having a rectangular parallelepiped shape and, thereafter, with a lapse of time, a state is displayed where the small balls 262 gather on an upper face so that the present time 252 appears. To make the wristwatch 1 perform such a display, the user selects, for example, "other display modes" from the display image selection screen that functions as the display image selection unit 410 and, further, selects, for example, "small ball pattern" among a plurality of choices in "other display modes". When the acceleration of the wristwatch body 100 generated in response to the operation of the arm of the user and/or the inclination of the upper face display unit 210 are/is detected by the acceleration sensor 610, the display control unit 450 performs the display where a large number of small balls 262 move in the wristwatch body 100 based on the detection state. The small balls 262 may move, for example, along with the lapse of time or in response to the movement of the hand of the arm of the user. The display that forms the present time 252 using the small balls 262 may be changed over from the display of the movement of the balls 262 at random that has been performed at the point of time that the acceleration sensor 610 does not detect the acceleration. In this case, when the acceleration from the acceleration sensor 610 becomes zero or equal to or less than a threshold, the display control unit 450 receives a signal, reads a computer program stored in the image data storage unit 420, and can change over the display to the display of the present time 252 formed of the small balls. To be more specific, the display control unit 450 controls the display on each of five display units 210 to 214 by transmitting signals to the respective drive circuits 510 to 540 such that the above-mentioned display mode is realized.

[Fourth Display Mode]

Figure 17:
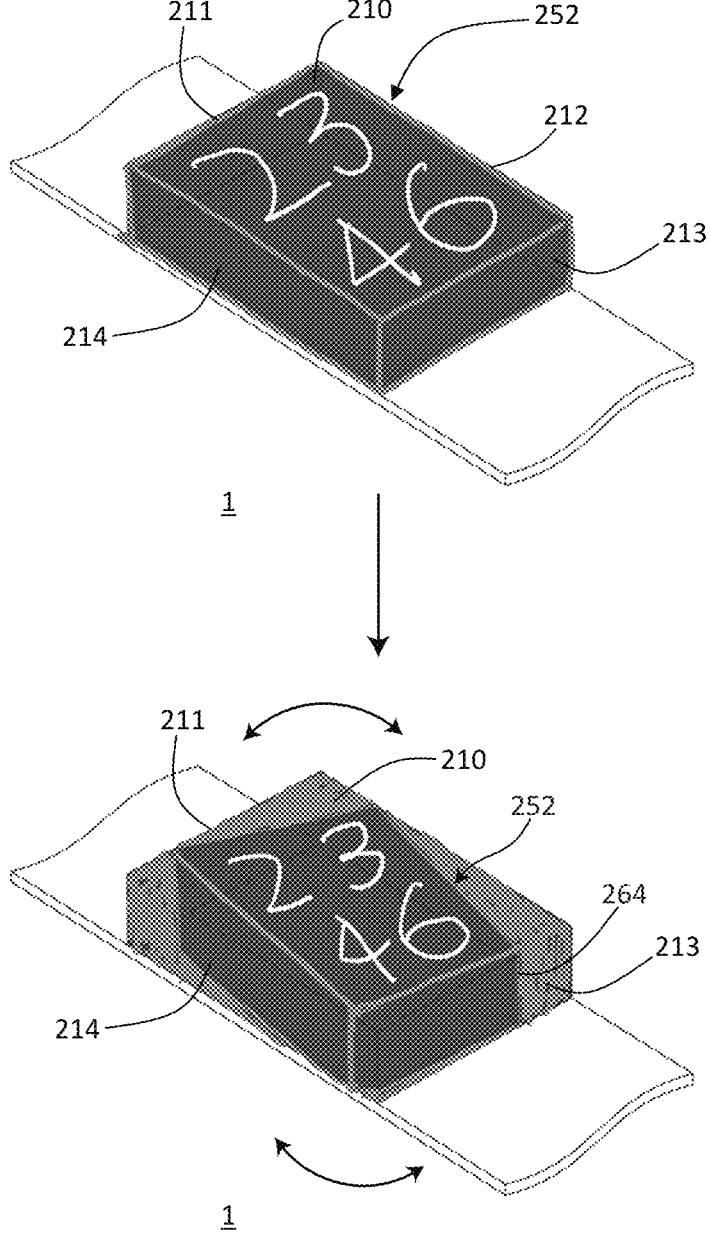

FIG. 17 is a view for describing the fourth display mode of the wristwatch 1 according to the embodiment 2. The fourth display mode is a display mode where the wristwatch 1 realizes an illusory visual effect where a frame itself of the wristwatch body 100 shakes like a jelly in the inside of the wristwatch 1 in response to acceleration that is generated when the user views the wristwatch 1. That is, as illustrated in FIG. 17, the fourth display mode is a display mode where the present time 252 is displayed on the upper face display unit 210 in an initial state, and when acceleration is applied to the wristwatch 1 along with the movement of an arm of a user, for example, a pseudo wristwatch frame 264 appears as if the pseudo wristwatch frame 264 shakes like a jelly in the inside of the wristwatch 1 in response to the movement of the arm (an illusory display mode). To make the wristwatch 1 perform such a display, the user selects, for example, "other display modes" from the display image selection screen that functions as the display image selection unit 410 and, further, selects, for example, "mode where frame body shakes like a jelly" from a plurality of choices in "other display modes". In the wristwatch 1 according to the embodiment 2, the display control unit 450 controls the display on each of five display units 210 to 214 such that the display mode described above can be realized. The image data storage unit 420 stores: the pseudo wristwatch frame 264 (formed of a plurality of frames) that is changed over from the display of the present time 252 on the upper face display unit 210; a predetermined threshold of acceleration; and a computer program for changing over the display from the usual time display to the pseudo wristwatch frame 264 when a signal of acceleration that exceeds the predetermined threshold is obtained.

When the display control unit 450 receives a signal of acceleration that exceeds the predetermined threshold from the acceleration sensor 610, the display control unit 450 reads a computer program in the image data storage unit 420, transmits signals to the respective drive circuits 510 to 514, and changes over the display of the present time 252 to the display of the pseudo wristwatch frame 264. The data of the respective display images are read from the image data storage unit 420 by the display control unit 450. The computer program may be programmed such that, when a predetermined time has elapsed from the detection of the acceleration that exceeds the predetermined threshold, the display is changed over from the display of the pseudo wristwatch frame 264 to the display of the original present time 252.

[Fifth Display Mode]

Figure 18:
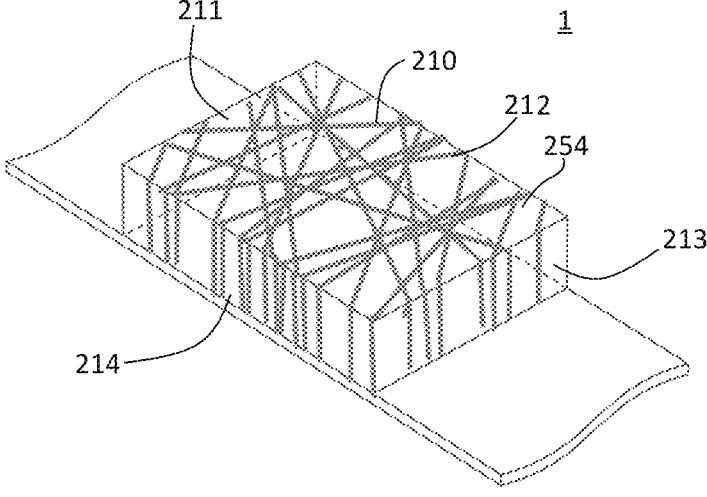

FIG. 18 is a view for describing the fifth display mode of the wristwatch 1 according to the embodiment 2. As illustrated in FIG. 18, the fifth display mode is a display mode where a mode in which a ribbon 254 is wound around the wristwatch 1 is displayed. In such a display mode, a mode where the ribbon 254 is wound around and a mode where the wound ribbon 254 is loosened may be displayed alternately along with the lapse of time, for example, with the lapse of every 1 second. To make the wristwatch 1 perform such a display, the user selects, for example, "other display modes" from the display image selection screen that functions as the display image selection unit 410 and, further, selects, for example, "ribbon winding pattern" from a plurality of choices in "other display modes". The fifth display mode can be realized by changing over the display of the usual present time 252 to the display of winding of the ribbon 254 when the acceleration detected by the acceleration sensor 610 exceeds a threshold larger than the predetermined threshold in the first display mode to the fourth display mode (referred to as a second threshold). The image data storage unit 420 stores a ribbon-winding-type time display frame; the second threshold of acceleration; and a computer program for changing over the display from the usual time display to the ribbon-winding-type time display frame when a signal of the acceleration that exceeds the second threshold is obtained. The computer program may be programmed such that the display is changed over from the usual time display of the ribbon-winding-type display frame to the original present time 252 when a predetermined time (for example, 3 minutes) elapses from the detection of the acceleration that exceeds the second threshold.

When the display control unit 450 receives the signal of the acceleration that exceeds the second threshold from the acceleration sensor 610, the display control unit 450 reads a computer program stored in the image data storage unit 420, transmits signals to the respective drive circuits 510 to 514, and changes over the display of the present time 252 to the ribbon-winding-type time display frame. The data of the respective display images are read from the image data storage unit 420 by the display control unit 450.

Figure 19:
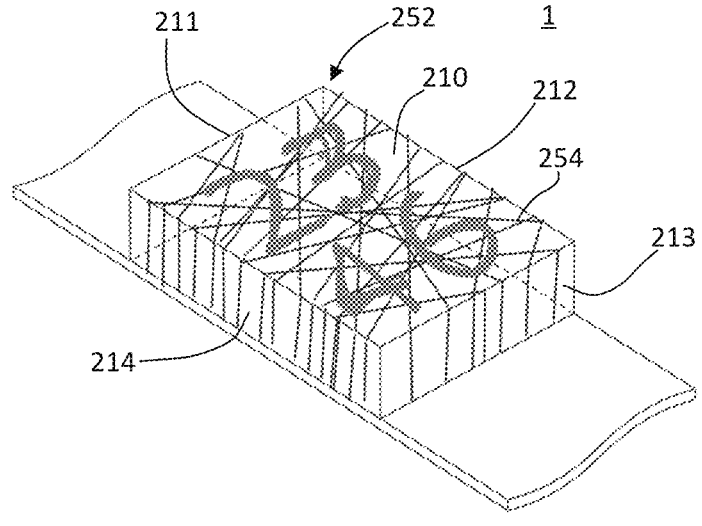

FIG. 19 is a view for describing a modification of the fifth display mode of the wristwatch 1 according to the embodiment 2. This modification is an example where the display of winding of the ribbon 254 around the wristwatch 1 while maintaining the display of the present time 252 on the upper face display unit 210. Such a display control can be realized by a control method substantially equal to the control described with reference to FIG. 18. As the modification, the display may be performed such that the ribbon 254 is wound in seconds in a state where the present time 252 is not displayed as illustrated in FIG. 18 when the acceleration does not exceed the second threshold, while the display is performed such that the ribbon 254 is wound in seconds in a state where the present time 252 is displayed as illustrated in FIG. 19 when the acceleration exceeds the second threshold.

[Sixth Display Mode]

Figure 20:
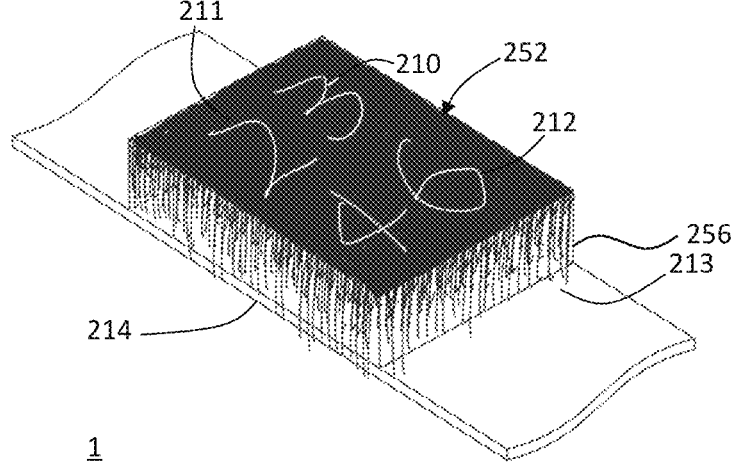

FIG. 20 a view for describing the sixth display mode of the wristwatch 1 according to the embodiment 2. As illustrated in FIG. 20, the sixth display mode is a display mode where fine particles 256 are infiltrated into the wristwatch 1 from an upper face of the wristwatch 1 to a bottom face of the wristwatch 1. In the sixth display mode, a display mode may be adopted where the color of a surface changes periodically and the fine particles 256 having different color are infiltrated into the wristwatch 1. To make the wristwatch 1 perform such a display, the user selects, for example, "other display modes" from the display image selection screen that functions as the display image selection unit 410 and, further, selects, for example, "infiltration pattern" from a plurality of choices in the "other display modes". With such processing, the display in the sixth display mode is performed on the wristwatch 1. The sixth display mode can be realized by changing over the display from the display where only the present time 252 has been displayed to the display where the fine particles 256 are infiltrated into the side face display units 211 to 214 directed in the bottom face direction while maintaining the display of the present time 252 on the upper face display unit 210. The image data storage unit 420 stores: a moving image where the fine particles 256 are infiltrated, the second threshold of the acceleration, and a computer program for switching over the display from the usual time display to the display where the fine particles 256 are infiltrated when the display control unit 450 receives a signal of the acceleration that exceeds the second threshold. The computer program may be programmed such that, when a predetermined time (for example, three minutes) counted from the detection of acceleration that exceeds the second threshold elapses, the display is changed over from the display where the fine particles 256 are infiltrated to the display of the original present time 252.

When the display control unit 450 receives the signal of the acceleration that exceeds the second threshold from the acceleration sensor 610, reads a computer program in the image data storage unit 420, transmits the signal to the respective drive circuits 510 to 514, and changes over the display of the present time 252 to the display where the fine particles 256 are infiltrated. In a case where the colors of the upper face display unit 210 and the side face display units 211 to 214 are periodically changed, the display control unit 450 instructs the changing of colors to the respective drive circuits by reading a computer program having the above-mentioned description in the image data storage unit 420. Data necessary for the display is read from the image data storage unit 420 by the display control unit 450.

[Seventh Display Mode]

Figure 21:
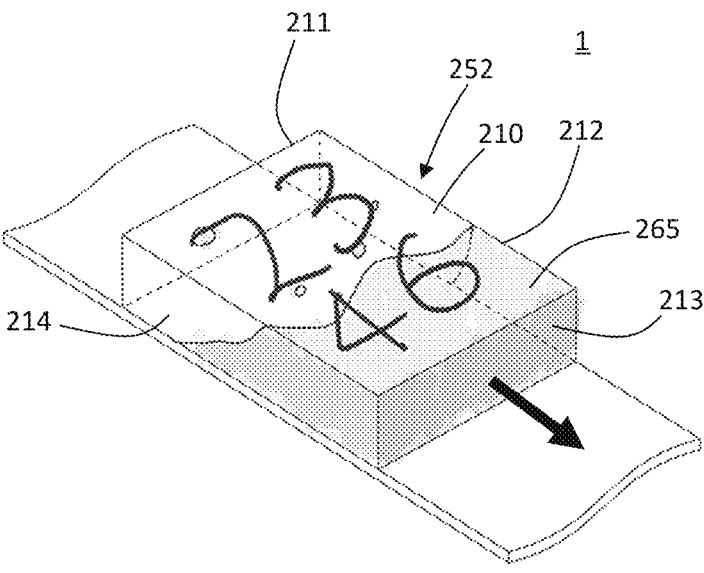

FIG. 21 a view for describing the seventh display mode of the wristwatch 1 according to the embodiment 2. As illustrated in FIG. 21, the seventh display mode is a display mode where, as viewed from a user, the display is performed as if a transparent vessel is filled with a liquid, and the liquid is increased and decreased when the liquid swings in the transparent vessel. To make the wristwatch 1 perform such a display, the user selects, for example, "other display modes" from the display image selection screen that functions as the display image selection unit 410 and, further, selects, for example, "liquid pattern" from a plurality of choices in the "other display modes". With such processing, the display in the wristwatch 1 in accordance with the eighth display mode can be realized.

The image data storage unit 420 stores data for displaying the liquid 265 in the transparent vessel, and a computer program programmed for changing the mode of the liquid 265 in the transparent vessel in accordance with a signal from the acceleration sensor 610 and a lapse of time and for displaying the changed mode on the display units 210 to 214. The display control unit 450 performs the display of the liquid 265 corresponding to the degree of horizontal and the movement of the wristwatch 1 by reading a computer program stored in the image data storage unit 420 based on a signal that the display control unit 450 receives from the acceleration sensor 610, and by transmitting a signal to the respective drive circuits 510 to 514. In FIG. 21, the upper face display unit 210 is inclined in the direction indicated by a bold line and hence, the liquid 265 is shifted toward the display 213 side. Further, since the wristwatch 1 moves in the direction indicated by the bold line, the liquid 265 is displayed as if the liquid 265 generates waves.

Further, the liquid 265 can be displayed such that the liquid 265 is increased along with the lapse of the present time 252. Such a display can be also realized by the control performed by the display control unit 450. That is, the display control unit 450 reads a computer program in the image data storage unit 420 based on a time signal, transmits a signal to the respective drive circuits 510 to 514, and performs a display where the liquid 265 is gradually increased along with the lapse of time.

In this manner, the display control unit 450 controls a change in the position of the liquid 265 in the wristwatch body 100 based on the acceleration from the acceleration sensor 610, and controls a change in a quantity of the liquid 265 based on the time. As a modification, both changes in position and quantity of the liquid 265 may be controlled depending on only the time without using a signal from the acceleration sensor 610. In this case, the liquid 265 is displayed such that the liquid 265 performs the swinging movement programmed in advance in the transparent vessel and a quantity of the liquid 265 is increased along with the lapse of time. On the other hand, the display control unit 450 may perform a control such that both the position and the quantity of the liquid 265 change depending on only the acceleration transmitted from the acceleration sensor 610 without depending on time. In this case, the liquid 265 is displayed such that the liquid 265 performs the swinging movement in the transparent vessel corresponding to the inclination and the acceleration of the wristwatch body 100.

EIGHTH EMBODIMENT

FIG. 22A and FIG. 22B views for describing the eighth display mode of the wristwatch 1 according to the embodiment 2. As illustrated in FIG. 22A and FIG. 22B, the eighth display mode is a display mode where streams having different flow directions 266 are generated in each of display faces (the upper face display unit 210 and four side face display units 211 to 214), and the streams change at random for every 1 second, for example. The present time 252 is also displayed on the upper display face unit 210. However, the present time 252 may not be displayed. This display mode is a mode where high-speed streams flowing in different directions are generated on each of the faces of the display units 210 to 214. That is, the respective faces are distinguished from each other by the directivities of the flows of the streams. To make the wristwatch 1 perform such a display, the user selects, for example, "other display modes" from the display image selection screen that functions as the display image selection unit 410 and, further, selects, for example, "stream pattern" from a plurality of choices in the "other display modes". With such processing, the display in accordance with the eighth display mode can be realized in the wristwatch 1.

FIG. 22A and FIG. 22B illustrate an example where the display modes of the streams are repeated between a state "a" and a state "b" for every 1 second. However, the changeover of the display between the state "a" and the state "b" is not limited to "for every 1 second", and the changeover of the display may be performed arbitrarily such as "for every 2 seconds" or "for every 10 seconds". In performing the display modes described above, the display control unit 450 performs a control so as to make each of the display units 210 to 214 perform the display of the streams based on a time signal. Images of the streams are stored in the image data storage unit 420. The display control unit 450 reads a computer program in the image data storage unit 420, reads images of the streams in the image data storage unit 420, and transmits signals to the respective drive circuits 510 to 514 thus realizing the display of the images.

As a modification, the display mode of the streams may be changed based on signals from the acceleration sensor 610. The image data storage unit 420 stores: image data of plural kinds of streams; a threshold of acceleration when the image of the stream is changed over; and a computer program for selecting the image of one kind of stream from images of the plural kinds of streams. When the acceleration that the display control unit 450 receives from the acceleration sensor 610 exceeds the above-mentioned threshold stored in advance, the display control unit 450 selects the data of the image of the stream at random from the image data storage unit 420, transmits the signal to the drive circuits 510 to 514 thus changing over the display of the image of the present stream to the display of the image of the new stream.

As has been described above, the wristwatch 1 according to the embodiment 2 can perform the displays of the display units 210 to 214 or can change the displays of the display units 210 to 214 by making use of the information from the acceleration sensor 610 and hence, it is possible to provide a wristwatch having a new value not obtained by the prior art.

EMBODIMENT 3

Next, the embodiment 3 of the present invention is described. In the embodiment 3, constitutional components substantially equal to the corresponding components of the above-mentioned embodiments are given the same symbols, and there may be a case where the description of the constitutional components is omitted.

A detection unit provided to the wristwatch 1 according to the embodiment 3 of the present invention includes a pulse meter (or a heart rate monitor), a thermometer, a pressure gauge for measuring a blood pressure, an electrocardiograph or a three-dimensional acceleration sensor that detects health relating information (information including health information and fitness information) of a user of the wristwatch 1. The detection unit can detect, as health relating information of the user of the wristwatch 1, pulses (or a heart rate), a body temperature, a blood pressure, or information relating to activity. In the above-mentioned information, "information relating to activity" means information relating to the behavior of a user. As information relating to activity, it is possible to exemplify: information on the number of steps in walking; information on the kilometers that the user walked; the number of floors that the user climbed up on foot; information on the consumption of calories; information on how many hours that the user was seated on a chair; information on how many hours that the user was continuously seated on a chair, information on how many hours that the user played swimming; information on when the user woke up and when the user went into bed, information on what the user ate, information on how many hours the user slept, information on the consumption of calories, time difference information, information on how many hours that the user watched a movie, information on how many hours that the user watched a TV program, information on how many hours that the user read books, information on how many hours that the user worked, information on washing hands, information on confirmation of contact with other people, information on breathing, information on listened music, podcast information, emergency SOS information and the like.

Figure 23:
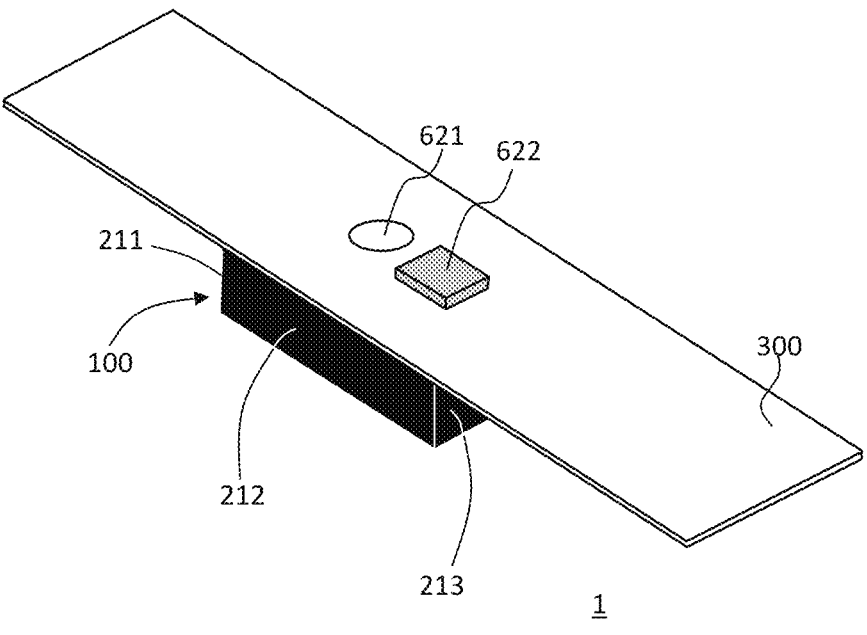

FIG. 23 is a view illustrating a state where main units of the wristwatch 1 according to the embodiment 3 are viewed from below. Faces of the wristwatch 1 other than a lower face are substantially equal to the corresponding faces of the wristwatch 1 according to the embodiment 2 (see FIG. 11). In the embodiment 3, a belt 300 that corresponds to a lower face of a wristwatch body 100 has two through holes that penetrate belt 300 in the thickness direction of the belt 300. Out of these through holes, one through hole is a circular hole as viewed from the lower surface of the belt 300 (the upper surface in FIG. 23). The remaining one through hole is a rectangular hole. A light emitting/light receiving unit 621 necessary for measuring a blood pressure, pulses and an electro cardiograph is provided to the wristwatch body 100. The light emitting/light receiving unit 621 is exposed to the outside through the above-mentioned circular hole, and enables the emission of light toward the wrist of the user and reception of light from the wrist direction. Further, a body temperature measurement sensor 622 is a sensor provided to the wristwatch body 100 and having a rectangular parallelepiped shape, and is exposed from the lower face of the belt 300 through the above-mentioned rectangular hole.

Figure 24:
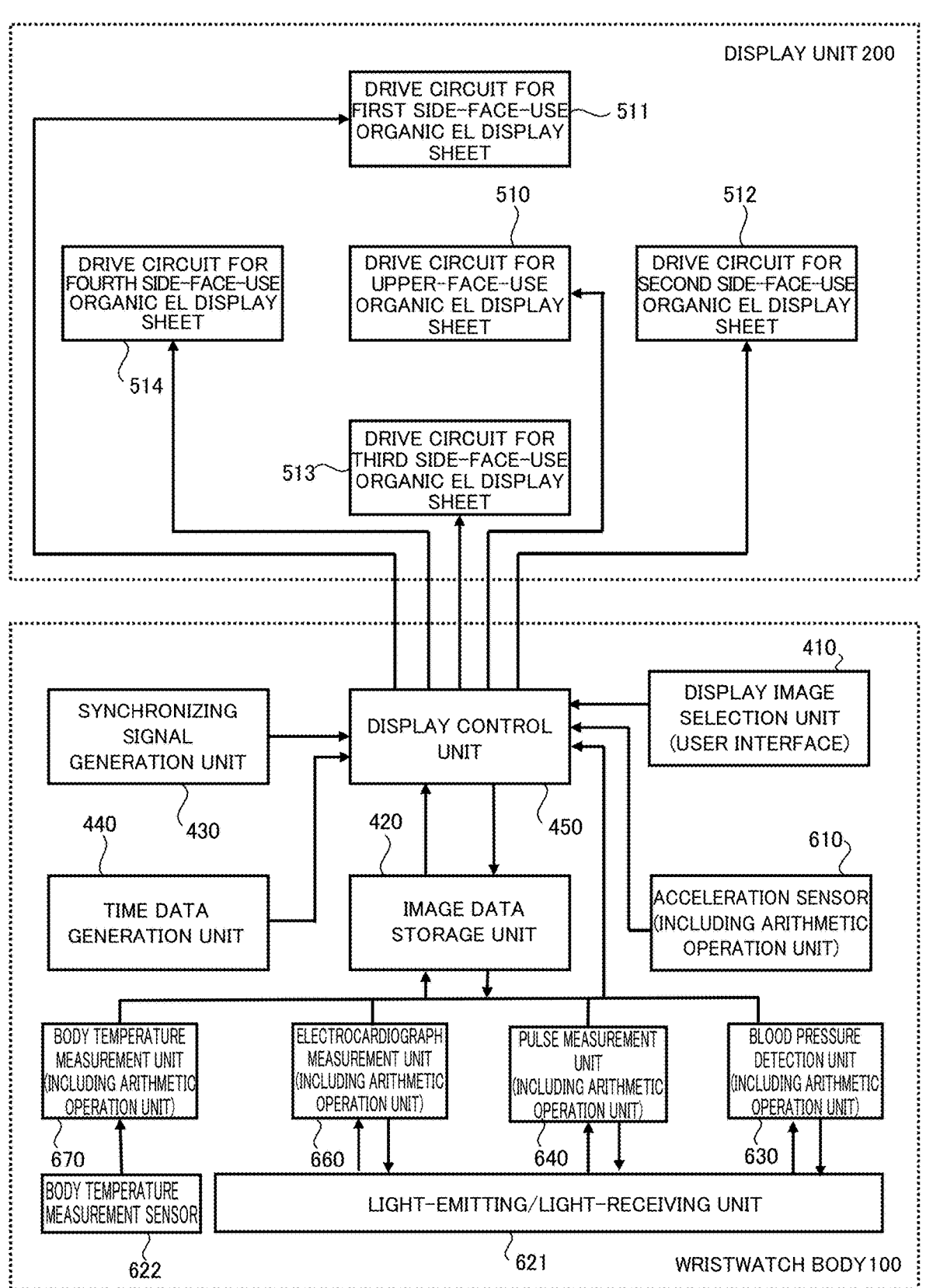

FIG. 24 is a view that is a functional block diagram illustrating the configuration of a control system for operating the wristwatch 1 according to the third embodiment 3. In the functional block diagram illustrated in FIG. 24, out of various functions that the wristwatch 1 according to the embodiment 3 has, the functional blocks necessary for performing mainly the display are illustrated. Hereinafter, with reference to FIG. 24, the functions peculiar to the embodiment 3 are described, and the repeated description of the functions substantially equal to the corresponding functions in the respective embodiments described above is omitted.

The wristwatch body 100 includes, in the same manner as the embodiment 2, various constitutional units consisting of a display image selection unit 410, an image data storage unit 420, a synchronizing signal generation unit 430, a time data generation unit 440, a display control unit 450 and an acceleration sensor 610. In addition to these various constitutional units, the wristwatch body 100 includes: the light emitting/receiving unit 621; a body temperature measurement sensor 622; a blood pressure measurement unit (also referred to as a blood pressure gauge) 630; a pulse measurement unit (also referred to as a heart rate gauge) 640; an electrocardiograph measurement unit (also referred to as an electrocardiograph gauge) 660, and a body temperature measurement unit 670. In this embodiment, the acceleration sensor 610, the blood pressure measurement unit 630, the pulse measurement unit 640, an electrocardiograph measurement unit 660, and a body temperature measurement unit 670 each also include an arithmetic operation unit. A diode for emitting light and a diode for receiving the light are mounted on the light emitting/light receiving unit 621. The body temperature measurement sensor 622 is, for example, a high sensitive sensor that measures a heat flux from a surface of a skin of a wrist of the user. A value measured by the sensor is converted into a temperature at the center of the body using a specific algorism. The display image selection unit 410 can select, besides the selection of the measurement of the acceleration, the health relating information on any one of the blood pressure measurement, the pulse measurement, the electrocardiograph measurement and the body temperature measurement. When the user selects any one of the above-mentioned measurements using the display image selection unit 410, the wristwatch 1 can perform the various displays corresponding to the selections. The detail of the various displays is described later.

At least the display control unit 450, the acceleration sensor 610, the blood pressure measurement unit 630, the pulse measurement unit 640, the electrocardiograph measurement unit 660, and the body temperature measurement unit 670 of the wristwatch body 100 perform various processing by an operation of a processing device represented by a CPU or a GPU. The various processing is performed by reading a computer program stored in the memories (ROM, RAM, EEPROM or the like) in the wristwatch body 100, for example. The memory that stores the computer program may also function as the image data storage unit 420, or may be a storage unit different from above-mentioned memory. At least one drive circuit out of the various drive circuits 510 to 514 of the display unit 200 may include the above-mentioned processing device represented by a CPU or a GPU. Hereinafter, among health or fitness information of the user of the wristwatch 1, firstly, an example of the wristwatch 1 that includes the blood pressure gauge, the pulse gauge, the heart rate gauge, and the body thermometer as the detection units is described with reference to the drawings. Next, the detection and the display of information relating to activity (information also including fitness information) using a three-dimensional acceleration sensor are described.

[First Display Mode]

FIG. 25A and FIG. 25B are views for describing a first display mode of the wristwatch 1 according to the embodiment 3. As illustrated in FIG. 25A and FIG. 25B, the first display mode is a mode where a blood pressure of the user is displayed. FIG. 25A illustrates a display example in a case where the blood pressure of the user is normal. FIG. 25B illustrates a case where the blood pressure of the user is outside the normal value, that is, the case where the blood pressure of the user is abnormal. In measuring the blood pressure, the user selects, for example, "other display mode" from the display image selection screen that functions as the display image selection unit 410 and, further, selects, for example, "blood pressure measurement" out of a plurality of choices in "other display mode". By performing such selection, it is possible to perform the blood pressure measurement. When the user selects a mode of the blood pressure measurement, the blood pressure measurement unit 630 starts the measurement of the blood pressure after a lapse of a predetermined time (for example, after 10 seconds) based on an instruction of the selection by the user. In the case of measuring the blood pressure, a green light emitting diode in the light emitting/light receiving unit 621 emits light toward the wrist of the user. This processing makes use of a system of a human body that the blood reflects light having a wavelength of green. The reflection of light differs between the case where the blood flow in the blood vessel is increased due to pulsation of the heart and the case where the blood flow is decreased due to the pulsation. When the diode for receiving light receives the reflection light with time, the blood pressure measurement unit 630 measures the blood pressure based on the difference in the reflection of light. The blood pressure measurement unit 630 can control the emission of light and the reception of light with respect to the light emitting/light receiving unit 621. When the measurement of the blood pressure finishes, the blood pressure measurement unit 630 transmits the data on the blood pressure to the display control unit 450. The display control unit 450, in accordance with a computer program stored in the image data storage unit 420, reads image data for displaying the blood pressure in the image data storage unit 420, and transmits signals to the respective drive circuits 510 to 514 thus making the display units 210 to 214 display the blood pressure.

As an example of the display mode, the blood pressure is visually displayed not only by the numerals indicating the maximal pressure and the minimal pressure but also a circular annular area 268 and an internal area 269 inside the circular annular area 268. In the case where the blood pressure of the user is normal, as illustrated in FIG. 25A, the circular annular area 268 and the internal area 269 are displayed within a range of the upper face display unit 210. On the other hand, in the case where the blood pressure of the user is abnormal, either the circular annular area 268 or the internal area 269 becomes large and is displayed in such a manner that either the circular annular area 268 or the internal area 269 sticks out over the side face display unit 212 or the side face display unit 214, for example. In the case where the maximal blood pressure is abnormal and the minimal blood pressure is normal, only the circular annular area 268 is displayed in such a manner that the circular annular area 268 sticks out over the side face display unit 212 or the side face display unit 214, for example. Further, in the case where the maximal blood pressure is normal and the minimal blood pressure is abnormal, only the internal area 269 is displayed in such a manner that the internal area 269 sticks out over the side face display unit 212 or the side face display unit 214, for example. Further, in the case where both the maximal blood pressure and the minimal blood pressure are abnormal values, as illustrated in FIG. 25B, both the circular annular area 268 and the internal area 269 are displayed such that both the circular annular area 268 and the internal area 269 stick out over the side face display unit 212 or the side face display unit 214. The display control unit 450 receives data on the image from the image data storage unit 420 corresponding to the blood pressure that the display control unit 450 receives from the blood pressure measurement unit 630, and performs the display corresponding to the blood pressure on the display units 210 to 214. In place of the above-mentioned display mode, colors of the respective areas 268, 269 may be changed without changing the sizes of the circular annular area 268 and the internal area 269. For example, in the case where the blood pressure is normal, colors of the respective areas 268, 269 may be set to green or blue, while in the case where the blood pressure is abnormal, colors of the respective areas 268, 269 can be turned to red. Both the change in sizes of the respective areas 268, 269 and the change in colors of the respective areas 268, 269 may be performed.

[Second Display Mode]

Figure 26:
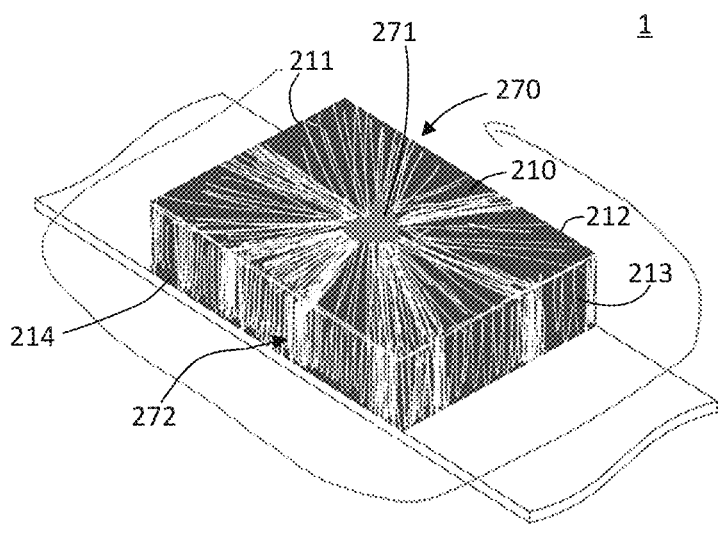

FIG. 26 is a view for describing a second display mode of the wristwatch 1 according to the embodiment 3. As illustrated in FIG. 26, the second display mode is a mode where pulses of the user are displayed. In measuring the pulses, the user selects, for example, "other display mode" from the display image selection screen that functions as the display image selection unit 410 and, further, selects, for example, "pulse measurement" out of a plurality of choices in "other display mode". By performing such selection, it is possible to perform the measurement of pulses. When the user selects the pulse measurement mode, the pulse measurement unit 640 makes the light emitting/light receiving unit 621 emit light after a lapse of a predetermined time (for example, after 10 seconds) from the instruction of the selection by the user, and detects the pulses through a blood vessel in the wrist of the user. Hemoglobin in the blood has a property of easily absorbing green light. The diode for receiving light receives a reflection light with time. The pulse measurement unit 640 calculates the number of pulses based on a change with time in intensity of the reflection light. The pulse measurement unit 640 can control the emission of light and the reception of light with respect to the light emitting/light receiving unit 621. The pulse measurement unit 640 transmits data on pulses to the display control unit 450. The display control unit 450 reads image data for displaying pulses in the image data storage unit 420 in accordance with a computer program in the image data storage unit 420, and transmits signals to the drive circuits 510 to 514 and makes the display units 210 to 214 perform the display of the number of pulses.

A pulse display 270 performed on the display units 210 to 214 includes: a heart mark 271 displayed at the center of the upper face display unit 210; lines 217 extending to the respective side face display units 211 to 214 from the heart mark 271 via the upper face display unit 210. The heart mark 271 flickers corresponding to the detected pulses. For example, the lines 272 start the display from the display unit 214, and the display is cumulatively performed in order of the display unit 213, the display unit 212 and the display unit 211. (see the direction indicated by an arrow in FIG. 26).

[Third Display Mode]

Figure 27:
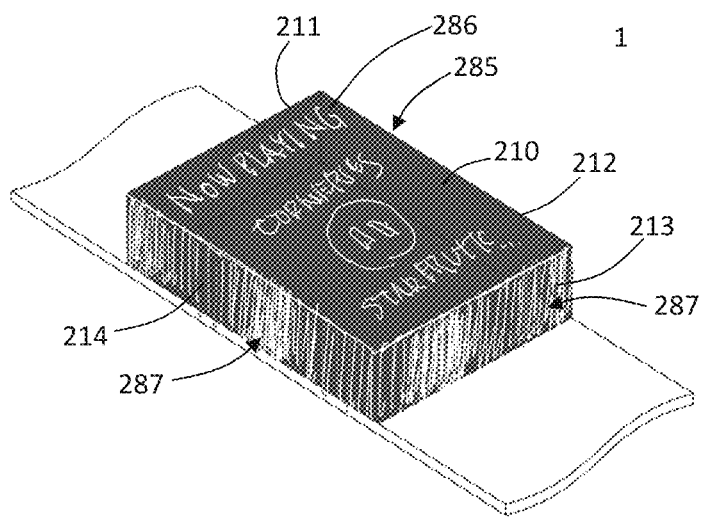

FIG. 27 is a view for describing a third display mode of the wristwatch 1 according to the embodiment 3. As illustrated in FIG. 27, the third display mode is a mode that differs from the second display mode. That is, the third display mode is a mode where a display 285 at the time of measuring pulses is performed on the display units 210 to 214. In measuring the pulses, the user selects, for example, "other display mode" from the display image selection screen that functions as the display image selection unit 410 and, further, selects, for example, "pulse measurement 2" out of a plurality of choices in "other display mode". By performing such selection, in the same manner as described in the second display mode, it is possible to perform the measurement of pulses. When the user selects the pulse measurement mode 2, the pulse measurement unit 640 makes the light emitting/light receiving unit 621 emit light after a lapse of a predetermined time (for example, after 10 seconds) from the instruction of the selection by the user, and detects the pulses through a blood vessel in the wrist of the user. When the pulse measurement unit 640 transmits data on pulses to the display control unit 450, the display control unit 450 reads image data for displaying pulses in the image data storage unit 420 in accordance with a computer program in the image data storage unit 420, and transmits signals to the drive circuits 510 to 514 and makes the display units 210 to 214 perform the display of the pulses. Further, in the third display mode, it is possible to log a change in pulses on the time axis on the side face display units 211 to 214.

The display 285 at the time of measuring pulses differs from the display of pulses in the second mode. The display 285 is performed together with the reproduction of music, for example. The display 285 includes: an information display 286 relating to the reproduction of a music on the upper face display unit 210, and a display 287 of a visualizer as information of pulses to the side face display units 211 to 214. The display 287 moves in response to pulses. In a case where the user sets his/her favorite music in advance, the display control unit 450 can selectively reproduce the music. The selection of the music can be performed using the image data storage unit 420 or a server on a cloud. It is not always necessary that the display 285 is accompanied with the reproduction of a music. For example, only a change in pulses may be displayed on the side face display units 211 to 214 together with the usual time display on the upper face display unit 210. When the measurement of pulses is performed during the reproduction of a music, the display 285 may be performed. Further, although pulses and a heart rate differ in strict meaning, the measurement of a heart rate may be performed in place of the above-mentioned measurement of pulses. In this case, for example, it is preferable to obtain a signal of a heart rate in the vicinity of the heart. For example, by providing a wristwatch 1 that includes a sensor capable of detecting vibrations at the time of generation of a heart rate and by arranging the sensor in the vicinity of the heart, information on the pulse rate may be transmitted to the wristwatch 1.

In a case where a user wants the display of an electro-cardiograph, the user selects, for example, "other display modes" from the display image selection screen that functions as the display image selection unit 410 and, further, selects, for example, "electrocardiograph measurement" from a plurality of choices in the "other display modes".

With such processing, the measurement of the electrocardiograph can be realized. When the user selects the electrocardiograph measurement mode, the electrocardiograph measurement unit 660 measures an electrocardiograph by the light emitting/light receiving unit 621 after a lapse of a predetermined time (for example, after 10 seconds) in response to an instruction of the selection from the user. The electrocardiograph measurement unit 660 catches a change with time of the reflection light received by emitting light to the blood vessel from the light emitting/light receiving unit 621 in the same manner as the case where the heart rate is measured, and converts the change with time of the reflection light into a waveform. The display control unit 450 receives data for displaying the waveform from the electrocardiograph measurement unit 660, and reads image data for electrocardiograph display in the image data storage unit 420 in accordance with a computer program stored in the image data storage unit 420. Subsequently, the display control unit 450 transmits signals to the respective drive circuits 510 to 514 and makes each of the display units 210 to 214 display an electrocardiograph. For example, the waveform of an electrocardiograph be displayed with time on at least one of the side face display units 211 to 214 illustrated in FIG. 27. The measurement of an electrocardiograph may be performed such that an electrode is mounted on a lower surface of the wristwatch or the belt and an electrocardiograph is electrically measured via the electrode.

Also with respect to "information on when the user woke up and when the user went into bed" and "how many hours the user slept" that are examples of activity information, a heart rate of the user is detected by the pulse measurement unit 640 and the light emitting/light receiving unit 621, and these information can be displayed on the display units 210 to 214 by the display control unit 450. This is because the pulse measurement unit 640 can detect the sharp increase of the number of pulses when the user wakes up and the sharp decrease of the number of pulses when the user goes to bed. As a modification of the third display mode, in place of displaying "change of a pulse on a time axis", "a change in a sound pressure level on a time axis" can be displayed as information on beat of a music during reproduction.

[Fourth Display Mode]

Figure 28:
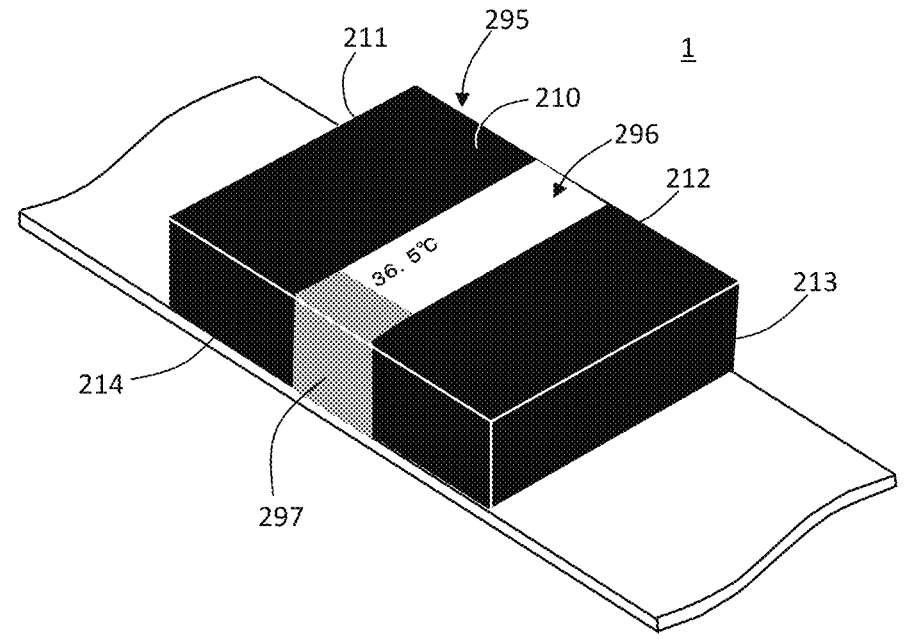

FIG. 28 is a view for describing a fourth display mode of the wristwatch 1 according to the embodiment 3. As illustrated in FIG. 28, the fourth display mode is a mode where the display 295 of a body temperature of a user is displayed on the display units 210 to 214. In measuring the body temperature, the user selects, for example, "other display mode" from the display image selection screen that functions as the display image selection unit 410 and, further, selects, for example, "body temperature measurement" out of a plurality of choices in "other display mode". By performing such selection, it is possible to perform the measurement of the body temperature. When the user selects the body temperature measurement mode, the body temperature measurement unit 670 makes the body temperature measurement sensor 622 measure the body temperature after a lapse of a predetermined time (for example, after 10 seconds) from the instruction of the selection by the user. When the measurement of the body temperature is finished, the body temperature measurement unit 670 receives data on the body temperature from the body temperature measurement sensor 622, and transmits the data to the display control unit 450. The display control unit 450 reads image data for displaying the body temperature in the image data storage unit 420 in accordance with a computer program in the image data storage unit 420, transmits signals to the respective drive circuits 510 to 514, and makes each of the display units 210 to 214 perform the display 295 of the body temperature.

In FIG. 28, a region 297 that indicates a high temperature area and a low temperature area of the body temperature is displayed on a strip-shaped display unit 296 from the side face display unit 212 to the side face display unit 214 by way of the upper face display unit 210. The region 297 is displayed in an extending manner from a lower side of the side face display unit 214 in the width direction to the upper face display unit 210. When the body temperature exceeds a normal temperature, the region 297 extends in the direction from the upper face display unit 210 to the side face display unit 212. In this display mode, a numerical value that indicates the body temperature (36.5° C. in this example) is displayed on the strip-shaped display unit 296 together with the region 297. However, the numerical value that indicates the body temperature is not indispensable. Further, although the present time is not displayed on the upper face display unit 210, the present time may be displayed on the upper face display unit 210.

[Example of Detection and Display of Activity Information Using Acceleration Sensor]

The acceleration sensor 610 that forms a detection unit provided to the wristwatch 1 also can detect information relating to activity of the user of the wristwatch 1. For example, the information that the number of steps that the user has walked and the distance in terms of Km that the user has walked can be detected by the acceleration sensor 610. For example, the number of steps and the distance can be displayed on the side display units 211 to 214 by changing the length of the region 297 corresponding to the number of steps or the distance.

As has been described heretofore, the wristwatch 1 according to the embodiment 3 can display the health and the fitness information of the user and information relating to activity in a wide range including such fitness information on the display units 210 to 214 by making use of information from the acceleration sensor 610, the blood pressure measurement unit 630, the pulse measurement unit 640, the electrocardiograph measurement unit 660 and the body temperature measurement unit 670. Accordingly, it is possible to provide the wristwatch having a new value not obtained by the prior art.

EMBODIMENT 4

Next, the embodiment 4 of the present invention is described. In the embodiment 4, constitutional components substantially equal to the corresponding components of the above-mentioned respective embodiments are given the same symbols, and there may be a case where the description of the constitutional components is omitted.

Figure 29:
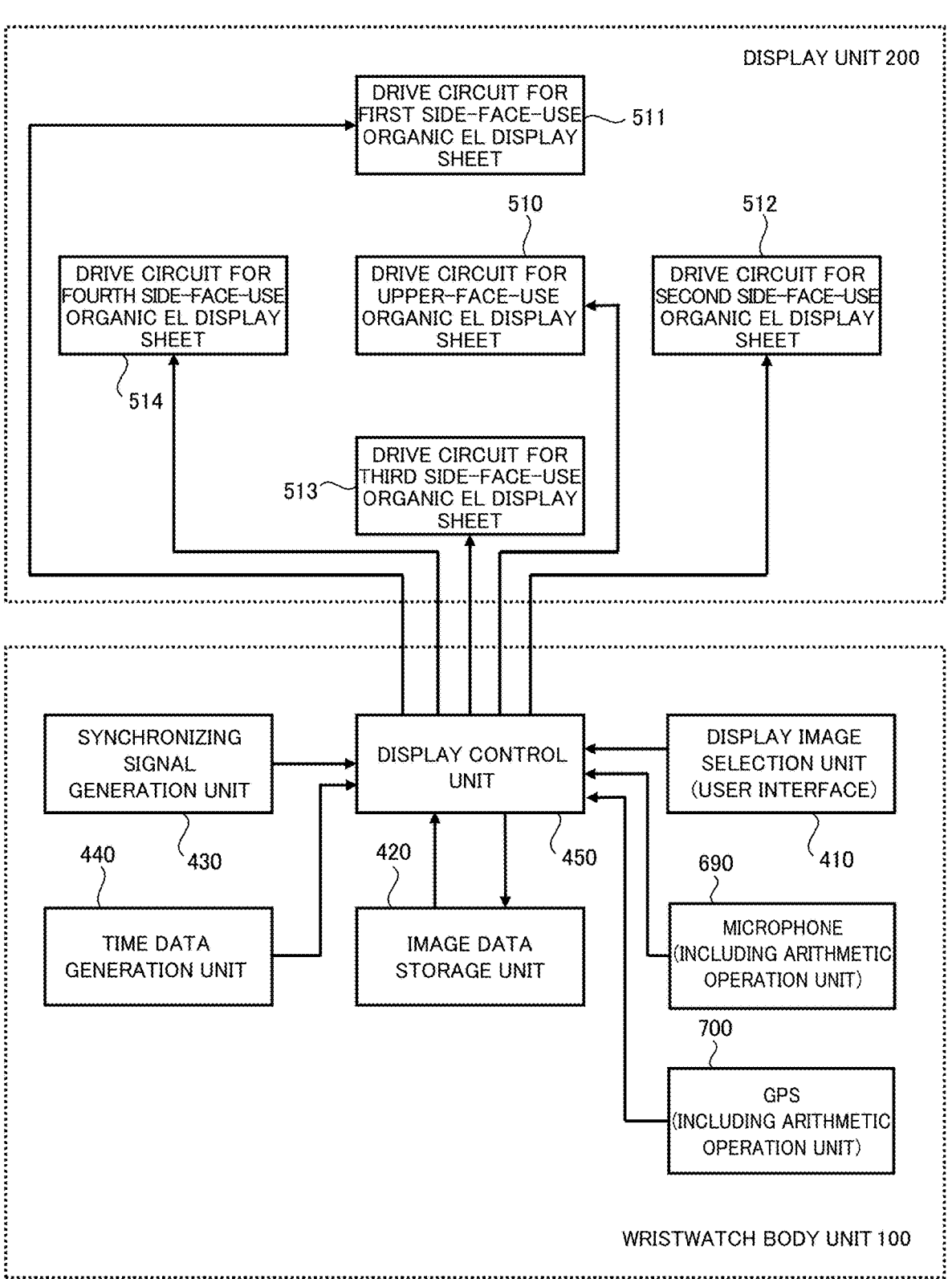

FIG. 29 is a view illustrating the configuration of a control system for operating the wristwatch 1 according to the embodiment 4 as a functional block diagram. The functional block diagram illustrated in FIG. 29 illustrates functional blocks necessary for performing mainly the display among various functions and sensors necessary for detecting the movement of the wristwatch 1 that the wristwatch 1 according to the embodiment 4 has. Hereinafter, with reference to FIG. 29, the functions peculiar to the embodiment 4 are described, and the repeated description of the functions substantially equal to the corresponding functions in the above-mentioned respective embodiments is omitted.

The wristwatch body 100 includes, in the same manner as the respective embodiments described above, various constitutional units that includes a display image selection unit 410, an image data storage unit 420, a synchronizing signal generation unit 430, a time data generation unit 440, and a display control unit 450. Further, the wristwatch body 100 further includes, as a detection unit, a microphone 690 and a global positioning system (GPS) 700. In the wristwatch body 100, at least the display control unit 450, the microphone 690 and the GPS 700 perform various processing by an operation of a processing device represented by a CPU or a GPU. In this embodiment, the selection, the change or the like of the display on the display units 210 to 214 can be performed based on a voice via the microphone 690. The microphone 690 also includes an arithmetic operation unit. The display image selection unit 410 can select a mode where the display is performed based on inputting of voices and the display is changed over. When the display control unit 450 receives data on voices via the microphone 690, recognizes the voices and, thereafter, reads specific image data in accordance with a computer program stored in the image data storage unit 420. Subsequently, the display control unit 450 displays an image on each of the display units 210 to 214 by each of the drive circuits 510 to 514.

Since the wristwatch body 100 includes the GPS 700 as the detection unit, when the wristwatch 1 enters a specific positional range, the wristwatch 1 can perform a specific display. Further, in the wristwatch 1 according to the embodiment 4, the present position of the user can be also displayed on the display units 210 to 214 via the GPS 700. The GPS 700 also includes an arithmetic operation unit. The display image selection unit 410 enables the selection of a mode where the position of the user can be detected by the GPS 700. When the display control unit 450 receives the data on the positional information of the user via the GPS 700, the display control unit 450 reads specific image data (including map data) in accordance with a computer program stored in the image data storage unit 420. Subsequently, the display control unit 450 displays an image indicating the position of the user in a map on each of the display units 210 to 214 by each of the drive circuits 510 to 514.

[First Display Mode]

Figure 30:
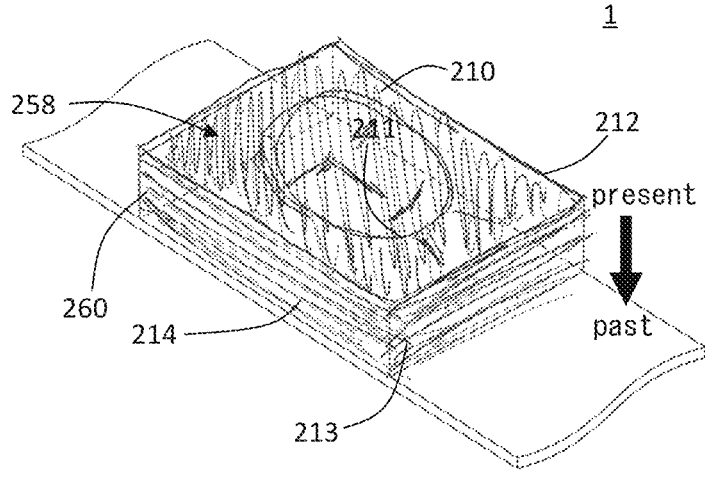

FIG. 30 is a view for describing the first display mode of the wristwatch 1 according to the embodiment 4. As illustrated in FIG. 30, the first display mode is a display mode where a mode that a plurality of images 258 that form frames of images are stacked from the present (an upper face) to the past (a bottom face) is displayed. Along with a lapse of time, on the upper face display unit 210, the image closer to the present out of the plurality of images 258 is displayed. Further, on four side face display units 211 to 214, end faces 260 of the plurality of stacked images 258 are displayed. The images 258 are displayed on the display units 210 to 214 as if, for example, 1000 sheets of images 258 in total are stored, and the newest 100 sheets of images 258 are stacked on the belt 300 in an exposed manner. The newest image (referred to as No. 1000) 258 is displayed on the upper face display unit 210. The image 258 that is placed on the lowermost position out of 100 stacked sheets of images 258 corresponds to the 901th sheet of image as counted from the oldest image 258. None of images from the oldest image 258 to the 900th sheet of images are displayed on the display units 210 to 214, and these images are positioned as if these images are embedded below the wristwatch body 100. Further, the end faces 260 of images 258 of 100 sheets are displayed on side face display units 211 to 214.

In the fourth embodiment, in performing the first display mode, the user selects, for example, "other display modes" from the display image selection screen that functions as the display image selection unit 410 and, further, selects, for example, "image frame" among a plurality of choices in "other display modes". When the user utters a voice "turn one page" after selecting the mode of the image frame, the microphone 690 receives the voice. The display control unit 450 analyzes the voice from the microphone 690, and reads an image obtained in a state where one sheet of image 258 is turned (999th sheet of image as counted from the oldest image 258: No. 999) from the image data storage unit 420, transmits signals to the respective drive circuits 510 to 514, and displays the image on each of the display units 210 to 214. The above-mentioned series of operations by the display control unit 450 are performed in accordance with a computer program stored in the image data storage unit 420. In this manner, the image 258 of No. 999 is displayed on the upper face display unit 210. The end faces 260 of 100 sheets of images 258 are displayed on the side face display units 211 to 214.

The display based on the voice that the microphone 690 utters or a changeover operation of such a display is also applicable to a case where one or more display modes in the above-mentioned respective embodiments are performed. For example, in the first display mode of the embodiment 2, numerals that form the present time 252 dance by giving an instruction such as "dancing" to the microphone 690. The image data storage unit 420 stores image data that enables the display where the numerals that form the present time 252 dance in response to the reception of the voice "dancing". The display control unit 450 reads image data in the image data storage unit 420 in accordance with a computer program in the image data storage unit 420, and transmits signals to the drive circuits 510 to 514 so as to make the display units 210 to 214 perform the display where the numerals dance. Such an example is also adopted by other display modes of the above-mentioned embodiments 2, 3. As a modification of the display mode, the display substantially equal to the above-mentioned display can be performed by making a different microphone mounted on a smartphone that is communicable with a communication unit (not illustrated in the drawing) of the wristwatch 1 utter a voice. In this case, the display control unit 450 or an arithmetic operation unit of the microphone 690 reads image data in the image data storage unit 420 based on voice data that is received from the microphone of the smartphone in a wireless or wired manner in accordance with a computer program stored in the image data storage unit 420, and transmits signals to the respective drive circuits 510 to 514 so as to make each of the display units 210 to 214 perform the display where the numerals dance.

[Second Display Mode]

Figure 31:
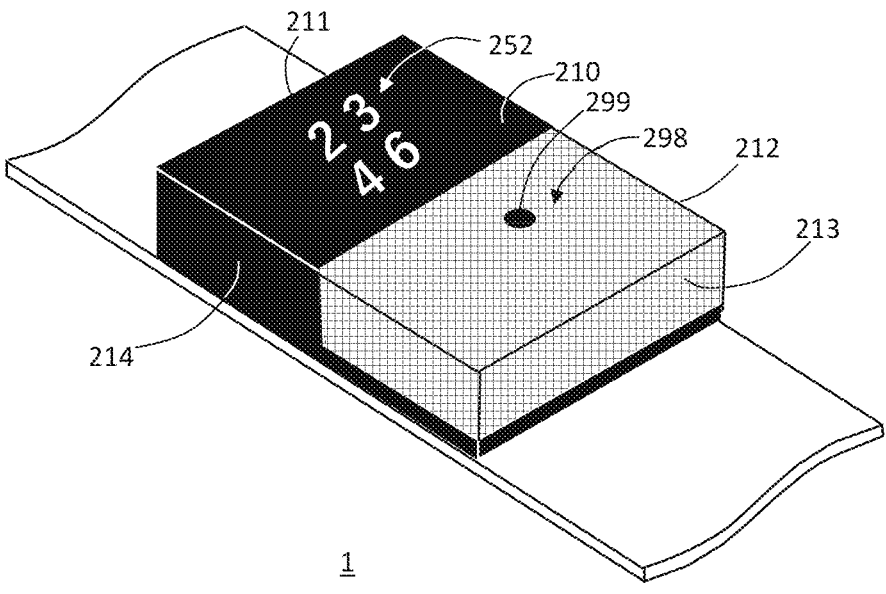

FIG. 31 is a view for describing a second display mode of the wristwatch 1 according to the embodiment 4. As illustrated in FIG. 31, when a user selects a GPS function mode from the display image selection unit 410 or utters a voice "start GPS" via the microphone 690, the display units 210 to 214 can perform the display. When a GPS 700 is started, the display control unit 450 reads map image data in the image data storage unit 420 in accordance with a computer program stored in the image data storage unit 420. A kind of a map image and data on the present position of the user are determined based on electric waves that the GPS 700 receives from a plurality of artificial satellites. When the display control unit 450 receives data from the GPS 700, the display control unit 450 transmits signals to the respective drive circuits 510 to 514, and makes each of the display units 210 to 214 perform a display 298 of the map image and a display 299 of the present position of the user. Although the present time 252 is also displayed on the upper face display unit 210, the present time 252 may not be displayed on the upper face display unit 210.

[Example of Detection and Display of Activity Information Using Microphone or GPS]

The microphone 690 and the GPS 700 that function as the detection unit provided to the wristwatch 1 can be used for realizing the detection and the display of each of the following activity information singly or in a cooperative manner. For example, with respect to "information on how many hours the user was seated on a chair", "information on how many hours the user was continuously seated on a chair", and "information on how many hours that the user swam", these information can be easily detected by making use of the microphone 690 and the GPS 700. The user may utter voices expressing starting and finishing of the operation at the time of sitting on the chair or at the time of starting swimming. A state where the user is seated on the chair and a state where the user is continuously swimming can be obtained by detecting the position of the user by the GPS 700. Further, with respect to "information on what the user ate", "information on the consumption of calories", "information on how many hours the user watched a movie", "information on how many hours the user watched a TV", "information on how many hours the user read a book" and "information on how many hours the user worked", these information can be easily detected when the use utters his/her voices indicating a kind of the operation and starting and finishing of the operation before and after the operation by directing the microphone 690 toward the user.

As has been described above, the wristwatch 1 according to the embodiment 4 can display the first display mode, the second display mode and other display modes on the display units 210 to 214 by making use of the information from the microphone 690 and the GPS 700. Accordingly, the wristwatch 1 according to the embodiment 4 becomes a wristwatch having a new value not obtained by the prior art.

OTHER EMBODIMENTS

With respect to the above-mentioned respective embodiments, the following modifications can be also performed. For example, when the acceleration sensor 610 detects a second threshold that exceeds the first threshold, the display in either the fifth display mode or the sixth display mode of the second embodiment is performed on each of the display units 210 to 214 (see FIG. 18 to FIG. 20). However, also in other display modes in the embodiment 2, the display may be changed over when the acceleration exceeds a second threshold set in advance. For example, in a case where the acceleration exceeds the second threshold, an object that is displayed (numerals, a liquid or the like) may be moved faster than a case where the acceleration falls within a range between the first threshold and the second threshold. Further, also with respect to a voice that is detected by the microphone 690, one, two or more thresholds may be set, and an object that is displayed (numerals, a liquid or the like) may be moved faster when a decibel value of the voice exceeds a predetermined threshold.

In the above-mentioned embodiment 1, the imaging element is mounted on the wristwatch or the belt. However, the present invention is not limited to such a case. The imaging element may be mounted on glasses or sunglasses of a user, and information relating to the positional relationship between eyes of the user of the wristwatch and the wristwatch may be detected from an image of the wristwatch that is imaged using the imaging element.

In the respective embodiments and the modification of these embodiments described above, the description has been made with respect to the case where the present invention is directed to the wristwatch 1. However, the present invention is not limited to the wristwatch 1, and can be also directed to a wristwatch type display device. The wristwatch type display device has the same configuration or the substantially same configuration as the wristwatch 1. The wristwatch type display device is a device that does not display time or a device that mainly aims at the display of objects other than time although the device also displays time. The wristwatch type display device may have substantially the same configuration as the above-mentioned wristwatch 1 except for the display of time. That is, in the wristwatch type display device, a wristwatch type display device body illustrated in FIG. 2A to FIG. 2C (corresponding to the wristwatch body 100) includes: respective organic EL display sheets 210 to 214 that are five display units formed over all five faces excluding a lower face that is directed toward an arm side of a user at a time of using the wristwatch type display device out of six faces that form a surface of the wristwatch type display device; a display control unit 450 configured to control a display on each of the respective display units; and a detection unit that detects at least one information out of positional information of the wristwatch type display device, posture information of the wristwatch type display device, movement information of the wristwatch type display device and health relating information of the user. The display control unit 450 has a function of controlling displays of each of the five display units 210 to 214 based on at least one information detected by the detection unit. The display control unit 450 has a function of controlling the display on each of five display units 210 to 214 such that the images that are displayed on the five display units 210 to 214 are moved in a linked manner or are associated with each other. For example, the display control unit 450 can control the display on each of five display units 210 to 214 as if the inside of the wristwatch type display device body is viewed in a see-through manner as viewed from the user.

In this manner, according to the wristwatch type display device of the present invention, various images can be displayed in various modes by also making use of four side faces in addition to the upper face of the wristwatch type display device body having a rectangular parallelepiped shape. With such a configuration, according to the wristwatch type display device of the present invention, it is possible to provide a wristwatch type display device having a new value not obtained by the prior art.

Further, the wristwatch or the wristwatch type display device of the present invention may include all or some of the respective constitutional components of the wristwatch 1 according to the embodiments 1 to 4. For example, a wristwatch or a wristwatch type display device according to a modification of the present invention may include all or some of the imaging elements 50, 60 and the arithmetic operation unit 460 of the wristwatch 1 according to the embodiment 1, the acceleration sensor 610 of the wristwatch 1 according to the embodiment 2, the light emitting/light receiving unit 621, the body temperature measurement sensor 622, the blood pressure measurement unit 630, the pulse measurement unit 640, the electrocardiograph measurement unit 660 and the body temperature measurement unit 670 of the wristwatch 1 according to the embodiment 3, and the microphone 690 and the GPS 700 of the wristwatch 1 according to the embodiment 5. With respect to the display by a voice via the microphone of the smartphone or the changeover of the display, the display and the changeover of the display are not limited to the case described in the embodiment 4, and are applicable to other embodiments.

In the wristwatch or the wristwatch type display device according to the present invention, the case is exemplified where the black member may be embedded in the gap formed between five display units 210 to 214 (between the organic EL display sheets disposed adjacently to each other) so as to make the gap inconspicuous. However, a thickness of the organic EL display sheet is thin and hence, there may be a case where the gap is not formed in a portion between the organic EL display sheets disposed adjacently to each other in a conspicuous manner. In such a case, the black member may not be embedded in the portion between the organic EL display sheets disposed adjacently to each other.

Figure 32:
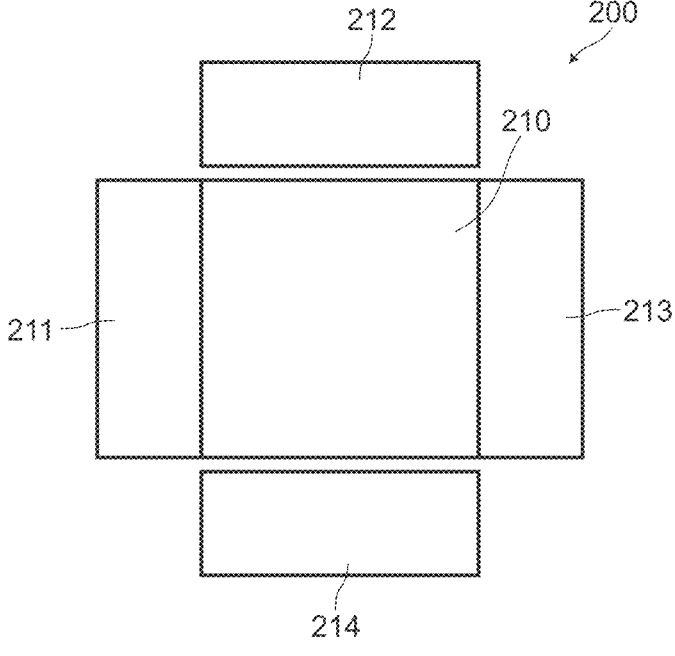

In the wristwatch or the wristwatch type display device according to the present invention, the cases are exemplified where five display units 210 to 214 are formed of five organic EL display sheets (see FIG. 2B). Further, in the above-mentioned embodiment, as the modifications of the organic EL display sheets, the case is exemplified where five display units 210 to 214 are formed of one organic EL display sheet. However, the present invention is not limited to these cases. That is, five display units 210 to 214 may be formed of two to four organic EL display sheets. For example, as illustrated in FIG. 32, five display units 210 to

214 may be formed of three organic EL display sheets. In FIG. 32, the first side face display unit 211, the upper face display unit 210 and the third side face display unit 213 are connected to each other so as to form one organic EL display sheet, and the second side face display unit 212 and the fourth side face display unit 214 are formed of two organic EL display sheets that are separated from each other as individual sheets. With such a configuration, five display units 210 to 214 are formed of three organic EL display sheets.

The example where five display units 210 to 214 are formed of three organic EL display sheets is not limited to the above-mentioned example. Although not illustrated in the drawings, for example, the second side face display unit 212, the upper face display unit 210 and the fourth side face display unit 214 may be connected to each other so as to form one organic EL display sheet, and the first side face display unit 212 and the third side face display unit 214 are formed of two organic EL display sheets that are separated from each other as individual sheets. With such a configuration, five display units 210 to 214 are formed of three organic EL display sheets.

Although not illustrated in the drawing, five display units 210 to 214 may be formed of two organic EL display sheets. For example, the first side face display unit 211 to the fourth side face display unit 214 are connected to each other so as to form one organic EL display sheet, and only the upper side face display unit 210 is formed of one separated individual organic EL display sheet. With such a configuration, five display units 210 to 214 are formed of two organic EL display sheets.

Although not illustrated in the drawing, five display units 210 to 214 may be formed of four organic EL display sheets. For example, the first side face display unit 211 and the upper face display unit 210 are connected to each other so as to form one organic EL display sheet, and the second side face display unit 212, the third side face display unit 213 and the fourth side face display unit 214 are formed of three organic EL display sheets that are separate individual sheets respectively. With such a configuration, five display units 210 to 214 are formed of four organic EL display sheets.

In the wristwatch or the wristwatch type display device according to the present invention, the description has been made with respect to the case where the wristwatch or the wristwatch type display device has five display units. However, the wristwatch or the wristwatch type display device may be a wristwatch or a wristwatch type display device that does not have five display units. That is, it is sufficient for the wristwatch or the wristwatch type display device according to the present invention to include: the wristwatch body 100 or the wristwatch type display device body having a rectangular parallelepiped shape; at least two display units that are formed over all of "the upper face on a side opposite to a lower side directed to an arm side of a user at the time of using the wristwatch" and "at least one side face of four side faces" out of six faces that form the surface of the wristwatch body 100 or the wristwatch type display device body; and the display control unit that controls the displays on at least two respective display units. That is, in the above-mentioned respective embodiments, at least two display units are formed of five display units formed over all five respective faces formed of the upper face and four side faces. However, it is sufficient that the wristwatch 1 or the wristwatch type display device has at least two display units instead of five display units.

Figures 33A, 33B, 33C, 33D, 33E, 33F, 33G, 33H, 33I:
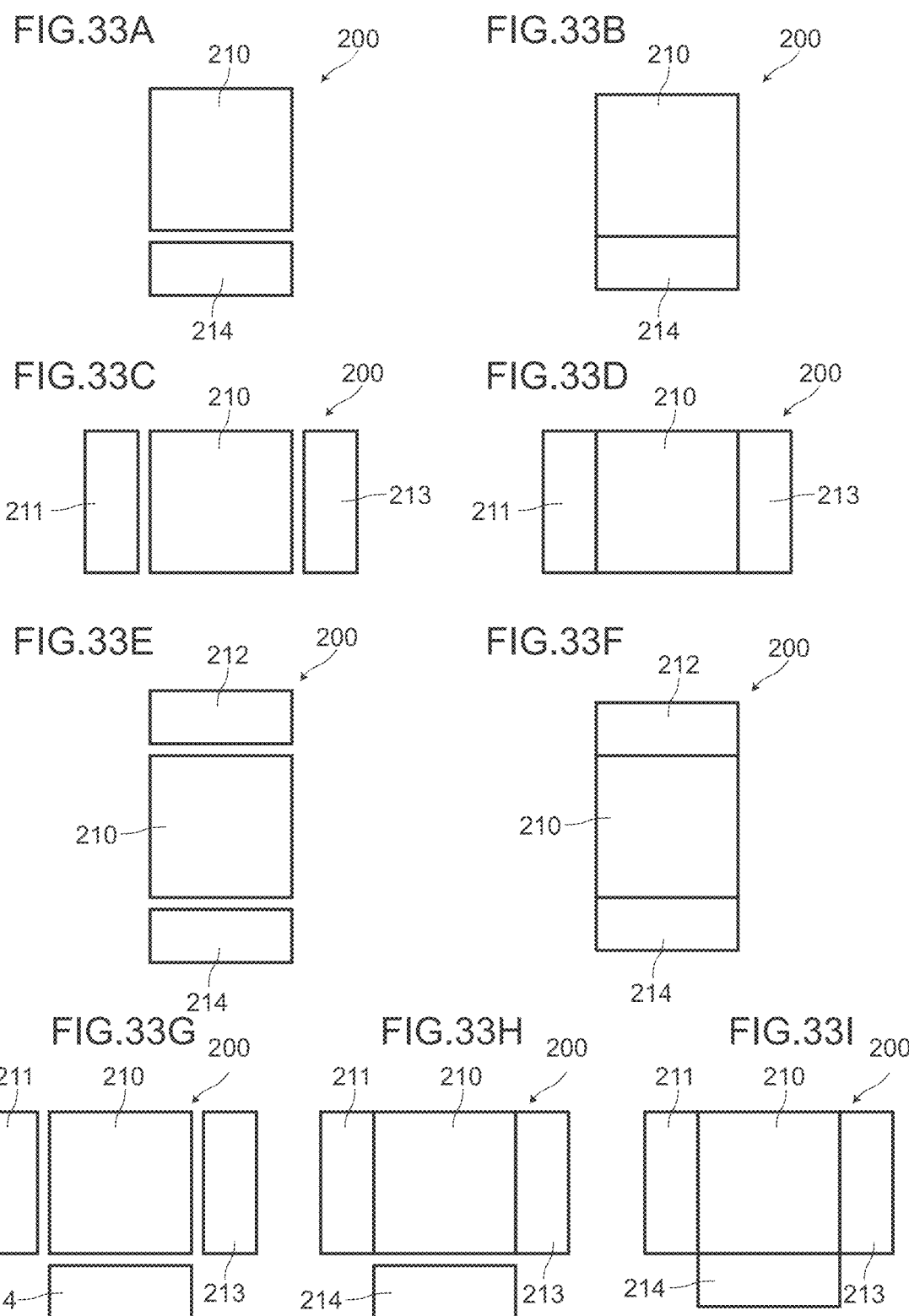

FIG. 33A to FIG. 33I are views illustrating one example of the case where the display unit 20 is formed of at least two display units. In FIG. 33A to FIG. 33I, as at least two display units, the display units 200 of the wristwatch or the wristwatch type display device each having two to four display units are illustrated in a developed form. In FIG. 33A to FIG. 33I, FIG. 33A and FIG. 33B illustrate cases where the wristwatch or the wristwatch type display device has two display units. FIG. 33C to FIG. 33F illustrate cases where the wristwatch or the wristwatch type display device has three display units. FIG. 33G to FIG. 33I illustrate cases where the wristwatch or the wristwatch type display device has four display units. As illustrated in the respective views in FIG. 33A to FIG. 33I, in the wristwatch or the wristwatch type display device having two to four display units, there exist faces that do not have a display unit formed of an organic EL display sheet. However, the protective member may be applied by coating also to the faces that do not have the display unit formed of the organic EL display sheet and are cured thereafter.

Further, as illustrated in the respective views in FIG. 33A to FIG. 33I, also in the case where the wristwatch or the wristwatch type display device has two to four display units, the display units may be formed of a plurality of organic EL display sheets or may be formed of one organic EL display sheet. That is, FIG. 33A and FIG. 33H illustrate the case where the display units are formed of two organic EL display sheets. FIG. 33C and FIG. 33E illustrate the case where display units are formed of three organic EL display sheets. FIG. 33G illustrates the case where the respective display units are formed of four organic EL display sheets. FIG. 33B, FIG. 33D, FIG. 33F and FIG. 33I illustrate the case where the respective display units are formed of one organic EL display sheet.

In FIG. 32 and FIG. 33A to FIG. 33I, there are cases where the upper face display unit 210 has a square shape. However, as illustrated in FIG. 1A and FIG. 1B used in the above-mentioned description of the embodiment, the upper face display unit 210 may have a rectangular shape. On the other hand, although the upper face display unit 210 has a rectangular shape in the above-mentioned embodiment, the upper face display unit 210 may have a square shape.

In the wristwatch or the wristwatch type display device according to the present invention, the case is exemplified where the display unit 200 (five display units 210 to 214) is formed of the organic EL display sheets. However, the display unit 200 (five display units 210 to 214) may be formed of micro light emitting diode (LED) display sheets.

The wristwatch or the wristwatch type display device according to the present invention is not limited to the displays in the display modes described in the above-mentioned embodiments. For example, the wristwatch or the wristwatch type display device according to the present invention perform the displays in display modes can illustrated in FIG. 34 and FIG. 35 (display modes where the display is switched over by a swipe operation).

Figure 34:
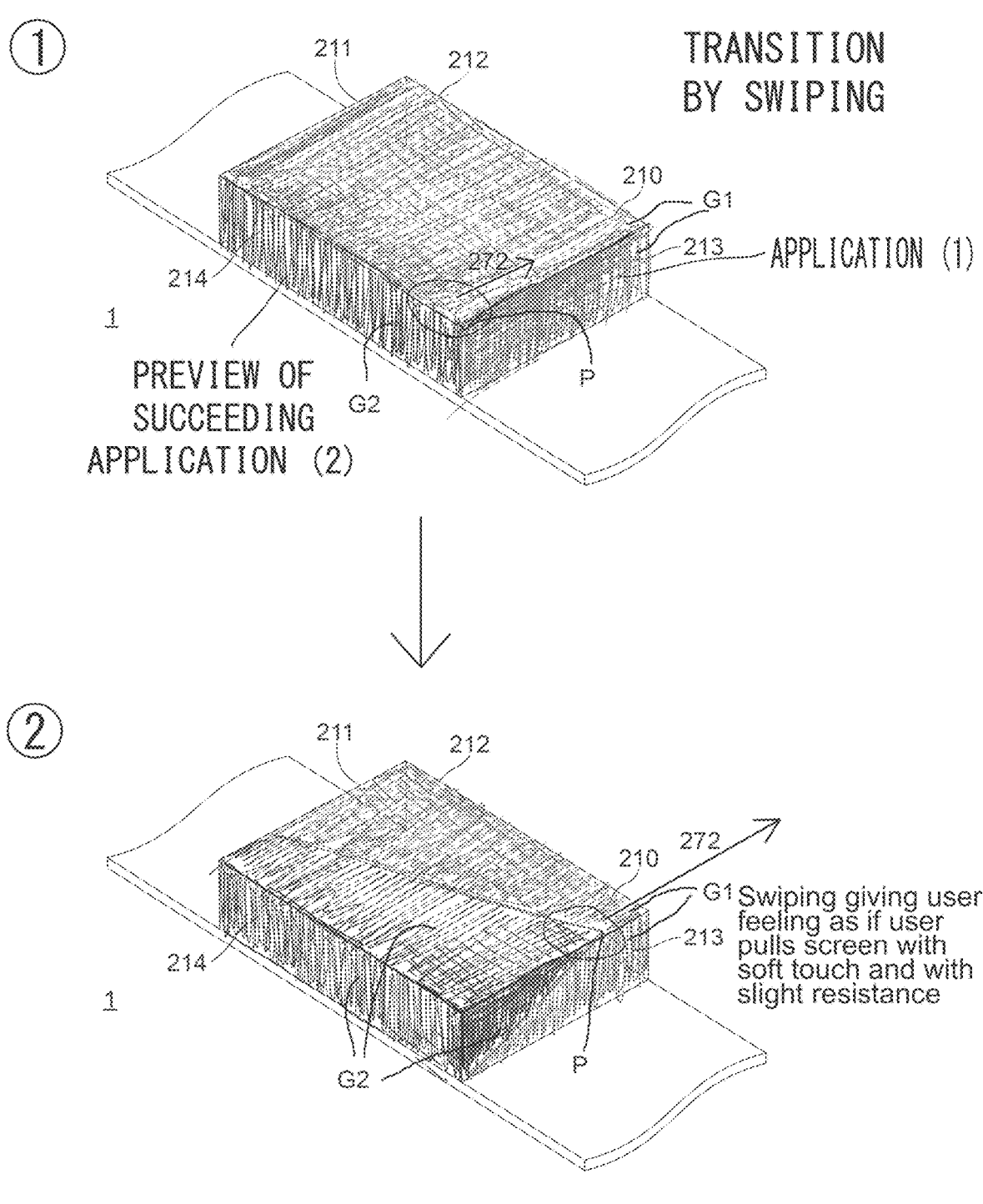
Figure 36:
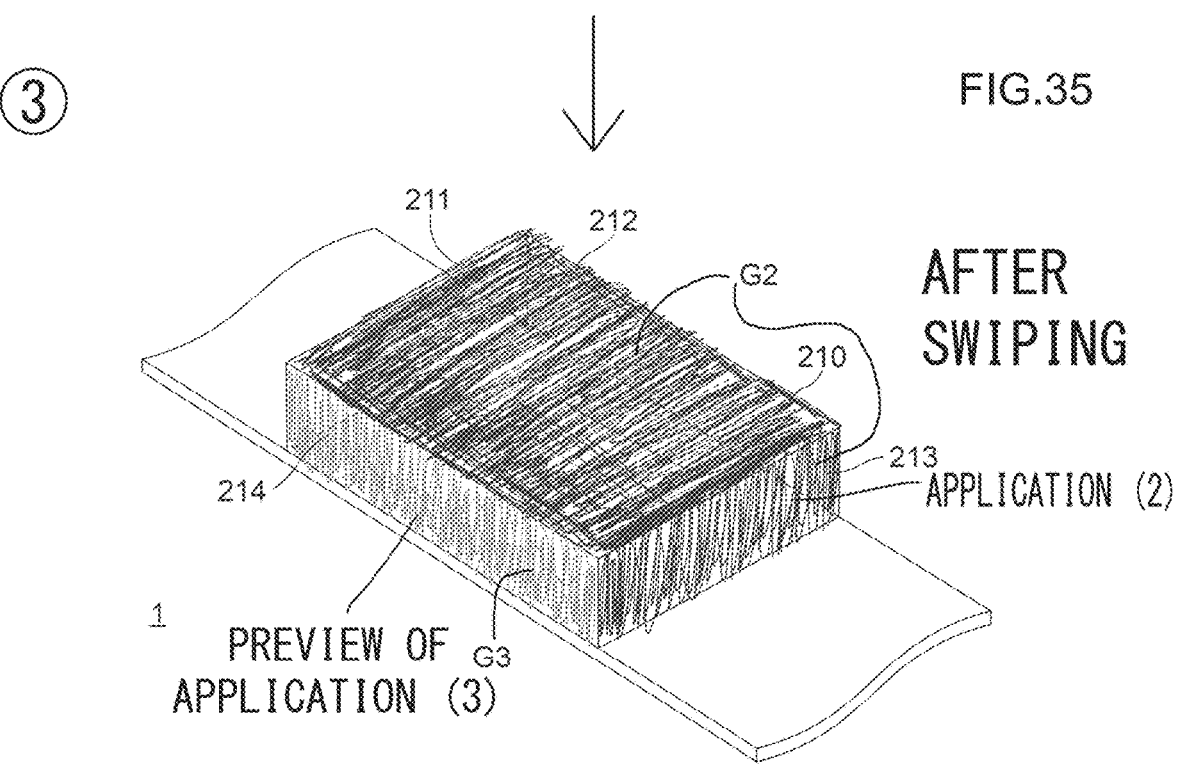

FIG. 34 and FIG. 35 are views for describing a display mode where a display is changed over by a swipe operation. As illustrated in an upper view in FIG. 34, in the display mode where the display is changed over by the swipe operation, as an initial state, a first image G1 is displayed on four display units consisting of the upper face display unit 210, the first side face display unit 211, the second side face display unit 212 and the third side face display unit 213, and a second image G2 is displayed on the remaining fourth side face display unit 214. Then, as illustrated in a lower view in FIG. 34, a display is performed where, when a user swipes an arbitrary portion P on a boundary between the first image G1 and the second image G2 using his/her finger, the boundary between the first image G1 and the second image G2 and a boundary between the second image G2 and a third image G3 not illustrated in the drawing are moved by pulling. Then, the user further swipes the arbitrary portion P using his/her finger. When the swiping operation is finished, as illustrated in FIG. 35, the display control unit 450 performs a control as if the boundary between the first image G1 and the second image G2 and the boundary between the second image G2 and the third image G3 are stopped by being attracted by something.

As a display example where a display is changed over by a swipe operation, for example, the changeover between an analog display and a digital display, a changeover between a watch display and a calendar display, the release of locking and the like can be exemplified. However, besides these changeovers, various display changeovers can be performed. In the wristwatch 1 according to the embodiment, the display control unit 450 controls the display on each of five display units 210 to 214 such that the above-mentioned display mode can be realized.

To realize display mode described above, as five display units 210 to 214, touch panels that are prepared by disposing a touch pad on a surface of each of five respective organic EL display sheets are used. The touch pad may be disposed on a surface of the black member 280 or the protective member 290.

The invention claimed is:

1. A wristwatch, comprising:
   a wristwatch body having a rectangular parallelepiped shape, the wristwatch body comprising at least six faces including:
      a top face,
      a bottom face configured to face toward an arm of a user at a time of wearing the wristwatch on the arm, and
      four side faces each adjacent to the top face;
   five display units including:
      an upper display unit formed over an entire area of the top face of the wristwatch body, and
      four side display units each formed over an entire area of a respective one of the four side faces of the wristwatch body;
   a display control unit configured to control a display on each of the five display units; and
   a detection unit configured to detect at least one information out of
      position information of the wristwatch,
      posture information of the wristwatch,
      movement information of the wristwatch, and
      health relating information of the user of the wristwatch,
wherein
   the display control unit is configured to
      control the display on each of the five display units based on the at least one information detected by the detection unit, and
      control the display displayed on the top face and the display displayed on at least one of the four side faces to move an image in a seamless manner by straddling the upper display unit and at least one of the four side display units,
   the detection unit includes:
      at least one imaging element that is disposed on any portion of the wristwatch; and
      an arithmetic operation unit configured to, as the position information of the wristwatch, extract information relating to a positional relationship between eyes of the user of the wristwatch and the wristwatch based on an image of the eyes of the user who uses the wristwatch that is imaged by the at least one imaging element, the detection unit is configured to detect the information extracted by the arithmetic operation unit, and the display control unit is configured to control the display on each of the five display units in accordance with the information relating to the positional relationship detected by the detection unit, and the display control unit is further configured to control, in accordance with the information relating to the positional relationship detected by the detection unit, the display on each of the five display units to display time in an analog watch display mode in which an inside of the wristwatch body appears in a see-through manner, and numerals of an analog watch on one or more of the side display units not visible from the user are displayed individually in a reverse left and right display as viewed from the user.

2. A wristwatch, comprising:

a wristwatch body having a rectangular parallelepiped shape, the wristwatch body comprising at least six faces including:

a top face, a bottom face configured to face toward an arm of a user at a time of wearing the wristwatch on the arm, and four side faces each adjacent to the top face;

five display units including:

an upper display unit formed over an entire area of the top face of the wristwatch body, and four side display units each formed over an entire area of a respective one of the four side faces of the wristwatch body;

a display control unit configured to control a display on each of the five display units; and a detection unit configured to detect at least one information out of position information of the wristwatch, posture information of the wristwatch, movement information of the wristwatch, and health relating information of the user of the wristwatch, wherein the display control unit is configured to control the display on each of the five display units based on the at least one information detected by the detection unit, and control the display displayed on the top face and the display displayed on at least one of the four side faces to move an image in a seamless manner by straddling the upper display unit and at least one of the four side display units, the detection unit includes:

at least one imaging element that is disposed on any portion of the wristwatch; and an arithmetic operation unit configured to, as the position information of the wristwatch, extract information relating to a positional relationship between eyes of the user of the wristwatch and the wristwatch based on an image of the eyes of the user who uses the wristwatch that is imaged by the at least one imaging element, the detection unit is configured to detect the information extracted by the arithmetic operation unit, the display control unit is configured to control the display on each of the five display units in accordance with the information relating to the positional relationship detected by the detection unit, and the display control unit is configured to control, in accordance with the information relating to the positional relationship detected by the detection unit, the display on each of the five display units to rotate characters indicating time so as to enable the user to view the display of time in a horizontal state.

3. A wristwatch, comprising:

a wristwatch body having a rectangular parallelepiped shape, the wristwatch body comprising at least six faces including:

a top face, a bottom face configured to face toward an arm of a user at a time of wearing the wristwatch on the arm, and four side faces each adjacent to the top face;

five display units including:

an upper display unit formed over an entire area of the top face of the wristwatch body, and four side display units each formed over an entire area of a respective one of the four side faces of the wristwatch body;

a display control unit configured to control a display on each of the five display units; and a detection unit configured to detect at least one information out of position information of the wristwatch, posture information of the wristwatch, movement information of the wristwatch, and health relating information of the user of the wristwatch, wherein the display control unit is configured to control the display on each of the five display units based on the at least one information detected by the detection unit, control the display displayed on the top face and the display displayed on at least one of the four side faces to move an image in a seamless manner by straddling the upper display unit and at least one of the four side display units, the detection unit is a three-dimensional acceleration sensor configured to detect movement information of the wristwatch, the detection unit is configured to detect information relating to three-dimensional movement of the wristwatch as the movement information of the wristwatch, the display control unit is configured to control the display on each of the five display units in accordance with the information relating to the three-dimensional movement detected by the detection unit, and the display control unit is configured to control the display on each of the five display units, in response to a detection of acceleration that exceeds a threshold, to display a first state being alternately changed over between (1) a second state where numerals that indicate time are rotated in a predetermined direction and (2) a third state where the numerals that indicate time are rotated in a direction opposite to the predetermined direction.

4. A wristwatch, comprising:

a wristwatch body having a rectangular parallelepiped shape, the wristwatch body comprising at least six faces including:

a top face, a bottom face configured to face toward an arm of a user at a time of wearing the wristwatch on the arm, and four side faces each adjacent to the top face;

five display units including:

an upper display unit formed over an entire area of the top face of the wristwatch body, and four side display units each formed over an entire area of a respective one of the four side faces of the wristwatch body;

a display control unit configured to control a display on each of the five display units; and a detection unit configured to detect at least one information out of position information of the wristwatch, posture information of the wristwatch, movement information of the wristwatch, and health relating information of the user of the wristwatch, wherein the display control unit is configured to control the display on each of the five display units based on the at least one information detected by the detection unit, control the display displayed on the top face and the display displayed on at least one of the four side faces to move an image in a seamless manner by straddling the upper display unit and at least one of the four side display units, the detection unit is a three-dimensional acceleration sensor configured to detect movement information of the wristwatch, the detection unit is configured to detect information relating to three-dimensional movement of the wristwatch as the movement information of the wristwatch, the display control unit is configured to control the display on each of the five display units in accordance with the information relating to the three-dimensional movement detected by the detection unit, and the display control unit is configured to control the display on each of the five display units, in response to a detection of acceleration that exceeds a threshold, to move an image indicating present time on one of the five display units like a jelly and to stick out over another one of the five display units.

5. A wristwatch, comprising:

a wristwatch body having a rectangular parallelepiped shape, the wristwatch body comprising at least six faces including:

a top face, a bottom face configured to face toward an arm of a user at a time of wearing the wristwatch on the arm, and four side faces each adjacent to the top face;

five display units including:

an upper display unit formed over an entire area of the top face of the wristwatch body, and four side display units each formed over an entire area of a respective one of the four side faces of the wristwatch body;

a display control unit configured to control a display on each of the five display units; and a detection unit configured to detect at least one information out of position information of the wristwatch, posture information of the wristwatch, movement information of the wristwatch, and health relating information of the user of the wristwatch, wherein the display control unit is configured to control the display on each of the five display units based on the at least one information detected by the detection unit, and control the display displayed on the top face and the display displayed on at least one of the four side faces to move an image in a seamless manner by straddling the upper display unit and at least one of the four side display units, the detection unit is a three-dimensional acceleration sensor configured to detect movement information of the wristwatch, the detection unit is configured to detect information relating to three-dimensional movement of the wristwatch as the movement information of the wristwatch, the display control unit is configured to control the display on each of the five display units in accordance with the information relating to the three-dimensional movement detected by the detection unit, and the display control unit is configured to control the display on each of the five display units, in response to a detection of acceleration that exceeds a threshold, to display a pseudo wristwatch frame appearing to shake like a jelly in an inside of the wristwatch.

6. A wristwatch, comprising:

a wristwatch body having a rectangular parallelepiped shape, the wristwatch body comprising at least six faces including:

a top face, a bottom face configured to face toward an arm of a user at a time of wearing the wristwatch on the arm, and four side faces each adjacent to the top face;

five display units including:

an upper display unit formed over an entire area of the top face of the wristwatch body, and four side display units each formed over an entire area of a respective one of the four side faces of the wristwatch body;

a display control unit configured to control a display on each of the five display units; and a detection unit configured to detect at least one information out of position information of the wristwatch, posture information of the wristwatch, movement information of the wristwatch, and health relating information of the user of the wristwatch, wherein the display control unit is configured to control the display on each of the five display units based on the at least one information detected by the detection unit, and control the display displayed on the top face and the display displayed on at least one of the four side faces to move an image in a seamless manner by straddling the upper display unit and at least one of the four side display units, the detection unit is a three-dimensional acceleration sensor configured to detect movement information of the wristwatch, the detection unit is configured to detect information relating to three-dimensional movement of the wristwatch as the movement information of the wristwatch, the display control unit is configured to control the display on each of the five display units in accordance with the information relating to the three-dimensional movement detected by the detection unit, and the display control unit is configured to control the display on each of the five display units, in response to a detection of acceleration that exceeds a threshold, to change over the display of present time to a display of winding of a ribbon.

7. A wristwatch, comprising:

a wristwatch body having a rectangular parallelepiped shape, the wristwatch body comprising at least six faces including: a top face, a bottom face configured to face toward an arm of a user at a time of wearing the wristwatch on the arm, and four side faces each adjacent to the top face; five display units including:

an upper display unit formed over an entire area of the top face of the wristwatch body, and four side display units each formed over an entire area of a respective one of the four side faces of the wristwatch body;

a display control unit configured to control a display on each of the five display units; and a detection unit configured to detect at least one information out of position information of the wristwatch, posture information of the wristwatch, movement information of the wristwatch, and health relating information of the user of the wristwatch, wherein the display control unit is configured to control the display on each of the five display units based on the at least one information detected by the detection unit, and control the display displayed on the top face and the display displayed on at least one of the four side faces to move an image in a seamless manner by straddling the upper display unit and at least one of the four side display units, the detection unit is a three-dimensional acceleration sensor configured to detect movement information of the wristwatch, the detection unit is configured to detect information relating to three-dimensional movement of the wrist- watch as the movement information of the wristwatch, the display control unit is configured to control the display on each of the five display units in accordance with the information relating to the three-dimensional movement detected by the detection unit, and the display control unit is configured to control the display on each of the five display units, in response to a detection of acceleration that exceeds a threshold, to display present time in a display mode where fine particles are infiltrated into the wristwatch body.

8. A wristwatch, comprising:

a wristwatch body having a rectangular parallelepiped shape, the wristwatch body comprising at least six faces including:

a top face, a bottom face configured to face toward an arm of a user at a time of wearing the wristwatch on the arm, and four side faces each adjacent to the top face;

five display units including:

an upper display unit formed over an entire area of the top face of the wristwatch body, and four side display units each formed over an entire area of a respective one of the four side faces of the wristwatch body;

a display control unit configured to control a display on each of the five display units; and a detection unit configured to detect at least one information out of position information of the wristwatch, posture information of the wristwatch, movement information of the wristwatch, and health relating information of the user of the wristwatch, wherein the display control unit is configured to control the display on each of the five display units based on the at least one information detected by the detection unit, and control the display displayed on the top face and the display displayed on at least one of the four side faces to move an image in a seamless manner by straddling the upper display unit and at least one of the four side display units, the detection unit is a three-dimensional acceleration sensor configured to detect movement information of the wristwatch, the detection unit is configured to detect information relating to three-dimensional movement of the wrist- watch as the movement information of the wristwatch, the display control unit is configured to control the display on each of the five display units in accordance with the information relating to the three-dimensional move- ment detected by the detection unit, and the display control unit is configured to control the display on each of the five display units, in response to a detection of acceleration that exceeds a threshold, to display a transparent vessel filled with a liquid and the liquid is increased and decreased when the liquid swings in the transparent vessel.

9. A wristwatch, comprising:

a wristwatch body having a rectangular parallelepiped shape, the wristwatch body comprising at least six faces including:

a top face, a bottom face configured to face toward an arm of a user at a time of wearing the wristwatch on the arm, and four side faces each adjacent to the top face;

five display units including:

an upper display unit formed over an entire area of the top face of the wristwatch body, and four side display units each formed over an entire area of a respective one of the four side faces of the wristwatch body;

a display control unit configured to control a display on each of the five display units; and a detection unit configured to detect at least one information out of
position information of the wristwatch,
posture information of the wristwatch,
movement information of the wristwatch, and
health relating information of the user of the wristwatch, wherein the display control unit is configured to control the display on each of the five display units based on the at least one information detected by the detection unit, and control the display displayed on the top face and the display displayed on at least one of the four side faces to move an image in a seamless manner by straddling the upper display unit and at least one of the four side display units, the detection unit includes at least one of a pulse gauge, a thermometer, a blood pressure gauge, an electrocardiograph gauge or a three-dimensional acceleration sensor configured to detect health relating information of the user of the wristwatch, the detection unit is configured to detect information relating to at least one of a pulse, a body temperature, a blood pressure or activity of the user of the wristwatch as the health relating information of the user of the wristwatch, the display control unit is configured to control the display on each of the five display units in accordance with the health relating information of the user of the wristwatch detected by the detection unit, and the detection unit is configured to detect the blood pressure of the user of the wristwatch, and the display control unit is configured to control the display on each of the five display units such that, in response to the blood pressure detected by the detection unit being normal, a circular annular area and an internal area are displayed within a range of the upper display unit, and in response to the blood pressure detected by the detection unit being abnormal, either the circular annular area or the internal area becomes large and is displayed in such a manner that either the circular annular area or the internal area sticks out over one or more of the side display units.

10. A wristwatch, comprising:

a wristwatch body having a rectangular parallelepiped shape, the wristwatch body comprising at least six faces including:

a top face, a bottom face configured to face toward an arm of a user at a time of wearing the wristwatch on the arm, and four side faces each adjacent to the top face;

five display units including:

an upper display unit formed over an entire area of the top face of the wristwatch body, and four side display units each formed over an entire area of a respective one of the four side faces of the wristwatch body;

a display control unit configured to control a display on each of the five display units; and a detection unit configured to detect at least one information out of
position information of the wristwatch,
posture information of the wristwatch,
movement information of the wristwatch, and health relating information of the user of the wristwatch, wherein the display control unit is configured to control the display on each of the five display units based on the at least one information detected by the detection unit, and control the display displayed on the top face and the display displayed on at least one of the four side faces to move an image in a seamless manner by straddling the upper display unit and at least one of the four side display units, the detection unit includes at least one of a pulse gauge, a thermometer, a blood pressure gauge, an electrocardiograph gauge or a three-dimensional acceleration sensor configured to detect health relating information of the user of the wristwatch, the detection unit is configured to detect information relating to at least one of a pulse, a body temperature, a blood pressure or activity of the user of the wristwatch as the health relating information of the user of the wristwatch, the display control unit is configured to control the display on each of the five display units in accordance with the health relating information of the user of the wristwatch detected by the detection unit, and the detection unit is configured to detect the pulse of the user of the wristwatch, and the display control unit is configured to control the display on each of the five display units such that a pulse display including a heart mark is displayed at a center of the upper display unit, and the heart mark flickers corresponding to pulses detected by the detection unit.

11. A wristwatch, comprising:

a wristwatch body having a rectangular parallelepiped shape, the wristwatch body comprising at least six faces including:

a top face, a bottom face configured to face toward an arm of a user at a time of wearing the wristwatch on the arm, and four side faces each adjacent to the top face;

five display units including:

an upper display unit formed over an entire area of the top face of the wristwatch body, and four side display units each formed over an entire area of a respective one of the four side faces of the wristwatch body;

a display control unit configured to control a display on each of the five display units; and a detection unit configured to detect at least one information out of
position information of the wristwatch,
posture information of the wristwatch,
movement information of the wristwatch, and
health relating information of the user of the wristwatch, wherein the display control unit is configured to control the display on each of the five display units based on the at least one information detected by the detection unit, and control the display displayed on the top face and the display displayed on at least one of the four side faces to move an image in a seamless manner by straddling the upper display unit and at least one of the four side display units, the detection unit includes at least one of a pulse gauge, a thermometer, a blood pressure gauge, an electrocardiograph gauge or a three-dimensional acceleration sensor configured to detect health relating information of the user of the wristwatch, the detection unit is configured to detect information relating to at least one of a pulse, a body temperature, a blood pressure or activity of the user of the wristwatch as the health relating information of the user of the wristwatch, the display control unit is configured to control the display on each of the five display units in accordance with the health relating information of the user of the wristwatch detected by the detection unit, and the detection unit is configured to detect the pulse of the user of the wristwatch, and the display control unit is configured to control the display on each of the five display units to display (1) an information display relating to a reproduction of a music on the upper display unit, and (2) a display of a visualizer as information of pulses of the user on at least one of the side display units.

12. A wristwatch, comprising:

a wristwatch body having a rectangular parallelepiped shape, the wristwatch body comprising at least six faces including:

a top face, a bottom face configured to face toward an arm of a user at a time of wearing the wristwatch on the arm, and four side faces each adjacent to the top face;

five display units including:

an upper display unit formed over an entire area of the top face of the wristwatch body, and four side display units each formed over an entire area of a respective one of the four side faces of the wristwatch body;

a display control unit configured to control a display on each of the five display units; and a detection unit configured to detect at least one information out of position information of the wristwatch, posture information of the wristwatch, movement information of the wristwatch, and health relating information of the user of the wristwatch, wherein the display control unit is configured to control the display on each of the five display units based on the at least one information detected by the detection unit, and control the display displayed on the top face and the display displayed on at least one of the four side faces to move an image in a seamless manner by straddling the upper display unit and at least one of the four side display units, the detection unit includes at least one of a pulse gauge, a thermometer, a blood pressure gauge, an electrocardiograph gauge or a three-dimensional acceleration sensor configured to detect health relating information of the user of the wristwatch, the detection unit is configured to detect information relating to at least one of a pulse, a body temperature, a blood pressure or activity of the user of the wristwatch as the health relating information of the user of the wristwatch, the display control unit is configured to control the display on each of the five display units in accordance with the health relating information of the user of the wristwatch detected by the detection unit, and the detection unit is configured to detect the body temperature of the user of the wristwatch, and the display control unit is configured to control the display on each of the five display units such that a region that indicates a high temperature area and a low temperature area of the detected body temperature is displayed on a strip-shaped display extending from one of the side display units to another one of the side display units through the upper display unit.

\* \* \* \* \*